(12) United States Patent
Dinville et al.

(10) Patent No.: US 9,763,803 B2
(45) Date of Patent: Sep. 19, 2017

(54) ANCHORING DEVICE AND SYSTEM FOR AN INTERVERTEBRAL IMPLANT, INTERVERTEBRAL IMPLANT AND IMPLANTATION INSTRUMENT

(71) Applicant: LDR Medical, Rosières Près Troyes (FR)

(72) Inventors: Hervé Dinville, St Parres aux Tertres (FR); Samuel Lequette, Troyes (FR); Manuel Delhaye, Avrille (FR); Henry François Parent, Angers (FR); Alexis Faline, Collonges-au-Mont-D'or (DE); Pablo Lawner, Riverside, CA (US); Faissal Zahrawi, Celebration, FL (US); Thomas Bierstedt, Recklinghausen (DE)

(73) Assignee: LDR Medical, Sainte-Savine (FR)

( * ) Notice: Subject to any disclaimer, the term of this patent is extended or adjusted under 35 U.S.C. 154(b) by 0 days.

(21) Appl. No.: 14/726,558

(22) Filed: May 31, 2015

(65) Prior Publication Data

US 2015/0257896 A1 Sep. 17, 2015

Related U.S. Application Data

(63) Continuation of application No. 13/538,078, filed on Jun. 29, 2012, now Pat. No. 9,044,337, which is a (Continued)

(51) Int. Cl.
*A61F 2/44* (2006.01)
*A61B 17/84* (2006.01)
(Continued)

(52) U.S. Cl.
CPC ........ *A61F 2/4455* (2013.01); *A61B 17/7074* (2013.01); *A61B 17/7076* (2013.01);
(Continued)

(58) Field of Classification Search
CPC . A61B 17/7074; A61B 17/7076; A61B 17/84; A61B 17/846; A61F 2/44;
(Continued)

(56) References Cited

U.S. PATENT DOCUMENTS 4,135,506 A * 1/1979 Ulrich ................ A61B 17/8872
606/207
9,044,337 B2 * 6/2015 Dinville ................ A61F 2/447
(Continued)

*Primary Examiner* — Larry E Waggle, Jr.
(74) *Attorney, Agent, or Firm* — Lauff Law PLLC

(57) ABSTRACT

Anchoring devices, anchoring systems for intervertebral implants, intervertebral implants, and instruments and methods for implanting implants are disclosed. In preferred configurations, these various objects share the feature of comprising or cooperating with an anchoring device having a body comprising at least one curved plate elongated along a longitudinal axis, designed to be inserted through a passage crossing at least a part of implant, in order to penetrate into at least one vertebral endplate and attach implant onto this vertebral endplate by means of at least one stop retaining the implant, characterized in that the body comprises at least one longitudinal rib on at least a part of at least one of its faces, said rib being designed to cooperate with a groove made in passage of implant. In some preferred configurations, anchoring device comprises withdrawal stops or latches, and/or means for withdrawing the anchor from an inserted position.

20 Claims, 20 Drawing Sheets

Related U.S. Application Data continuation of application No. PCT/IB2009/008048, filed on Dec. 31, 2009.

(51) Int. Cl.
*A61B 17/70* (2006.01)
*A61F 2/46* (2006.01)
*A61F 2/30* (2006.01)

(52) U.S. Cl.
CPC ............ *A61B 17/84* (2013.01); *A61B 17/846* (2013.01); *A61F 2/44* (2013.01); *A61F 2/442* (2013.01); *A61F 2/447* (2013.01); *A61F 2/4425* (2013.01); *A61F 2/46* (2013.01); *A61F 2/4603* (2013.01); *A61F 2/4611* (2013.01); *A61F 2/4637* (2013.01); *A61F 2002/30401* (2013.01); *A61F 2002/30403* (2013.01); *A61F 2002/30428* (2013.01); *A61F 2002/30472* (2013.01); *A61F 2002/30576* (2013.01); *A61F 2002/30578* (2013.01); *A61F 2002/30579* (2013.01); *A61F 2002/30604* (2013.01); *A61F 2002/30782* (2013.01); *A61F 2002/30785* (2013.01); *A61F 2002/30787* (2013.01); *A61F 2002/30879* (2013.01); *A61F 2002/30889* (2013.01); *A61F 2002/4475* (2013.01); *A61F 2002/4619* (2013.01); *A61F 2002/4623* (2013.01); *A61F 2002/4629* (2013.01); *A61F 2002/4641* (2013.01); *A61F 2220/0008* (2013.01); *A61F 2220/0016* (2013.01); *A61F 2220/0025* (2013.01); *A61F 2220/0041* (2013.01)

(58) Field of Classification Search
CPC .......... A61F 2/442; A61F 2/4455; A61F 2/46; A61F 2/4603; A61F 2/4611; A61F 2002/4619; A61F 2/4637; A61F 2002/4641; A61F 2220/0008; A61F 2220/0016

See application file for complete search history.

(56) References Cited

U.S. PATENT DOCUMENTS

| | | | |
|---|---|---|---|
| 2009/0105832 A1* | 4/2009 | Allain | A61B 17/0642 623/17.16 |
| 2013/0123926 A1* | 5/2013 | Bae | A61B 17/846 623/17.16 |

* cited by examiner

Figure 7A
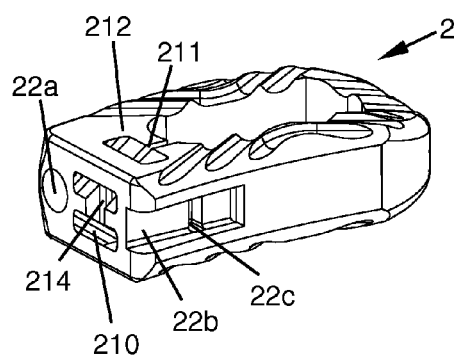
Figure 7B
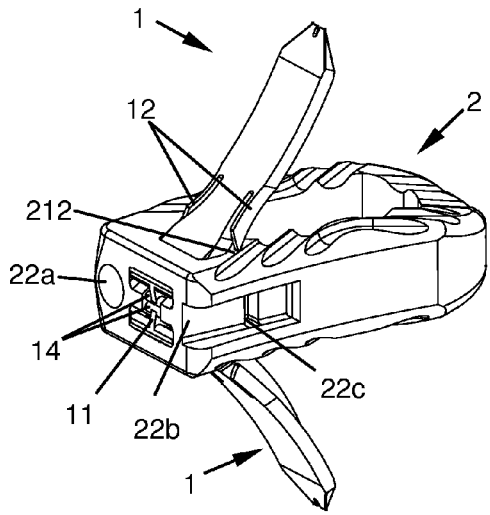
Figure 7C
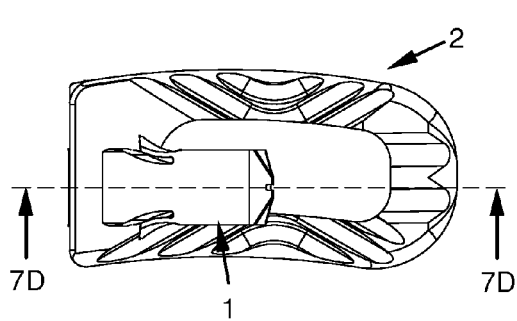
Figure 7D
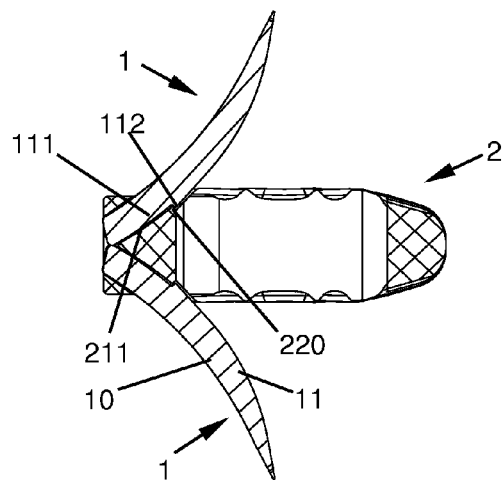
Figure 7E
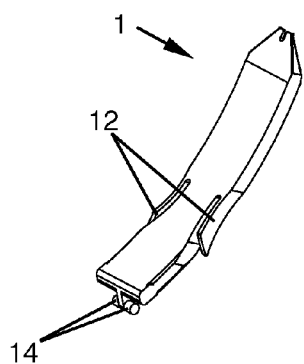
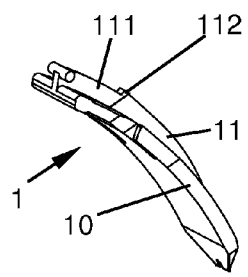

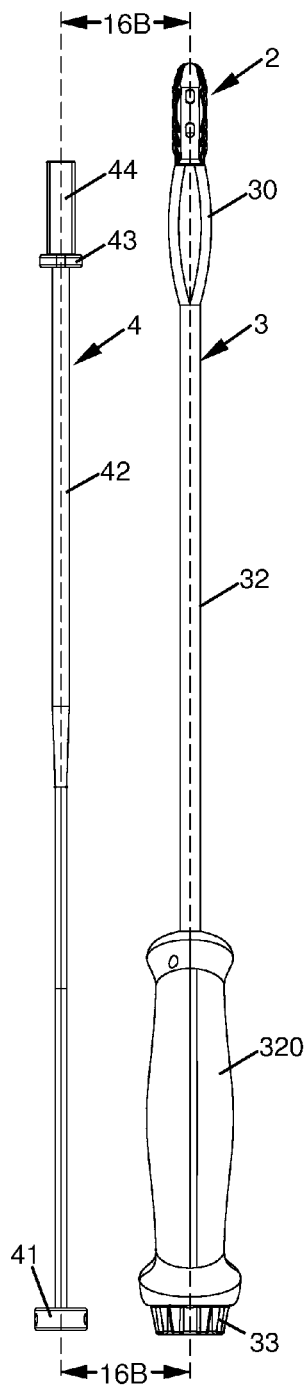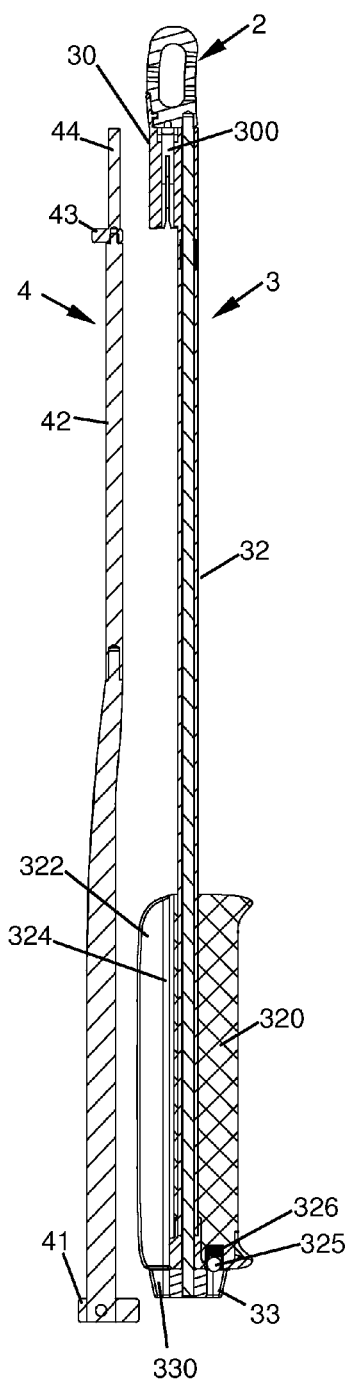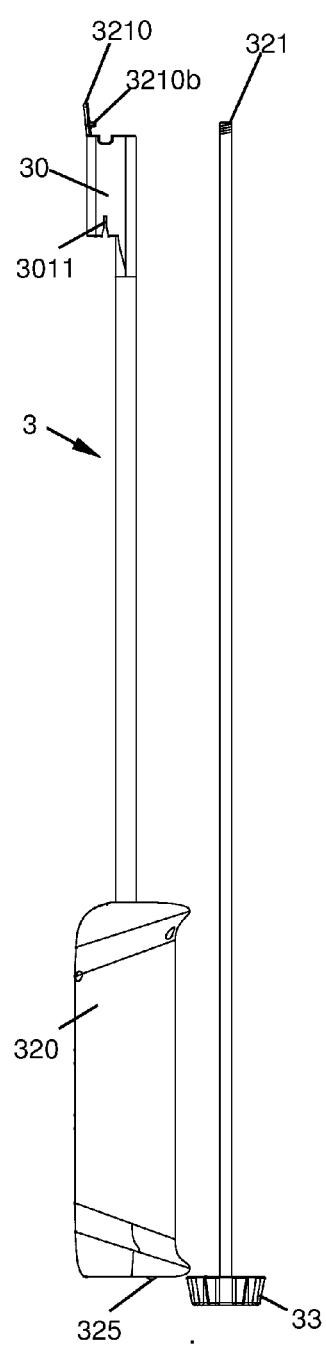

ANCHORING DEVICE AND SYSTEM FOR AN INTERVERTEBRAL IMPLANT, INTERVERTEBRAL IMPLANT AND IMPLANTATION INSTRUMENT

CROSS-REFERENCE TO RELATED APPLICATION

This application is a continuation of U.S. patent application Ser. No. 13/538,078 filed Jun. 29, 2012, and issuing as U.S. Pat. No. 9,044,337 on Jun. 2, 2015, which is a continuation of International Application PCT/IB2009/008048 filed Dec. 31, 2009, and entering the national stage in the United States on Jun. 29, 2012, as U.S. patent application Ser. No. 13/520,041. U.S. patent application Ser. No. 13/538,078 is a U.S. national application under 35 U.S.C. §111(a) filed during the pendency of International Application PCT/IB2009/008048, which designates the United States, and U.S. patent application Ser. No. 13/538,078 claims the benefit of the Dec. 31, 2009, filing date of International Application PCT/IB2009/008048 under 35 U.S.C. §§120 and 365(c). International Application PCT/IB2009/008048 is incorporated herein by reference.

BACKGROUND

The present invention concerns orthopedic implants, including spinal implants such as intervertebral prostheses and intersomatic cages, for example. Intervertebral prostheses may be implanted between two adjacent vertebrae to maintain or restore a space between the vertebrae while conserving mobility of vertebrae. Intersomatic cages may be implanted between two adjacent vertebrae for placement and growth of bone tissue grafts (or a substitute) in the disc space and to obtain an arthrodesis (the fusion of the two vertebrae). For example, after the cage is positioned, the intervertebral space may be filled with autologous spongy bone or suitable bone substitutes, which may also (or in the alternative) be placed in a cavity in the cage, prior to its positioning in the intervertebral space. In particular, the invention concerns intervertebral implants, implant anchors, the fixation of implants to vertebrae by anchors, and implantation of implants in the disc space by an implantation instrument.

One problem in this field concerns the stability of spinal implants in the disc space once they have been implanted, particularly when an arthrodesis is desired, for example using intersomatic cages or other implants allowing an arthrodesis. For example, there is a risk that the implant will shift in the intervertebral space due to forces imposed when the patient moves, even when the implant is provided with notches or teeth on its vertebral contact surfaces. Therefore it is often necessary to affix the spinal implant to the adjacent vertebrae between which it is implanted. Solutions are known in the prior art that provide the spinal implant with a bone anchoring device that allows solidly attaching the implant into the vertebral endplates of the vertebrae between which the implant is designed to be implanted. Moreover, access to the intervertebral spaces (disc spaces) is often particularly delicate due to the dimensions involved, particularly due to the presence of blood vessels and nerves in the approach to the intervertebral space. Bone anchoring devices must penetrate into the vertebrae with sufficient depth to ensure a good fixation, and must also have a small size and allow affixing the implant without endangering the surrounding blood vessels and nerves (for example, by not requiring more space in the approach to the intervertebral space than necessary for implantation of the spinal implant itself).

In the prior art, notably from published applications FR 2,916,956, US 2009/105832, and WO 2008/149223 filed by the assignee of the present application, which are incorporated herein by reference and to which the reader can refer to examine various problems resolved and various advantages provided by this type of solution, an anchoring device is known, suitable to be implanted solidly and with sufficient depth in the vertebral endplates to ensure that the implant is held tight against these vertebrae, but along an axis of approach for insertion generally in the plane of the intervertebral space. This type of solution typically comprises at least one anchor formed of a curved and rigid plate, arranged so as to penetrate into the endplate of a vertebra through an implant and provided with at least one stop to hold this implant against this vertebra. The rigidity of this type of anchor is an important feature to allow effective fixation, notably more effective than staples or other thin and/or relatively flexible and often fragile devices.

These types of anchoring devices (or "anchors") comprising a curved plate may pose a problem of the risk of splitting the vertebra during the impaction of the anchors into the vertebra, or due to forces imposed on the implant and/or the anchor once it is implanted in the vertebra. These types of anchors also may present a risk of making a cut that is too large during the impaction of the anchors into the vertebra, allowing the possibility of undesirable play of the anchor, which makes the implant fixation weak and/or unreliable. It should be noted that the term impaction is used here to designate the fact that the anchoring device is driven into the vertebra. It will also be noted that the present application describes an impactor, which is a device for impaction of the anchor because it is arranged to help driving an anchoring device into a vertebra.

Another potential problem of these types of anchors having a curved plate concerns its rigidity. In some circumstances, it is important that the anchor is rigid enough that it will not deform and/or have much play under the effects of the forces that are exerted on it, so that it will not gradually come out of the vertebra in which it is embedded. In addition, passage of the anchor through the implant and maintenance of the stability of such anchor within the implant (subject to an eventual desired play, for instance minimum play) is also an aspect that is important to ensure reliable mounting in some circumstances.

SUMMARY

Certain embodiments incorporating various technical features described in the present application therefore aim to alleviate one or more of these and/or other disadvantages of the prior art by proposing an anchoring device for intervertebral implants that can be (more) compact (with lesser encumbrance) and (more) easily implantable, especially along an axis substantially perpendicular to the axis of the spine, and that can be rigid and allow (more) reliable fixation with reduced risk of damaging the vertebrae.

This goal is attained, for example, by a device for anchoring intervertebral implant in the vertebrae, comprising a body comprising at least one curved plate elongated along a longitudinal axis extending between a first end, called anterior, designed to penetrate into a vertebra and a second end, called posterior, anchoring device being designed to be inserted through a passage crossing at least a portion of implant, in order to penetrate into at least one vertebral endplate and affix implant in this vertebral endplate by means of a stop retaining the implant, characterized in that the body comprises at least one longitudinal rib on at least a part of at least one of its faces, said rib being designed to cooperate with at least one groove in passage of implant.

According to another feature, the height of said rib varies along the longitudinal axis of body.

According to another feature, the height of said rib varies along the longitudinal axis of body.

According to another feature, curved plate of the body describes at least one arc of a circle or ellipse having dimensions and at least one radius of curvature made in such a way that anchoring device can be implanted in a vertebral endplate along an axis of approach forming an approximately 90° with the vertical axis of the spine, while having its longitudinal axis essentially in the plane of the intervertebral space.

According to another feature, the anterior end comprises at least one chamfer or at least one bevel facilitating penetration of device into the vertebrae.

According to another feature, the anterior end comprises at least one notch facilitating penetration of device into the vertebrae.

According to another feature, the body is provided with notches oriented so as to oppose the withdrawal of device once it is implanted in a vertebra.

According to another feature, the body comprises at least one stop, called retaining, comprising at least one stop surface oriented essentially facing the anterior end, designed to cooperate with at least one stop surface on implant that device is designed to affix, in order to hold implant against the vertebra in which device is designed to be anchored.

According to another feature, the retaining stop comprises at least one projecting lug on at least one face of the body of anchoring device.

According to another feature, the retaining stop comprises two projecting lugs on the lateral sides of the body of anchoring device.

According to another feature, the retaining stop comprises two lugs projecting perpendicularly to rib, at the level of the posterior end.

According to another feature, the body comprises at least one flexible lug oriented toward the posterior end and forming a withdrawal stop opposing the withdrawal of anchoring device.

According to another feature, the curvature of plate is oriented in the depth of plate.

According to another feature, the curvature of plate is oriented in the width of plate.

According to another feature, the anchoring device comprises, near the posterior end of plate, at least one portion of greater thickness than the thickness of the rest of plate, limiting the play of the device in passage of implant.

According to another feature, the body comprises, near the posterior end, at least one recess created to receive a tool to extract the device and allowing the withdrawal of the anchoring device.

According to another feature, the recess is open on the posterior end of the body, so that the tool can penetrate directly into said recess.

According to another feature, the stop end of flexible lug can be disengaged from stop of the implant through a channel emerging outside implant.

According to another feature, the anchoring device comprises at least one opening crossing plate to allow bone growth through device once it is implanted.

According to another feature, rib comprises a notch situated at a distance from the posterior end determined so this notch is stopped on a stop surface at the end of passage of implant.

Another goal of various embodiments incorporating various technical features described in the present application is to alleviate one or more of said (and/or other) disadvantages of the prior art by proposing a system of intervertebral anchoring that can be implanted substantially in the plane of the intervertebral space and that allows reliable fixation of the implant.

This goal is attained, for example, by a system for anchoring intervertebral implant in the vertebrae, characterized in that it comprises two devices according to the invention, the first anchoring device comprising a stop called cooperation, comprising at least one stop surface oriented essentially facing the anterior end and the second anchoring device comprising a stop, called cooperation, comprising at least one stop surface oriented essentially in the direction facing the posterior end, these two cooperation stops being made so as to cooperate with each other.

According to another feature, stop of the second anchoring device comprises a second stop surface, oriented essentially facing the anterior end, and the first device comprises a flexible lug positioned so that its posterior stop end comes into contact with the second stop surface of stop then serving to support flexible lug, thus impeding the withdrawal of the first device retaining the second device once it is in place in implant.

According to another feature, the stop end of flexible lug of the first device can be disengaged from the second stop surface of stop of the second device through a channel emerging outside the implant.

Another goal of certain embodiments incorporating various technical features described in the present application is to alleviate one or more of said (and/or other) disadvantages of the prior art by proposing an intervertebral implant that can be implanted substantially in the plane of the intervertebral space, which can be attached solidly to the vertebrae by means of an anchoring device that can be implanted substantially in the plane of the intervertebral space.

This goal is attained, for example, by an Intervertebral implant comprising at least one peripheral wall, at least a part of which, called posterior, comprises at least one straight passage of suitable dimensions to receive at least one anchoring device comprising a curved plate, so as to allow the passage of this rigid anchoring device without deformation despite its curvature, this passage crossing implant from the periphery toward an upper or lower surface, along a rectilinear and oblique trajectory adapted to the curvature of anchoring device, inserted essentially in the pane of implant, so as to orient anchoring device in the direction of the vertebral endplate of one of the vertebra between which implant is designed to be implanted, characterized in that passage comprises at least one groove designed to receive at least one rib of anchoring device according to the invention.

According to another feature, passage comprises at least one stop comprising at least one stop surface oriented in the direction of the outside of implant and designed to cooperate with at least one retaining stop of anchoring device so that this retaining stop retains implant once anchoring device is anchored in a vertebra through passage.

According to another feature, the intervertebral implant comprises at least one withdrawal stop comprising at least one stop surface oriented essentially facing the anterior end of the anchoring device inserted in passage, this withdrawal stop cooperating with at least one flexible lug of anchoring device, in order to oppose the withdrawal of anchoring device from implant.

According to another feature, peripheral wall comprises at least one fastening means designed to cooperate with a gripping end of an instrument for implanting implant.

According to another feature, the peripheral wall comprises two passages each oriented toward one of the upper and lower surfaces of implant, so as to anchor anchoring device in each of the vertebrae between which implant is designed to be implanted.

According to another feature, the peripheral wall comprises, at a so-called anterior part, opposite the one comprising passage, at least one beveled portion, so as to facilitate the insertion of implant between the vertebrae.

Another goal of certain embodiments incorporating various technical features described in the present application is to alleviate one or more of said (and/or other) disadvantages of the prior art by proposing an instrument for implanting intervertebral implants between vertebrae and implanting an anchoring device in at least one of these vertebrae, which allows implanting the implants substantially in the plane of the intervertebral space and implanting an anchoring device along an axis of approach substantially in the plane of the intervertebral space.

This goal is attained, for example, by an instrumentation for implanting intervertebral implant between the vertebrae and implanting at least one anchoring device in at least one of these vertebrae, the instrument comprising, on the one hand, at least one impactor comprising a head of suitable shape and size to press anchoring device and, on the other hand, at least one guide of a shape elongated along a longitudinal axis extending between a first end, called gripping, of implant, and a second end, called presser, the gripping end comprising at least one gripping means designed to cooperate with at least one fastening means of implant, characterized in that guide comprises a head of suitable shape and size to receive head of the impactor at least partially and comprising at least one guide surface having at least one radius of curvature essentially identical to at least one radius of curvature of anchoring device according to the invention, so as to guide this anchoring device through a passage of an implant according to the invention, for compacting anchoring device in a vertebral endplate of one of the vertebrae between which implant is designed to be implanted, head being made so as to allow the passage and/or guidance of rib of anchoring device.

According to another feature, head comprises at least one groove made for the passage of rib of anchoring device.

According to another feature, head of guide comprises a cavity of suitable shape and size to receive anchoring device and at least partially receive head of impactor, guide surface comprising at least two curved grooves each situated on either side of this cavity to guide the lateral sides of anchoring device on both sides of body, head of impactor penetrating into cavity from end to the other of these grooves.

According to another feature, shaft comprises a threaded end cooperating with a complementary threading of recess to affix implant when the shaft is activated by handle.

According to another feature, fastening means comprises a recess and that gripping means comprises an end of a shaft sliding in a body of guide when it is activated by a handle to enter and leave recess of implant.

According to another feature, fastening means comprise recess and a groove on a lateral side of peripheral wall, gripping means comprising one end of a shaft sliding in a body of guide when it is activated by a handle in order to enter and leave recess of implant and a lug made to be engaged in groove and serving as a lever arm for positioning implant 2) between the vertebrae.

According to another feature, groove comprises a recess designed to receive a stud of lug so as to improve the grip of implant by the instrument.

According to another feature, said groove created for passage of rib of anchoring device is created on at least a part of the upper wall and/or the lower wall of cavity of head of guide.

Other purposes of various embodiments incorporating various features described in the present application are to overcome some drawbacks of the prior art and can be related to the problems mentioned above.

This purpose is reached, for example by a device for anchoring intervertebral implant in the vertebrae, comprising a body comprising at least one straight plate elongated along a longitudinal axis extending between a first end, called anterior, designed to penetrate into a vertebra and a second end, called posterior, anchoring device being designed to be inserted through a passage crossing at least a portion of implant, in order to penetrate into at least one vertebral endplate and affix implant in this vertebral endplate by means of a stop retaining the implant, characterized in that the body comprises at least one longitudinal rib on at least a part of at least one of its faces, said rib being designed to cooperate with at least one groove in the passage of implant This purpose is reached, for example by a device for anchoring intervertebral implant in the vertebrae, comprising a body comprising at least one plate elongated along a longitudinal axis extending between a first end, called anterior, designed to penetrate into a vertebra and a second end, called posterior, anchoring device being designed to be inserted through a passage crossing at least a portion of implant, in order to penetrate into at least one vertebral endplate and affix implant in this vertebral endplate by means of a stop retaining the implant, characterized in that the body comprises at least one thickened portion and/or at least one plane surface arranged for providing a contact with the inner wall of the passage in the implant and stabilize the anchoring device in the implant.

This purpose is reached, for example by a device for anchoring intervertebral implant in the vertebrae, comprising a body comprising at least one curved plate elongated along a longitudinal axis extending between a first end, called anterior, designed to penetrate into a vertebra and a second end, called posterior, anchoring device being designed to be inserted through a passage crossing at least a portion of implant, in order to penetrate into at least one vertebral endplate and affix implant in this vertebral endplate by means of a stop retaining the implant, characterized in that the curvature of the plate is oriented along the width of the plate.

This purpose is reached, for example by a device for anchoring intervertebral implant in the vertebrae, comprising a body comprising at least one plate elongated along a longitudinal axis extending between a first end, called anterior, designed to penetrate into a vertebra and a second end, called posterior, anchoring device being designed to be inserted through a passage crossing at least a portion of implant, in order to penetrate into at least one vertebral endplate and affix implant in this vertebral endplate by means of a stop retaining the implant, characterized in that it comprises at least one withdrawal stop opposing to the withdrawal of the anchoring device from the implant by contact with a complementary stop of the implant and comprises resources arranged for disengaging the withdrawal stop of the anchoring device from its complementray stop.

This purpose is reached, for example by an Intervertebral implant comprising at least one peripheral wall, at least a part of which, called posterior, comprises at least one passage of suitable dimensions to receive at least one anchoring device comprising at least one plate, this passage crossing implant from the periphery toward an upper or lower surface, along a trajectory adapted to the anchoring device, so as to orient anchoring device in the direction of the vertebral endplate of one of the vertebra between which implant is designed to be implanted, characterized in that the implant comprises at least one stop complementray to a withdrawal stop opposing to the withdrawal of the anchoring device from the implant and comprises resources arranged for disengaging the withdrawal stop of the anchoring device from the complementary stop in the implant.

This purpose is reached, for example by an Intervertebral implant comprising at least one peripheral wall, at least a part of which, called posterior, comprises at least one passage of suitable dimensions to receive at least one anchoring device comprising at least one plate, this passage crossing implant from the periphery toward an upper or lower surface, along a trajectory adapted to the anchoring device, so as to orient anchoring device in the direction of the vertebral endplate of one of the vertebra between which implant is designed to be implanted, characterized in that the implant comprises resources arranged for the withdrawal of the anchoring device.

This purpose is reached, for example by a system for anchoring intervertebral implant in the vertebrae, characterized in that it comprises two anchoring devices for anchoring an implant in vertebrae, each device having a body comprising at least one plate elongated along a longitudinal axis extending between a first end, called anterior, being designed to penetrate into a vertebra and a second end, called posterior, the anchoring devices being designed being designed to be inserted through a passage crossing at least a portion of implant, in order to penetrate into at least one vertebral endplate and affix implant in this vertebral endplate by means of a stop retaining the implant, characterized in that the first anchoring device comprising a stop called cooperation, comprising at least one stop surface oriented essentially facing the anterior end and the second anchoring device comprising a stop, called cooperation, comprising at least one stop surface oriented essentially in the direction facing the posterior end, these two cooperation stops being made so as to cooperate with each other.

According to another feature of the anchoring system, stop of the second anchoring device comprises a second stop surface, oriented essentially facing the anterior end, and the first device comprises a withdrawal stop positioned so that its posterior stop end comes into contact with the second stop surface of stop then serving to support the withdrawal stop, thus impeding the withdrawal of the first device retaining the second device once it is in place in implant.

According to another feature of the anchoring system, at least one of the anchoring device comprises resources arranged for disengaging the withdrawal stop from the second stop surface.

This purpose is reached, for example by an Intervertebral implant comprising at least one peripheral wall, at least a part of which, called posterior, comprises at least two passages of suitable dimensions to receive at least two anchoring devices of a system according to the invention, these passages crossing implant from the periphery toward an upper or lower surface, along a trajectory adapted to the anchoring device, so as to orient anchoring device in the direction of the vertebral endplate of one of the vertebra between which implant is designed to be implanted, characterized in that the implant comprises resources arranged for the withdrawal of the anchoring device via the cooperation stops.

This purpose is reached, for example by an Intervertebral implant comprising at least one peripheral wall, at least a part of which, called posterior, comprises at least two passages of suitable dimensions to receive at least two anchoring devices of a system according to the invention, these passages crossing implant from the periphery toward an upper or lower surface, along a trajectory adapted to the anchoring device, so as to orient anchoring device in the direction of the vertebral endplate of one of the vertebra between which implant is designed to be implanted, characterized in that the implant comprises resources arranged for disengaging the withdrawal stop of the anchoring device.

BRIEF DESCRIPTION OF THE SEVERAL VIEWS OF THE DRAWING

Other features and advantages of various embodiments of the present invention will appear more clearly upon reading the description below, made in reference to the attached drawings, in which:

FIGS. 7A and 7B show perspective views of one of various embodiments of an implant, respectively alone and provided with a pair of anchoring devices like those shown in perspective in FIG. 7E, and FIGS. 7C and 7D respectively show a top view and a sectional view along plane 7D-7D of FIG. 7C, of the implant of FIG. 7B provided with these anchoring devices.

FIGS. 16A, 16B, and 16C show, respectively, a profile view, a sectional view along plane 16B-16B of FIG. 16A, and a top view of one of various embodiments of an instrument comprising an impactor and a guide, with one of various embodiments of an implant shown attached in FIGS. 16A and 16B.

DETAILED DESCRIPTIONS

Figure 1:
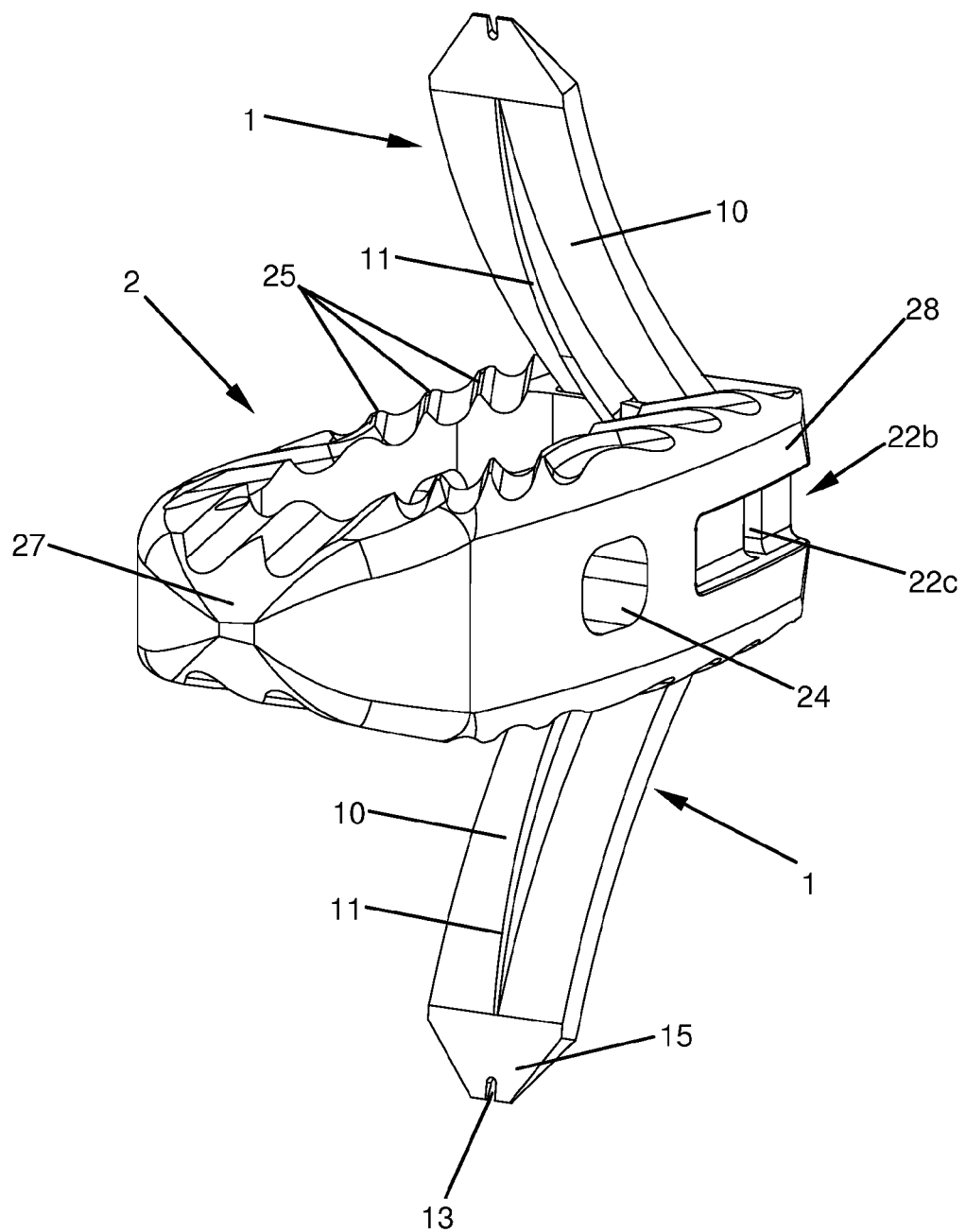
FIG. 1 shows a perspective view of an intervertebral implant provided with two anchoring devices according to one of various embodiments of the invention.

Various embodiments of the invention will now be described in reference to the figures of the present application. The invention simultaneously concerns three groups of objects:

- anchoring devices (1) (or "anchors"), and/or anchoring systems comprising plural anchoring devices (1) that may be identical, different, or complementary;
- intervertebral implants (2) configured for receiving one or more of such anchoring devices (1) or systems; and
- instruments (3, 4) for implanting implants (2) between the vertebrae and fixing implants with one or more anchoring devices (1) or anchoring systems.

Each group of objects may comprise various possible embodiments, relating to a given object. Each object comprises various elements (generally constituent of the object) characterized by at least one technical feature. Each object (of a given group) concerned by at least one technical feature might be associated with at least one other object (of the same or another group), for example with respect to at least one complementary technical feature, such that the groups of objects share a common inventive concept. The invention may thus also concern an ensemble comprising at least two of these objects, as well as each object individually. The elements (for example a plate, a lug, a stop, a raised portion, etc.) and their technical features (for example a curvature, a flexibility, a possible disengagement, a height, a stop surface, etc.) are described in more detail hereafter in the present application. At least one technical feature corresponding to an element of a given object solves at least one technical problem, in particular among those mentioned in the preamble of the present application. The present application thus describes various embodiments and configurations for each object or group of objects, by specifying at least one technical feature of at least one element. It will be understood from reading the present application that the various technical features of each element described in at least one embodiment or configuration may be isolated from other technical features of the object concerned by (or the objects concerned by and/or associated with) said embodiment or configuration (and thus concerning the same or another element) and/or may be combined with any other technical feature described herein, in various embodiments or configurations, unless explicitly stated otherwise, or unless these features are incompatible and/or their combination is not functional, in particular because the structural adaptations that may be required by such isolation or combination of features are directly derivable from the appreciation of the present disclosure. Similarly, although some technical features are discussed herein in reference to the anchor device, they may be incorporated in various embodiments of the anchoring systems. Generally speaking, the specific technical feature(s) concerning a given element shouldn't be considered as exclusive from those concerning another element, nor from other technical features concerning the same element, except if it clearly appears that the combination of these technical features is impossible or nonfunctional. Although the present application details various embodiments or configurations of the invention (including preferred embodiments), its spirit and scope shouldn't be restricted to the examples given.

Various embodiments of anchoring devices (1) in accordance with the present invention are usable with intervertebral implants (2), such as, for example, intersomatic cages or intervertebral disc prostheses. Intervertebral implants are designed to be implanted between two adjacent vertebrae of the vertebral column (spine) or to provide a junction between two vertebrae, at their periphery in the case of osteosynthesis plates (which can be used alone or in combination with an intersomatic cage). Anchoring device (1) is designed to be anchored in one of the vertebrae so as to attach the implant to this vertebra. Various embodiments of anchoring devices (1) according to the invention comprise at least one curved and rigid plate, configured for penetration into a vertebra through an implant and comprise at least one stop to hold this implant against this vertebra. The technical features of "curvature" and "rigidity" concerning the "plate" element of the "anchor" object are described in detail below. Device (1) for anchoring intervertebral implant (2) in the vertebrae will also be referred to in the present application by the term "anchor" (1), without introducing any limitation whatsoever. This type of anchor has been described in publications FR 2,916,956, US 2009/105832 and WO 2008/149223 of applications filed by the assignee of the present application, herein incorporated by reference in their entirety. In various embodiments, anchor (1) comprises a body including at least one curved plate (10) elongated along a longitudinal axis (L, FIGS. 13E and 14A). This longitudinal axis (L) of anchor (1) extends between a first end, which will be referred to as the anterior end, designed to penetrate into a vertebra, and a second end, which will be referred to as the posterior end. Note that the designations of the "posterior" and "anterior" ends of anchor (1), implant (2), and instrument (3, 4) are used in the present application in reference to the direction in which anchor (1) will be inserted. Thus for anchor (1), the first end (referred to as the anterior end) is the one designed to be inserted first and designed to penetrate into a vertebra to affix an implant. Concerning the implant, its wall or end denoted as "posterior" is the one comprising an opening of a passage for the insertion of the anchor, whether this wall is really posterior to the implant or not during deployment. Concerning the instrument, the anterior end is the one intended to be abutted on the implant for the insertion of the anchor within the passage. Certain embodiments of implants (2), including some described in detail in this disclosure and concerning an intersomatic cage, are made for lateral insertion into the disc space, and accordingly the posterior end will be positioned on a lateral side of the vertebrae, while the anterior end will be positioned near the medial line or on the opposite lateral slide. Nevertheless, the terms "anterior" and "posterior" will still be used since they are easier to understand from the point of view of implantation and may be commonly and conveniently used with reference to anchor (1), implant (2), and instrument (3, 4) regardless of the implantation approach (implantation path) chosen. Accordingly, the terms "anterior" and posterior" are not intended to refer simply with respect to a patient or an anatomical feature of a patient. It will be noted as well that reference is made herein to a longitudinal axis (L) between these two ends and that this longitudinal axis (L) therefore corresponds to a anteroposterior axis of anchor (1), implant (2), and instrument (3, 4), still in reference to the direction of insertion of the anchor (1). It will also be noted that the term "substantially" is used several times in the present description, in particular concerning a technical feature such as an orientation or a direction, so as to indicate that the feature concerned may in fact be slightly different and not exactly as stated (for example, the expression "substantially perpendicular" should be interpreted as "at least approximately perpendicular" because it may be possible to choose an orientation which is not exactly perpendicular for allowing however to serve substantially the same function). Furthermore, the term "substantially" used in the present application may also be interpreted as defining that the technical feature may "in general" ("generally"), and often "preferably", as stated, but that other embodiments or configurations may be within the scope of the present invention.

The fact that anchor (1) may comprise at least one plate (10) allows anchor (1) to ensure a good hold, at least in a direction substantially perpendicular to the plate, since the width of the plate offers a surface opposing movement of the anchor and thus of the implant (perpendicularly to this surface) in the bone tissue in which it is implanted. It will be noted that when the plate is curved, this hold is created along at least one direction substantially radial to the radius of curvature of the plate. In fact, various embodiments of the present invention, like various embodiments of the one described in the applications cited above, have the advantage of a having curvature that allows it to be implanted in the vertebral endplate of a vertebra along an approach axis substantially perpendicular to the axis of the spine at the level of the vertebrae between which the implant is implanted (or in the plane of the intervertebral space), which may facilitate implantation and allow avoiding some of the disadvantages linked to the encumbrance (dimensions) of the approach to the vertebrae. On the other hand, in various embodiments the anchor advantageously has the shape of a plate which may be relatively thin, facilitating the penetration of anchor (1) into the bone tissue. This thinness of plate (10) may pose a problem of stability of anchor (1) in the vertebra, to the extent that the plate might form a sort of blade that can split the vertebra in a direction along the width of the plate (transversely to longitudinal axis (L) of various embodiments), notably during its impaction in the vertebra, or later, due to the significant stress applied thereon when the patient moves, for example. Furthermore, this thinness may diminish the rigidity of the plate. In some applications rigidity may be an important feature for effective fixation, resulting in embodiments particularly more effective than staples or other thin and/or relatively flexible, often fragile, devices, which do not allow a good hold due to their flexibility and/or thinness and/or their fragility. Therefore, rigid anchors are preferred for many embodiments (curved anchors being also preferred, but for facilitating the approach to vertebrae), instead of deformable anchors. Rigid anchors penetrate into the vertebrae through a passage (21) crossing at least a part of the implant without being deformed in this passage (21). For these rigid embodiments, inner walls (210) of this passage (21) in the implant preferably have shapes and dimensions that allow the anchor to pass: either by a curvature complementary to that of the anchor, or by an uncurved shape with a height slightly greater than that of the anchor to permit its passage despite its curvature and rigidity (thus avoiding machining a curved passage in the implant, which may be complex and costly).

Various embodiments of the present invention resolve problems of stability and rigidity of anchor (1) by using at least one longitudinal rib (11) over at least one part of at least one of the faces of the body of anchor (1). This longitudinal rib (11) preferably is orientated in the direction of the length of plate (10), substantially parallel to longitudinal axis (L) in various embodiments. Note that the present invention foresees various configurations of anchor (1) with regard to the direction of its curvature. By referring again to the direction of insertion of the anchor, it is understood that various embodiments of the anchor are designed to penetrate from the periphery of the disc space into the vertebrae, preferably into the inferior vertebral endplate of the upper vertebra or into the superior vertebral endplate of the lower vertebra, in particular in the case of implants such as intersomatic cages or intervertebral disc prosthesis. Also, other embodiments of the anchor may be configured for implantation preferably into the periphery of the vertebral body near the intervertebral space, especially in the case of intervertebral implants such as osteosynthesis plates. When an anchor is intended for implantation into the vertebral plate, for example through implants such as intersomatic cages or intervertebral disc prosthesis, the curvature of the anchor is preferably configured so that, once embedded in a vertebra, the axis of the spine is substantially tangential to a substantial part of its anterior extremity, or at least that this part of the anterior end forms a small (or slight) angle with the vertical axis of the spine.

The invention also foresees various embodiments of anchors (and thus also of the implants and instruments that may be associated therewith) in which the width of the plate (10) of anchor (1) is oriented substantially along this vertical axis of the spine and other embodiments of anchors (and thus also of the implants and instruments that may be associated therewith) in which the width of the plate (10) of anchor (1) is oriented substantially perpendicularly to this vertical axis of the spine, i.e., generally horizontally. Thus, in certain embodiments, the curvature of plate (10) of anchor (1) may be oriented in the width of plate (10), as shown, in particular, in FIGS. 13D-13G and as indicated by FIGS. 3B, 3K, 4A, and 13A-C. These particular embodiments of the anchor preferably, in particular in the case of implants intended for implantation through an anterior anatomic pathway, include at least one rib (11), which allows stabilizing the anchoring device and helps prevent it from damaging the vertebrae too much. In the absence of such a rib, it would not be preferable to orientate the curvature in this direction, because the implants implanted through an anterior anatomical path (substantially sagittal or para-sagittal), will be affixed by an anchor along this same direction while the strongest constraints that are exerted on the implants are oriented in this same direction (sagittal or para-sagittal). Conversely, for implants (such as cages or implants, for example) intended for implantation by a lateral path to have, this curvature oriented along the width of the plate (10) of anchor (1) is preferable and may not need a rib (11) because the plane of the plate is configured to be substantially perpendicular to the sagittal axis (or para-sagittal) of the spine and therefore opposed to the strongest constraints exerted on the implant and anchor. It will thus be understood that particularly when the plane of the plate is configured to be substantially perpendicular to the axis along which the strongest constraints are exerted, depending on the anatomical implantation's pathway, it is possible not to have rib (11) on the anchor (1), nor corresponding grooves (211, 3011) in associated implants and instruments. Thus, the present application foresees various embodiments of anchors (1) comprising no rib (11), particularly for configurations in which the curvature of the anchor (1) is configured as a function of the anatomical implantation path so that the plate (10) can ideally oppose to the strongest constraints when the implant and anchor are in place in the patient, and in particular anchors (1) curved along the width of the plate for implants with a lateral anatomic implantation path. The implants and instruments that may be associated with such anchors need not comprise grooves (211, 3011). These particular objects may or may not also include any technical feature (or combination of technical features) described for any element (or combination of elements) of any object (or combination of objects) disclosed in this application, as long as they are not incompatible, in particular because the structural adaptations that may be required by such isolation or combination of features are directly derivable from the appreciation of the present disclosure. Note that the curvature of the anchor along the width of the plate (10) allows referring to two lateral faces, and to a concave side (or edge) (inside the curve) and a convex side (or edge) (outside the curve) of anchor (1).

Figure 2A:
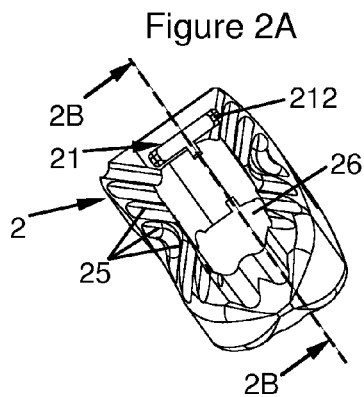
FIGS. 2A, 2B, and 2D respectively show a perspective view from the front, a sectional view along plane 2B-2B of FIG. 2A, and a perspective view from the rear, of one of various embodiments of an intervertebral implant alone, FIGS. 2C, 2E, and 2F respectively show a perspective view from the rear, a top view, and a sectional view along plane 2F-2F of FIG. 2E, of the same implant provided with two anchoring devices.
Figure 2B:
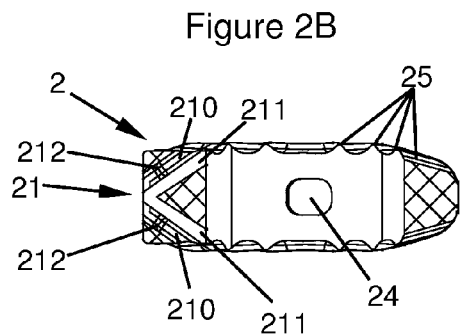
Figure 2C:
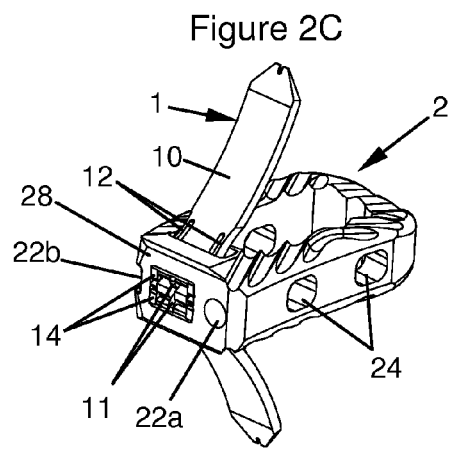
FIGS. 2G and 2H show two of various embodiments of anchoring devices that can be used with the implants of FIGS. 2A to 2F.
Figure 2D:
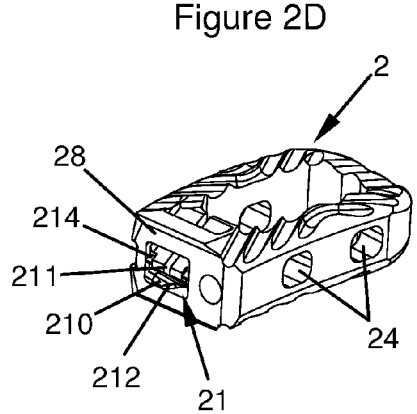
Figure 2E:
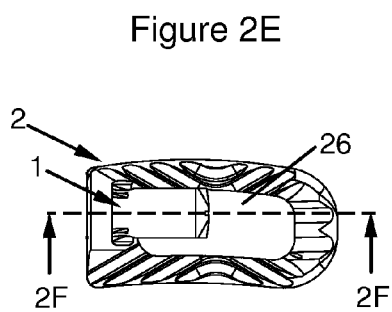
Figure 2F:
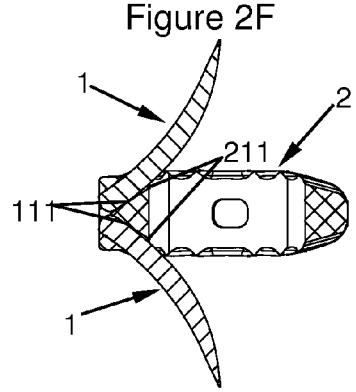
Figure 2G:
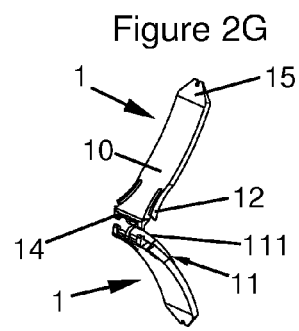
Figure 2H:
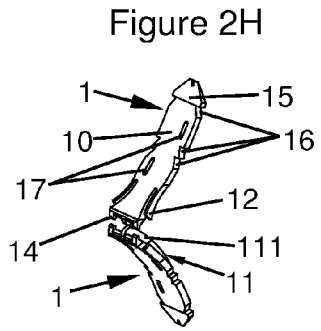
Figure 3A:
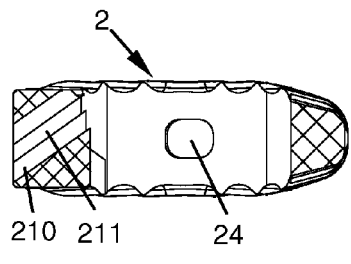
FIGS. 3A and 3C show sectional views of the implant of FIGS. 3B, FIGS. 3D and 3F show sectional views of the implant of FIG. 3E, FIGS. 3G and 3I show sectional views of the implant of FIG. 3H, and FIGS. 3J and 3L show sectional views of the implant of FIG. 3K.
Figure 3B:
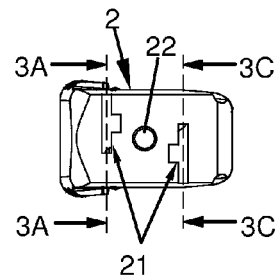
FIGS. 3B, 3E, 3H, and 3K show rear views of four of various embodiments of intervertebral implants and the cutting planes for associated sectional views.
Figure 3C:
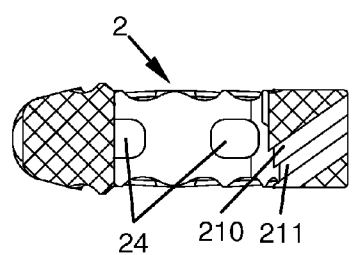
Figure 3D:
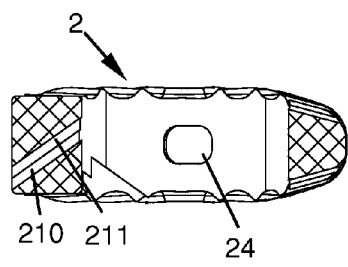
Figure 3E:
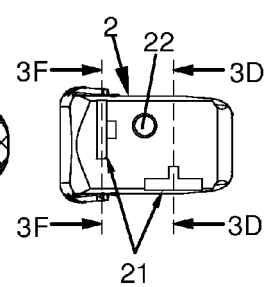
Figure 3F:
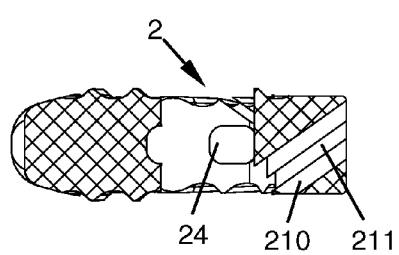
Figure 3G:
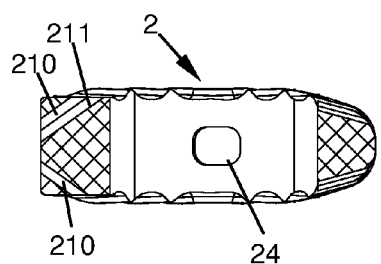

In other embodiments of anchors (and thus also of the implants and instruments that may be associated therewith), for example, as shown by FIGS. 2G and 2H, the curvature of plate (10) is oriented in the depth (or height, thickness) of the plate. Note that the curvature of the anchor in this orientation allows referring to a concave face (inside the curve) and a convex face (outside the curve) of anchor (1), as well as two lateral sides (or edges) of the anchor (1). Note that the invention also foresees combinations of various objects described in the present application, by the incorporation of various technical features of anchors (1) and/or implants (2) and/or instruments (3, 4). For example, FIG. 3E shows a "mixed" implant (2) provided with two types of passages (21) each designed to receive an anchor having a different curvature orientation. Note also that longitudinal axis (L) is shown for different variants of curvature in FIGS. 13E and 14A.

Figure 3H:
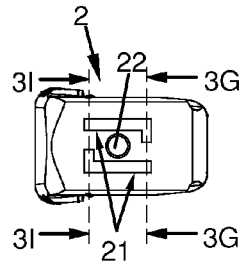
Figure 3I:
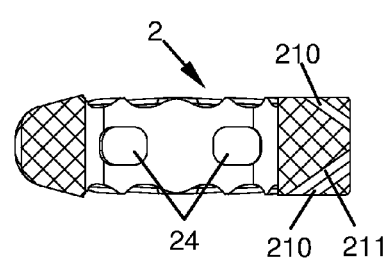
Figure 3J:
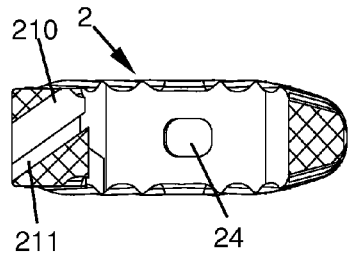
Figure 3K:
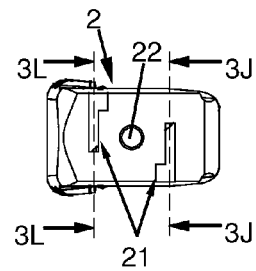
Figure 3L:
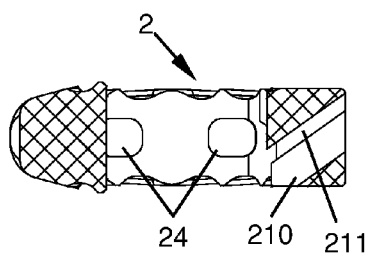
Figure 4A:
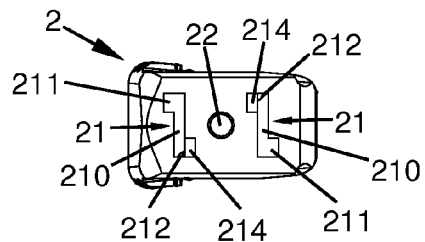
FIGS. 4A, 4B, 4C, 4D, 4E, 4F, 4G, and 4H show rear views of 8 of the various embodiments of an intervertebral implant, revealing the profiles of several of various embodiments of anchoring devices that may be used to secure them to vertebrae.
Figure 4B:
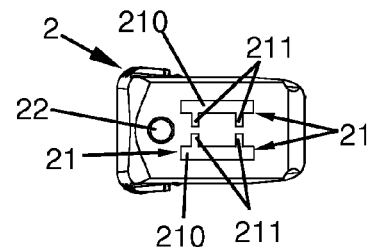
Figure 4C:
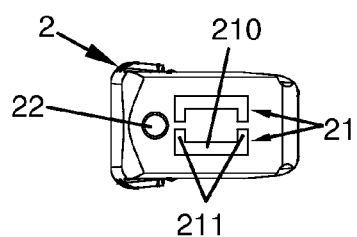
Figure 4D:
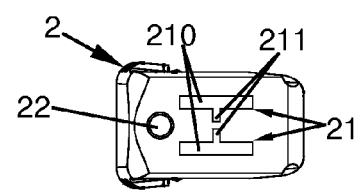
Figure 4E:
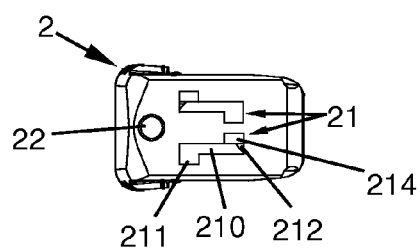
Figure 4F:
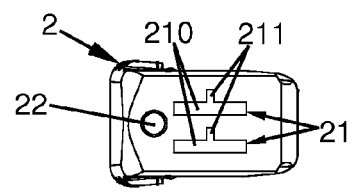
Figure 4G:
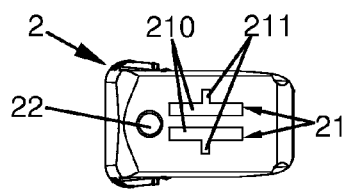
Figure 4H:
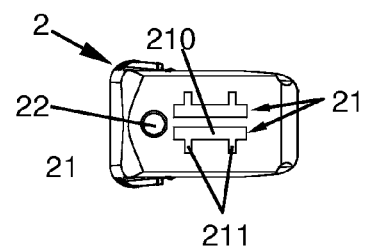
Figure 5A:
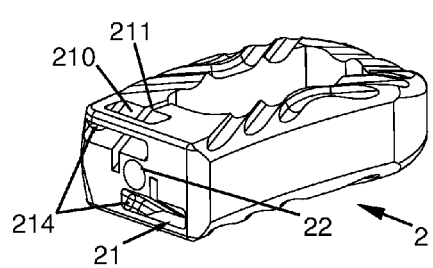
FIGS. 5A, 5B, and 5C show perspective views of 3 of various embodiments of an intervertebral implant.
Figure 5B:
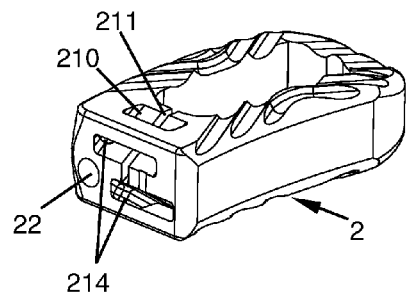
Figure 5C:
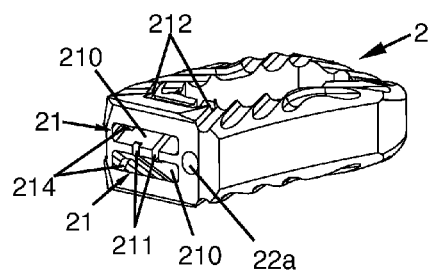
Figure 5D:
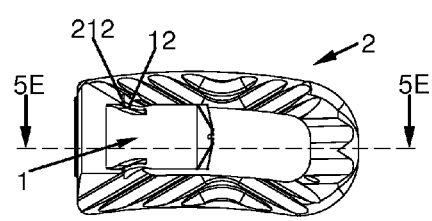
FIG. 5D shows a top view of the implant of FIG. 5C provided with two anchoring devices such as those shown in perspective in FIG. 5F.
Figure 5E:
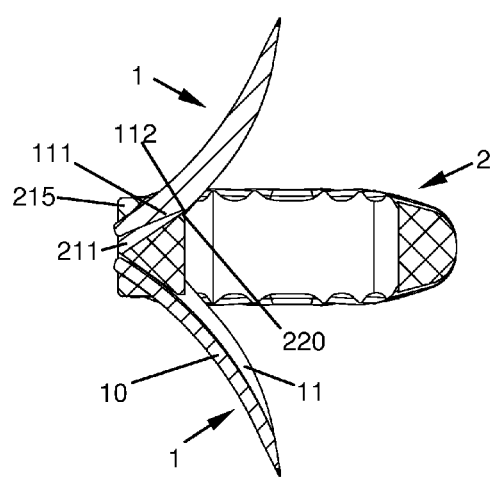
FIG. 5E shows a sectional view of this implant and the anchors along plane 5E-5E of FIG. 5D, FIGS. 6A, 6B, 6C, 6D, 6E, 6F, and 6G show, respectively, 3 sectional views and 4 perspective views of 7 of various embodiments of an anchoring device.
Figure 5F:
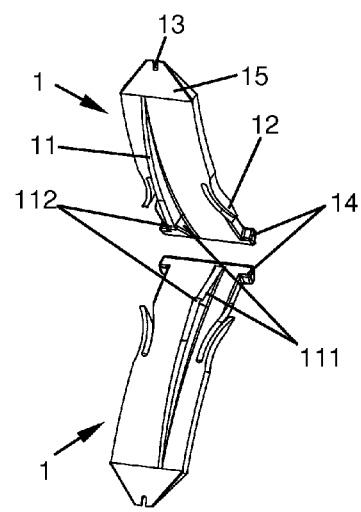

It will be noted also that the invention foresees various embodiments of anchors (and thus also of the implants and instruments that may be associated therewith) with regard to the position and length of rib (11). Generally, rib (11) preferably is designed at least to inhibit (or prevent) the anchor (1) (and thus also the implant) from moving transversely with respect to the vertebra. The rib (11) may also be configured and deployed to improve the rigidity of the anchor (1). Thus it is generally preferable for the rib to be present on a part of anchor (1) that extends outside the implant (2) when fully inserted therein. The rib can, but need not, extend up to the anterior end, and thus can stop nearby or at a given distance from this anterior end. Also, it is not generally necessary that the rib extend up to or near the posterior end that is designed to remain in the implant. When the rib extends up to or near the posterior end, however, it may allow further stabilization of the anchor in the implant (for example, by means of its cooperation with groove (211) in the passage). Although various preferred embodiments of the anchor have at least one rib (11) on at least one part of at least one of the faces of anchor (1), the invention foresees numerous other embodiments, of which some of the diverse examples are shown in the figures and/or discussed elsewhere herein. In the majority of figures showing anchors whose curvature is oriented in the direction of the depth of plate (10), the rib is positioned on the convex face (see, for example, FIGS. 2G and 2H). However, in certain embodiments, at least one rib (11) may be provided on the concave face as shown, for example, in FIGS. 14C, 14D, and 14E. In other embodiments, at least one rib may be provided on each of the faces of the anchor, as shown, for example, in FIGS. 14F, 14G, and 14H. Likewise, various illustrative and non-limiting examples of implants (2) designed to receive various types of anchors (1) are shown, for example, in FIG. 3(A to L) and FIG. 4(A to H). These figures show the profile that the entrance to the passage has, and the preferable rib configuration of the anchor that will be associated with it. In addition, FIGS. 3A, 3C, 3D, 3F, 3G, 3I, 3J, and 3L show sectional views of implants showing the shape of passages (21) in the implants, which generally will be a function of the types of anchors preferably used with those implants. For example, FIG. 3B shows an implant (2) with which 2 anchors (1) will be associated, each anchor having a vertical orientation (anchor curved in the direction of the plate width), while FIG. 3E shows a "mixed" implant (2) with which 1 anchor (1) with vertical orientation and 1 anchor with horizontal orientation (anchor curved in the direction of the plate depth) will be associated. FIG. 3H shows an implant (2) with which 2 anchors (1) will be associated with horizontal orientation with each having a rib (11) on the convex face, and FIG. 3K shows an implant (2) with which 2 anchors (1) will be associated with vertical orientation, with each having a rib situated on a lateral face toward the inside of the implant. FIG. 4A shows an implant (2) with which 2 anchors (1) will be associated with vertical orientation, with each having a rib (11) on a lateral face toward the outside of the implant. As discussed elsewhere in this disclosure, anchors (1) which will be associated with the implants of FIGS. 4A and 4E will comprise a retaining stop (14) on the face opposite the one with the rib (11), said retaining stop (14) being arranged for cooperating with a stop (214) of the implant shown on these figures. FIGS. 4B and 4C each show an implant (2) with which 2 anchors (1) will be associated, each anchor (1) having a horizontal orientation and 2 ribs (11) on the convex face (somewhat offset toward the lateral sides from one figure to the other). FIG. 4D shows an implant (2) with which 2 anchors (1) will be associated, each anchor (1) having horizontal orientation and a single rib (11) on the convex face (central for FIG. 4D and off-center for FIG. 4E). FIGS. 4E and 4F each shows an implant (2) with which 2 anchors (1) will be associated with horizontal orientation, one of which will have a single rib (11) on the convex face while the other will have a single rib (11) on the concave face (a central ribs for FIG. 4F and offset ribs for FIG. 4E). FIG. 4G shows an implant (2) with which 2 anchors (1) will be associated, each anchor (1) having horizontal orientation and a single rib (11) centered on the concave face. FIG. 4H shows an implant (2) with which 2 anchors (1) will be associated, each anchor having a horizontal orientation and two ribs (11) on the concave face. Anchors (1) with off-center ribs (such as the ones shown, for example, in FIG. 5F) permit reducing the size required for the presence of two passages (21) in implants (2), as is especially visible in the examples of FIGS. 5A, 5B, and 5C. In various embodiments of implants, the use of off-center ribs avoids having 2 aligned grooves (211) such as shown in FIG. 4D, which could make the implant fragile, and may thus allow either having intersomatic cages with a relatively small height if the configuration of the spine requires it, or keeping more material above (and/or below) the passage to provide a stronger implant or arranging a central attachment (22) resource (possibly larger than in other configurations) as particularly visible on FIG. 5A. These illustrative and non-limiting examples demonstrate that the various objects of the invention are not limited regarding the number or positions of the anchors, nor the number or positions of their rib(s), although certain configurations are particularly advantageous, notably in terms of resistance or size of the implant (for example, in the case of the cervical implant, where the small size places strong constraints on the size and where the strength of the materials requires that the implants not be made excessively fragile by passages (21), especially in the case of intersomatic cages made of PEEK (polyether ether ketone).

In various anchor and anchor system embodiments of the invention, plate (10) can be substantially rectangular, as is shown in many of the figures, but can, of course, have various other shapes without departing from the spirit of the invention. Preferably, whatever the shape of the periphery of the plate, it presents at least one surface of sufficient dimension for efficiently opposing its movements in the vertebra, contrarily to staples, nails or other known devices. For example, most of the plates shown in the figures have a substantially rectangular periphery, but have variations in shape described in detail in the present application. Moreover, anchor (1) can comprise several plates, and/or a single plate of the body can have various shapes without departing from the spirit of the invention. In fact, to the extent that the desired hold can be obtained by at least one plate offering at least one surface sufficient in the dimension described here as the width of the plate, the anchor can comprise plates having a substantially trapezoidal or triangular periphery or having diverse shape variations. For example, in certain variants of anchor (1) (not shown), the body of anchoring device (1) may have two plates substantially parallel to one another (and/or with substantially the same curvature) and connected together at the posterior end, for example, such as described in publications FR 2,827,156 (and WO 03/005939 and US 2004/0199254) and FR 2,879,436 (and WO 2006/120505 and US 2006/0136063), each of which is incorporated herein by reference, which may form a stop holding anchor (1) on the implant and thus holding the implant against the vertebra. In addition, as discussed elsewhere in this disclosure, various embodiments of anchors (1) may comprise at least one straight plate, for example such as described in these publications, or comprise 2 straight plates connected by a link able to, or arranged to, form a stop allowing to affix the implant. Generally, various anchor embodiments of the invention may use a rib (11) to provide a good hold perpendicular to the width of the plate, and such a rib may, in fact, be formed by at least one fin or at least one similar structure (or several structures), to improve the rigidity of the anchor and offer a surface opposing transverse movement of the anchor in the bone tissue. Various embodiments of anchors are also foreseen with respect to the technical features of the dimensions, in particular the height, of the rib, which is preferably arranged for opposing to this transverse movement. The height of the rib (11) may for example be approximately half of the width of the plate (10) of anchor (1), so as to form itself a second plate particularly efficient in its stabilizing function.

Various embodiments of the invention strive to reduce the size of the devices and associated instruments, so as to allow implanting the anchoring device along an axis substantially in the plane of the intervertebral space (disc space). As described in publications of applications FR 2,916,956, US 2009/105832, and WO 2008/149223 cited above and incorporated herein by reference, curved plate (10) describes, along the longitudinal axis, at least one arc of a circle and/or at least one arc of an ellipse whose dimensions and radii of curvature are created so that anchoring device (1) can be implanted in the vertebral endplate of a vertebra by having its perpendicular axis substantially in the plane of the intervertebral space, i.e., along an axis of approach substantially perpendicular to the axis of the spine (i.e., said plane or said approach axis being substantially tangential to at least part of the anterior end when the anchor approaches the vertebrae). Similarly to the above cited applications, various embodiments of the various objects of the present invention concern the technical feature of the radius (or radii) of curvature of anchoring device (1). Various embodiments of anchoring device (1) in fact have a different radius of curvature from one anchor to another, and/or several different radii of curvature on different portions of the body of a given anchor (1). Thus, for example, the body of anchor (1) may have an arc of a circle or arc of an ellipse shape, but it may also describe a more complex curvature, as if several arc(s) of a circle, having a same radius of curvature or different radii of curvature, were placed end to end or if several arc(s) of an ellipse, having a same radius of curvature or different radii of curvature, were placed end to end, or any combination of arcs of a circle or ellipse or even a radius of curvature that varies along the body. In the present description, the terms "arc of a circle" or "radius of curvature" encompass all these different possibilities. Thus, various embodiments of the present invention provide different variants concerning the radius of curvature and certain related aspects of anchoring device (1), as well as implants (2) and instruments (3, 4) that may be associated with it. In fact, for example, depending on the use of device (1) and in particular its intended implantation location along the spine, it may be preferable to have a larger or smaller radius of curvature. Depending on the radius of curvature of anchoring device (1), the axes passing, respectively, through the penetration end and the stop end of device (1) form an angle, typically comprised between approximately 90° and 180°, although it may also be chosen to be less than 90°. Preferably, this angle will be comprised between 110° and 160°, which, in many circumstances, will facilitate implanting the device better than an angle outside these values. According to the fixation that one wishes to obtain by means of anchoring device (1), the angle will be selected to be more or less open. If one wishes, for example, to promote tight affixation of the cage or the prosthesis against the vertebral endplate, an angle comprised between 120° and 180° may be preferred, while if one wishes rather to prevent the implant from moving in the plane of the disc space, an angle comprised between 90° and 150° may be preferred. Although these angle variations are not shown in the figures, different angles for anchoring device (1) permit covering the different desirable types of anchoring in order to assure a fixation of the implants that is adapted to the case. A device (1) whose angle is at an optimal value, for example near 135°, can also be provided in one of the preferred embodiments for fixation of the device both by pressing the implant tight against the vertebral endplates and preventing it from moving in the plane of the disc space. Moreover, according to the various embodiments of implant (2), different angles can be chosen for the device, particularly to permit a good fixation despite possible lordosis, kyphosis, or even scoliosis, whether it be natural, pathological, or imposed by the implant. Thus, various embodiments of anchoring device (1) and of implant (2), by means of its radius of curvature and the orientation of passage (21) into which it will be inserted, can be implanted along an axis of approach substantially in the plane of the intervertebral space, i.e., the plane in which implant (2) is implanted, which facilitates the approach of all the elements of the implant and the device to the intervertebral space. In one embodiment, the arc (or arcs) described by the body of anchor (1) has (or have) dimensions and at least one radius of curvature so that anchoring device (1) can be implanted in a vertebral endplate along an axis of approach forming an angle comprised between 40° and 140° with the vertical axis of the spine and, preferably, an approximately 90° angle. This angle can vary for a same anchoring device (1) depending on the dimensions of the approaches to the vertebra and can also vary from one anchoring device (1) to the other depending on the radius of curvature of device (1) used (and therefore the angle formed between its anterior and posterior ends). Furthermore, this present application also describes various embodiments of anchor (1) in which the body comprises at least one straight (uncurved) plate (10). Note that in the case of straight anchors (1) (i.e., comprising at least one straight plate), the approach axis may preferably not be substantially in the plane of the disc space but may be oblique. This type of oblique axis is not generally preferred because of the encumbrance of the access to vertebrae but it is still possible to use in some circumstances. The implants (2) used with such straight anchors (1) preferably comprise at least one straight passage (21), oriented toward at least one vertebra, along an oblique path (not perpendicular to the axis of the spine) between the periphery of the spine and the vertebrae. The instrumentation used with such implants (2) with straight passages and such straight anchors (1) preferably will have a contact surface with the implant, at the anterior end, inclined with respect to its longitudinal axis (antero-posterior according to the convention used in the present application), so as to allow an oblique approach axis relative to the vertebrae. The grooves (3011) in the head (30) of the guide (3) preferably will be straight, so as to guide the straight anchor (1), and arranged for bringing the anchor facing the entrance of the straight passage (21) in the implant. Furthermore, various embodiments of anchor (1) may also have a body comprising at least two straight plates (10) (or plate portions) forming an angle between each other. These straight plates (10) (or plate portions) may for example be linked by at least one connective portion forming such angle (for example thanks to a curvature of this connective portion). These various embodiments may for example be used in association with implants (2) comprising a curved passage (21), for example so as to facilitate the passage of anchor (1) and/or assure a minimum play of anchor (1) within the implant (2), thanks to contact of various parts or portions of the anchor (1) with various parts or portions of inner walls of the passage (21). Various embodiments of anchor (1) may also have a body comprising at least one straight plate (10) (or plate portion) and at least one curved plate (10) (or plate portion). These various configurations of the body of anchor (1) allow providing various embodiments of potential objects of the invention, concerning anchors comprising various portions. These particular objects can be configured to solve the problem(s) of facilitating the passage of anchor (1) through the implant (2) and/or to improve the stability of anchor (1) within the implant (2). In the case where such objects do not comprise rib (11), the implants and instruments that may be associated therewith may not comprise grooves (211, 3011). These particular objects (i.e., any of these embodiments comprising at least one straight and/or curved plate (or plate portion) in their body) may also comprise or not, according to various embodiments, any technical feature (or combination of technical features) described for any element (or combination of elements) of any object (or combination of objects) disclosed in this application, as long as they are not incompatible, in particular because the structural adaptations that may be required by such isolation or combination of features are directly derivable from the appreciation of the present disclosure.

Anchoring device (1) generally cooperates with at least one passage (21) crossing through a portion of the implant that it is intended to affix. Such a passage can be a conduit or a channel, for example, of shapes and sizes arranged for the passage of the anchoring device, particularly in cross-section (for example, a substantially rectangular cross-section with rounded angles). Preferably, passage (21) is straight, so as to facilitate its machining, and its dimensions are arranged for the passage of a curved and rigid anchoring device (1) without requiring deformation of this device regardless of its radius of curvature. In various embodiments in which anchor (1) is curved, the height (of the opening) of the passage is therefore preferably slightly greater than the thickness of anchoring device (1), sufficiently to allow the passage of this device inside passage (21), without deformation regardless of its curvature and its rigidity, but sufficiently small to assure a good retention of implant (2) by anchoring device (1), without too much play of the device inside passage (21). In certain embodiments of the invention, the width of passage (21) can be substantially equal to the width of device (1) so that this device has little or no lateral play once it is inserted into passage (21). The length of anchoring device (1) may be adapted to the length of passage (21) to be crossed and the depth to which it must penetrate in the vertebral endplates.

Rib (11) generally enhances the rigidity of anchor (1) and inhibits damage to the vertebrae from "cutting" in the direction of the width of anchor (1). To inhibit this movement in the direction of the width of the anchor, hereinafter designated "transverse" for simplicity (it is transversal to the length of the anchor), rib (11) preferably will have a sufficient height for effective interlocking, by offering a sufficiently large surface to hold the anchor transversely. Thus, rib (11) forms a sort of fin inhibiting the anchor from cutting the vertebra by transverse movements, which enhances fixation into the vertebra. Furthermore, increasing the rigidity of anchor (1) generally tends to strengthen its fixation in the vertebrae: the plate usually will not twist or bent, thus presenting less risk of ejection from the vertebra. Various embodiments of anchor (1) comprising at least one rib therefore offer a good hold in 2 planes, instead of only one in the absence of such a rib (11).

Figure 18A:
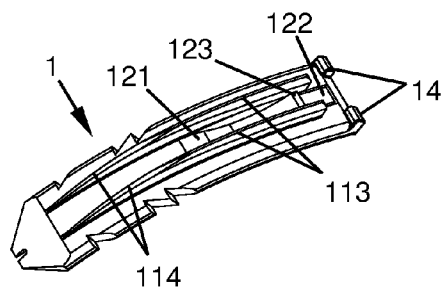
FIGS. 18A and 18B are perspective views, respectively from above and below, of one of various embodiments of an anchoring device, FIGS. 18C and 18D respectively represent a top view and section view along the plane 18D-18D of FIG. 18C of one of various embodiments of an implant fitted with such anchoring devices.

In various embodiments of anchoring devices (and eventually of implant and/or instrument which may be associated therewith), the width and/or the height of the rib (11) can vary along the longitudinal axis of body (10). Thus, for example, as some of the figures show, rib (11) starts to project near the anterior end of the anchor and its height increases progressively toward the posterior end. This height of rib (11) can be constant over a given part, for example near the posterior end, or can vary along the entire length. Moreover, in order to facilitate the penetration of rib (11) into the bone tissue, the peak of rib (11), i.e. its upper part (the one opposite the plate), can be sharpened over at least a part, for example near the anterior end. For example, the rib can have chamfers on its lateral sides. In the example of FIG. 18A, the anchor (1) comprises two ribs (11) on its convex face, each rib comprising a chamfered portion (113) and a plane portion (114). In this example, the chamfered portion (113) is located close to the posterior end and the implant can thus comprise grooves which depth has a shape complementary to this chamfered portion (113), while portion (114) is planar close to the anterior end. It will be understood that it is possible to inverse this configuration, in particular for having a sharpening of the chamfered portion (113) at the anterior end, so as to facilitate the penetration into the vertebrae, or provide diverse configurations with several different portions. Likewise, the width of the rib (in the direction of the width of the plate) can also vary, for example becoming thicker toward the posterior end, either by this sharpening of the anterior end, or by a pronounced thickening of the posterior end of the rib forming a structure for stabilizing anchor (1) in implant (2), like the ones that are described elsewhere in this disclosure.

Generally, as previously mentioned, anchoring device (1) is designed to be inserted through a passage (21) crossing at least a portion of implant (2), in order to penetrate into at least one vertebral endplate and affix implant (2) onto this vertebral endplate by means of at least one stop holding the implant. Longitudinal rib(s) (11) is (are) therefore designed to cooperate with at least one groove (211) created in passage (21) of implant (2). This cooperation between rib (11), forming a sort of guiding fin, with groove (211) in passage (21), can be configured to strengthen the fixation of anchor (1) in implant (2), notably by reducing the transverse play of the anchor (in the direction of the plate width). Increasing the height of this rib between the anterior end and the posterior end, combined with the constancy of this height near the posterior end, as can be seen especially in FIGS. 6A to 6G, for example, can facilitate the penetration of the rib into the bone and provide a posterior end of constant size stabilizing the anchor in the implant by cooperation between rib (11) and groove (211). In certain other embodiments, the height of rib (11) may reach a maximum at a given distance from the posterior end, for a given portion (111), and then decrease in the direction of the posterior end. For example, as is particularly visible in the embodiments shown in FIGS. 5E and 5F, portion (111) corresponds to the portion of rib (11) that remains in groove (211) of passage (21) once the anchor is fully inserted in the implant (once the anchor comes to be stopped on the implant to hold it against the vertebra). In some of these embodiments, the transition between this portion (111) and the rest of the rib can be configured to form a shoulder functioning as a stop (112) on a surface (220) at the outlet of passage (21), so as to hold the anchor in the implant by opposing the withdrawal of anchor (1). The lower but non-null height of portion (111) allows it to inhibit transverse play of the anchor, but a portion (111) of constant height (even if less than the rest of the rib) may provide this function just as well as the one shown in FIGS. 5E and 5F with a progressively-decreasing height. In these embodiments, rib (11) therefore comprises at least one notch (112) situated at a distance from the posterior end arranged so that notch (112) is stopped on a stop surface (220) at the end of passage (21) of implant (2). This surface (220) may be outside the passage, but it is preferably formed by the outlet of the passage: the junction between the inner surface of groove (211) and a surface outside the passage, such as (in the examples shown) the inner surface of the implant wall (i.e., a surface inside the cage, in the embodiments where wall (28) of the cage defines a cavity (26), as shown in the figures). It is understood that due to the presence of this notch (112) on rib (11), so that this rib can pass into groove (211) and clear notch (112), which comes to be stopped on surface (220) of the implant, a slight deformation of the portion (215, FIG. 5E) of the implant (and/or the bottom of groove (211) if the configuration of the implant allows it) may be necessary, in particular because the anchor may not be deformable, or less deformable than the implant. This slight deformation is often possible for intersomatic cages made of solid but relatively deformable material, such as PEEK. It will be noted that it is also possible to have such notch (112) on the anchor somewhere else than on the rib. Thus, the invention foresees diverse embodiments of anchors and implants in which the anchor comprises at least one notch (112) intended to abut a stop surface (220) of the implant, which can be within or at the exit of the passage (21).

In some configurations, the anterior end of anchor (1) is designed to penetrate into a vertebra adjacent to the implantation's location of the implant (2) to be affixed. In certain embodiments of anchor (1), for example as shown in FIG. 1, the anterior end has at least one chamfer (15) or a bevel facilitating the penetration of anchor (1) into the vertebra. In some embodiments, this anterior end can comprise a cutout (13), for example in the form of a notch as shown in FIG. 1, facilitating the penetration of the anterior end into the vertebral endplates. Also note that the inner edges of the notch may or may not be sharpened. Generally, since the anterior end is the one designed to penetrate into the vertebral endplate and may guide the rest of anchor (1), it is preferred that it be made so as to facilitate penetration into the bone tissue. Thus, the figures of the present application show an anterior end configured substantially into the shape of a point (as further explained elsewhere in this disclosure). It is understood that this end can be sharpened (or ground), but that since bone tissue can be relatively resistant, it is preferable to preserve the integrity of this anterior end. Thus, as can be particularly seen in FIG. 1, for example, the anterior end preferably has a chamfer on each of the faces of plate (10) and the lateral sides of the plate are beveled so as to reduce the width of the anterior end. Preferably, these bevels terminate at a distance from one another and the anterior end is therefore terminated by a sharp edge (the one where notch (13) is made in FIG. 1, for example). On the other hand, as previously mentioned, it is preferable for anchor (1) to penetrate easily into the vertebrae without risking splitting them beyond the dimensions of anchor (1). Thus the lateral sides (or edges) of plate (10) (of the body in general) will preferably be flat, as shown in most of the figures. Hence, in general, the lateral sides of the plate (10) of the anchor (1) preferably are flat (as for example on FIGS. 2G, 2H and the majority of figures showing the anchor), so as to avoid splitting the vertebrae. These sides (or edges) are particularly (but not only) adapted to the embodiments in which the anchor doesn't comprise any rib. In other embodiments, the sides may be less flat, for example rounded or chamfered, as visible on the examples of FIG. 6D, 8F, 18A, 18B, or even sharpened so as to easily penetrate into vertebrae, but in this latter case, the anchor will preferably comprise a rib. Indeed, since the presence of a rib (11) reduces the risks of transverse movement of the anchor, it will also reduce the risks linked to the sharpening of the lateral edges of plate (10).

To enhance an anchor's ability to hold an implant (2) against a vertebra, various embodiments provide for it to be stopped against at least one surface of the implant that it is intended to affix, so as to hold the implant against the vertebral endplate, preferably firmly pressed against it. In various embodiment of anchoring device (1), the body accordingly comprises at least one retaining stop (14). Retaining stop (14) preferably has at least one stop surface oriented facing the anterior end. Preferably, this surface is oriented approximately perpendicular to the longitudinal axis and is facing the anterior end, whether it is positioned at the posterior end or further towards the front. This retaining stop (14) is designed to cooperate with at least one stop surface of a complementary stop (214) provided on implant (2) that device (1) is designed to affix, in order to hold implant (2) against the vertebra in which anchoring device (1) is designed to be anchored. In various embodiments, stop (214) preferably comprises at least one stop surface oriented facing the posterior end (i.e., toward the periphery of the implant), in order to cooperate optimally with retaining stop (14). These cooperating stop surfaces can have various configurations, for example, flat, curved, prismatic, and so on. Note that retaining stop (14) is preferably at the posterior end, as most of the figures of the present application show. In many configurations, retaining stop (14) is positioned at the level of (i.e., at or in the vicinity of) the posterior end so that it is located at, or near to, the entrance to passage (21) in the implant, abutting the complementary surface of stop (214) of the implant. This surface of the complementary stop (214) may, for example, be a surface of the peripheral wall of the implant, but it may preferably be formed by a recess, so that stop (14) doesn't protrude from (or extend beyond) the implant when anchor (1) is fully inserted therein. Furthermore, it is understood that stop (14) can be further toward the front of the anchor, so that it can be found inside passage (21), for example, as long as a complementary stop surface (214) of the implant is suitably positioned. The position of retaining stop (14) at the level of the posterior end, however, in many embodiments has the advantage of offering a good hold of the implant, particularly when the anchor is configured to contact the implant from the entrance of the passage up to the outlet. In addition, this posterior position may be preferred when configuring the implant (2) and the anchor (1) to facilitate an intentional withdrawal of the anchor, as discussed for various configurations elsewhere in this disclosure.

In certain embodiments of anchor (1), retaining stop (14) comprises at least one part protruding from at least one of the faces and/or sides (or edges) of the anchor (1). For example, the retaining stop (14) may comprise at least one projecting lug. For example, as is particularly visible in FIGS. 2G, 2H, 6D, 8D, 8E, 8F, 9A-C, 10A-C, retaining stop

(14) comprises two projecting lugs on a same face of anchoring device (1), in particular the convex face in these embodiments where the anchor curvature is oriented in the direction of the depth of plate (10). In other configurations, at least one projecting lug can be provided on any face and/or sides (or edges), or at least one lug can be provided on each face and/or sides (or edges), or there can be any other variant in the same spirit. In the example of FIG. 13G where the anchor has a curvature oriented in the direction of the width of plate (10), it is also possible to provide at least one retaining stop (14) on at least one of the faces of the plate and the example of FIG. 13G is not at all limiting. In certain embodiments of anchor (1), retaining stop (14) comprises at least one projecting lug on at least one lateral side or edge of the body of anchoring device (1). Preferably, at least one lug will be positioned on each of the 2 lateral sides, so as to improve the hold, as shown, for example, in FIGS. 5F, 6E, 6F, and 6G. In certain embodiments of anchor (1), retaining stop (14) comprises at least one projecting lug on at least one lateral face of rib (11), preferably near the posterior end of the anchor, so as to avoid creating an excessively large or deep recess around groove (211) for the complementary stop surface (214). Preferably, at least one lug will be positioned on each of the lateral faces of rib (11) at the posterior end, as shown in FIGS. 7B and 7E. As these example configurations of retaining stop (14) show, the term "projecting lug" used here should not be interpreted in a limiting manner, and the precise form of the lug can vary, for example between a small plate offering planar stop surfaces and a small stud offering curved stop surfaces, or any other variant, although some particular shapes may have various advantages, for example in terms of an efficient hold or of a voluntary withdrawal of the anchor. In addition, retaining stop (14) can have various orientations, so as to hold anchor (1) in the implant and hold the implant tight against the vertebra in an optimal manner. Several different retaining stops (14) can also be provided, positioned at different places on anchor (1). In some embodiments of anchor (1) and implant (2), the shapes of retaining stop (14) and complementary stop (214) can be arranged so that stop (14) of the anchor is mated with or locked to stop (214) of the implant, for example by locking lugs engaging a recess. In the case of anchors (1) with two curved plates connected by an uncurved portion or in the case of a single plate with a curved portion (hook-shaped, such as in publications FR 2,879,436, WO 2006/120505 and US 2006/0136063, each of which is incorporated herein by reference, particularly in the case of fixation of prostheses), this portion can serve as a retaining stop, cooperating with a shaft or at least one surface situated at the entrance of passage (21), for example. Anchoring device (1) is removable in numerous embodiments and can be implanted in the vertebrae and mated with the implant after it is installed between the vertebrae, which allows possible adjustment of the position of the implant between the vertebrae before definitive fixation by anchor (1). In some embodiments, the retaining stop can be used to pull the anchor (1) to remove it from the vertebrae, and the implant if necessary (e.g., in the case of a curved hook or a stop (214) providing a way to pull on a least a part of retaining stop (14)). Note that the example in FIG. 7E, and similar configurations, can be disposed somewhere else than on the rib (because the anchor doesn't comprise any rib or when the rib stops before rear end), and configured on a leg (or lug) projecting from plate (10). A stop formed away from the plate (through the rib or a protruding leg) can also be used to pull the anchor for withdrawal, especially if the entrance passage has a recess for access by an extraction tool.

Figure 8A:
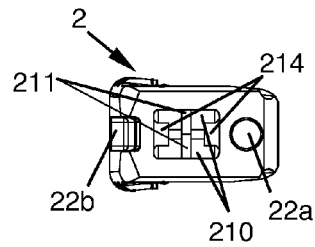
FIGS. 8A, 8B, and 8C show rear views of 3 of various intervertebral implant embodiments designed to receive anchoring devices like those shown in perspective, respectively, in FIGS. 8D, 8E, and 8F, and FIGS. 8G and 8H respectively show a top view and a sectional view along plane 8H-8H of FIG. 8G, of any of the implants of FIGS. 8A, 8B and 8C provided with any of the anchoring devices of FIGS. 8D, 8E, and 8F.
Figure 8B:
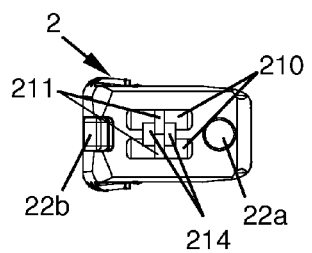
Figure 8C:
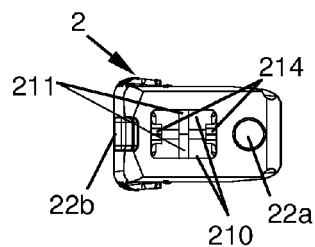
Figure 8D:
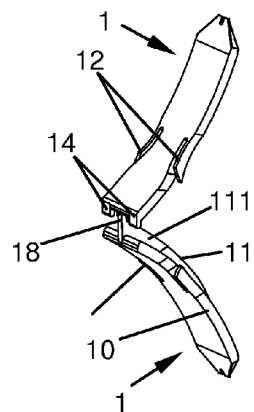
Figure 8E:
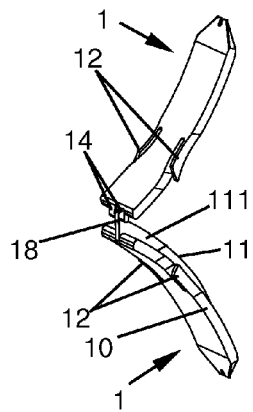
Figure 8F:
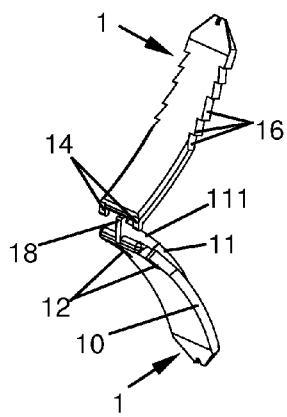
Figure 8G:
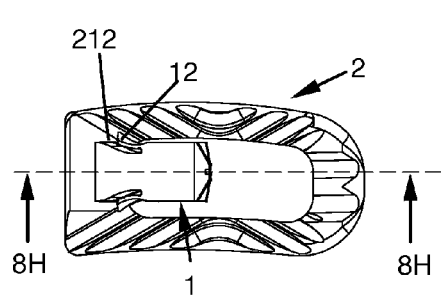
Figure 14A:
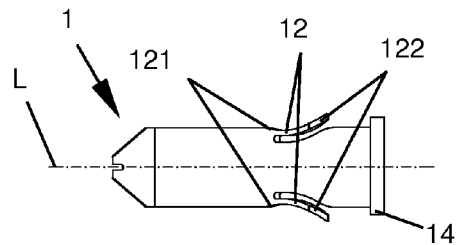
FIGS. 14A and 14B show top views of one of various embodiments of an anchoring device comprising flexible lateral lugs that are, respectively, unfolded and folded.
Figure 14B:
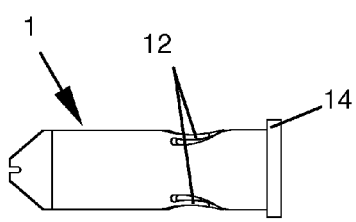
Figure 14C:
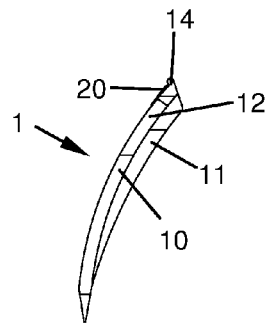
FIGS. 14C, 14D, and 14E show, respectively, a profile view, a rear perspective view, and a front perspective view of one of various embodiments of an anchoring device comprising a rib on its concave face.
Figure 14D:
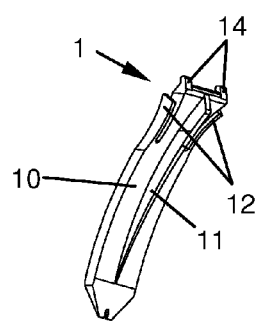
Figure 14E:
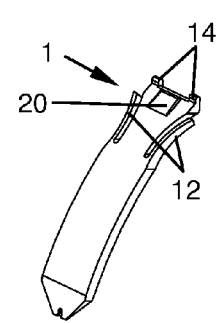
Figure 14F:
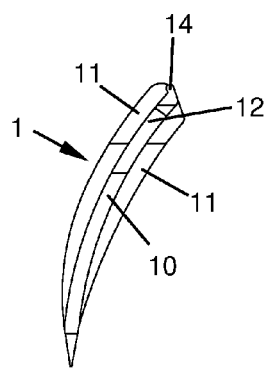
FIGS. 14F, 14G, and 14H show, respectively, a profile view, a rear perspective view, and a front perspective view of an embodiment of one of various embodiments of anchoring devices comprising a rib on each of its faces.
Figure 14G:
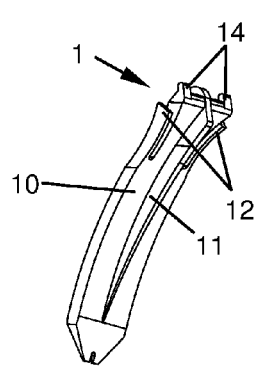
Figure 14H:
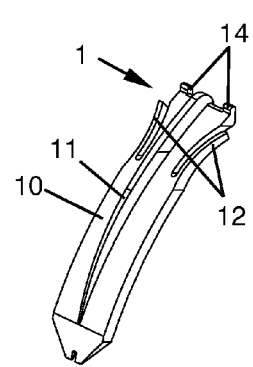
Figure 15A:
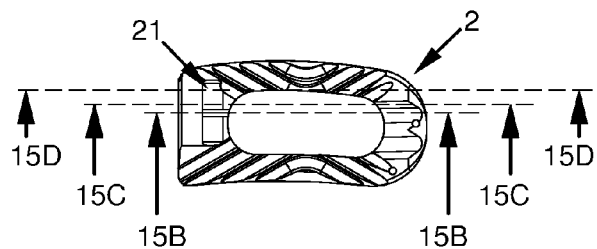
FIGS. 15A, 15B, 15C, and 15D show, respectively, a top view, a sectional view along plane 15B-15B of FIG. 15A, a sectional view along plane 15C-15C of FIG. 15A, and a sectional view along plane 15D-15D of FIG. 15A, of one of various embodiments of intervertebral implants alone.
Figure 15B:
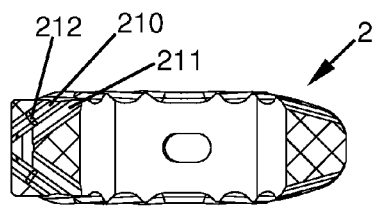
Figure 15C:
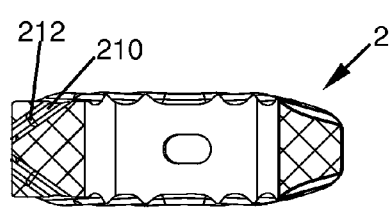
Figure 15D:
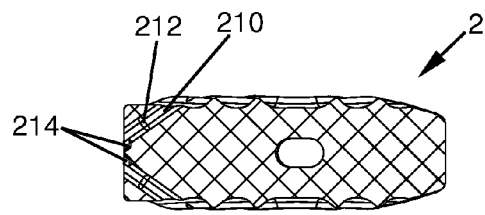
Figure 15E:
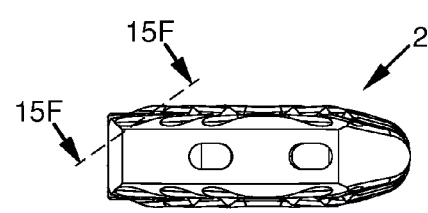
FIG. 15E shows a profile view of this implant.

In some embodiments, the body of anchor (1) comprises at least one withdrawal stop or fastener opposing the withdrawal of anchoring device (1) from implant (2), for example by cooperating with at least one complementary withdrawal stop (212) on the implant (2). The withdrawal stop can, for example, take the form of a latch comprising at least one flexible lug (12) (or tab), for example oriented substantially toward the posterior end of the anchor or of other structures to fasten anchor (1) with implant (2). As illustrated in FIGS. 14A and 14B, in various configurations these lugs are designed to retract (into the width of the plate in this example, or into the depth of the plate in other examples described herein, or even into the width or into the depth of the rib in other examples herein), in order to allow the anchor to pass into passage (21) of implants (2). The orientation of the lug may vary depending on various embodiments, particularly according to the desired spacing of the leg (12) compared to the rest of the body of the anchor (1). In some preferred configurations, the lug is flexible. It will be noted that this flexibility of the lug can be obtained by the fact that the lug is thin even though its material is substantially rigid, and/or by a substantially flexible material and/or by the shape of the lug. For example, the lug may preferably have a substantially curved shape, to enhance flexibility for it to engage at least one surface or other retaining structure of the implant. The withdrawal stop need not be oriented just toward the posterior end, but in configurations where a lug engages a surface or other structure of an implant (even if not aligned with the longitudinal axis) its direction is designated here as substantially or approximately to the posterior end because preventing withdrawal usually will be facilitated by such an orientation. Once the anchor is advanced into implant so that contact with the inner wall (210) of passage (21) is clear, flexible lug (12) is made to unfold, from which position it can abut a complementary withdrawal stop (212) of the implant, comprising at least one stop surface arranged to receive the free end (122, FIG. 14A) of flexible lug (12) and thus prevent the withdrawal of anchor (1) or at least prevent anchor (1) from coming out of implant (2) due to the effect of the forces exerted on the anchor and/or the implant. Note that in the majority of the figures showing flexible lugs on the lateral sides of plate (10) and as is particularly visible in FIGS. 14A and 14B, a portion of the free end (122, FIG. 14A) of flexible lug (12) extends beyond the periphery (for example the lateral sides) of plate (10) so as to form the stop (when the lug is unfolded), while the attachment end (121, FIG. 14A) of flexible lug (12), generally solid with the plate, is preferably formed within the periphery (for example lateral sides) of plate (10) so as not to oppose the insertion of the device into passage (21). It is noted that "flexible lug" is used here in a non-limiting manner and may refer to a flexible portion formed of one piece with the rest of the anchor, or to a separate flexible piece attached to the body (10) of the anchor, or even to an piece (either flexible or inflexible) attached to the body (10) of the anchor that flexes at an articulation area. In these configurations, flexible lugs (12) fold easily without hindering the insertion of the anchor into the implant and easily unfold to engage and abut at least one surface of withdrawal stop (212). Generally, it is preferable that flexible lugs (12) be positioned on the anchor on a portion that will not be in contact with the bone tissue when the anchor has been inserted into the vertebra, so as not to impede the unfolding of these flexible lugs. In other configurations, however, (for example, those shown in FIGS. 5D, 7B, 8G) the flexible lugs can be positioned on the anchor so that they unfold inside the passage, to be stopped on withdrawal stop (212) formed by an upper or lower surface of implant (2). In these examples, the unfolding of the lugs at the outlet of passage (21) may be impeded by the bone tissue, which may be offset by other advantages such configurations provide, such as simpler construction and potentially greater structural integrity of the implant. In other embodiments, examples of which are shown in FIGS. 2C, 2E, the flexible lugs are positioned on the anchor so as not to extend beyond passage (21) in the implant once anchor (1) is inserted within and passage (21) then comprises at least one structure (for example, a recess surface) forming withdrawal stop (212), as is particularly visible in FIGS. 15B, 15C, 15D, and especially 15F. It is understood that walls (210) of the passage will then be widened over a given portion to form withdrawal stop (212) where these lugs (12) are located when the anchor is fully inserted in the implant. Thus, in this example, the dimensions of the outlet of passage (21) are greater, at least along one axis, than those of its entrance, at least along a direction or an axis not parallel to the axis of the passage. Withdrawal stop (212) can be made by machining from the passage outlet, along an axis oriented parallel to the longitudinal axis of the passage. However, in certain variants, withdrawal stop (212) can be made along an oblique axis, so that the recesses are formed inside the passage without widening the outlet. In the case of a widened passage outlet, the play of anchor (1) in passage (21) will remain limited by the passage entrance and/or by the cooperation between rib (11) and groove (211). Preferably, these lugs will not be disposed so close to the posterior end as to require a deep recess realized from the outlet of passage (21) to form withdrawal stop surfaces (212).

Figure 13A:
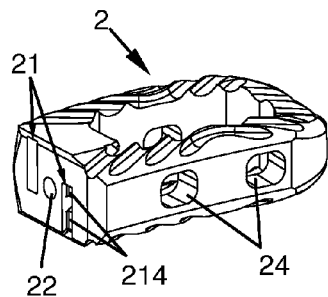
FIGS. 13A, 13B, and 13C show, respectively, a perspective view, a top view and a sectional view along plane 13C-13C of FIG. 13B, of one of various embodiments of the implant alone.
Figure 13B:
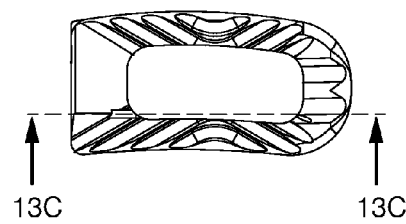
Figure 13C:
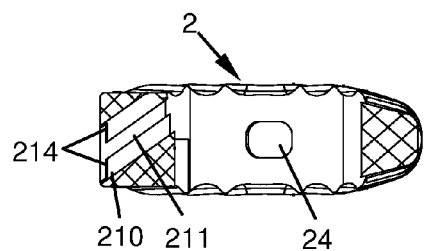
Figure 13D:
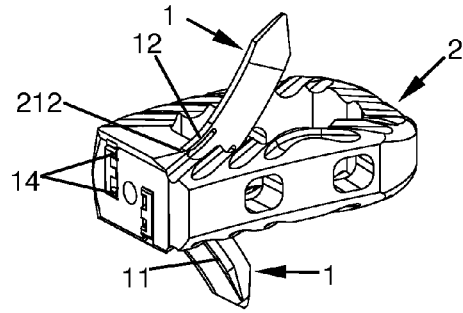
FIGS. 13D, 13E, and 13F show, respectively, a perspective view, a top view, and a sectional view along plane 13F-13F of FIG. 13E of this implant provided with a pair of anchoring devices such as the particular embodiment shown in perspective in FIG. 13G.
Figure 13E:
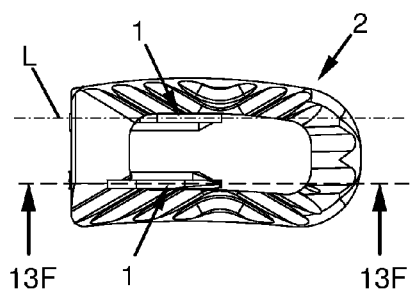
Figure 13F:
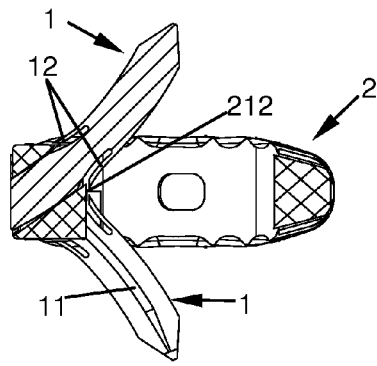
Figure 13G:
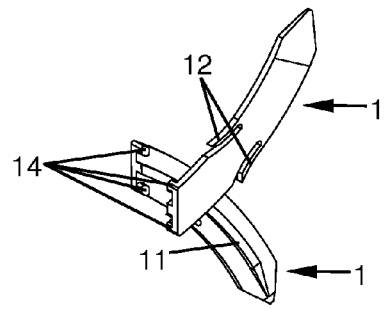

FIGS. 13D, 13F and 13G show one example of embodiment similar to the ones described above comprising lugs on the sides of the plate, but on anchors curved in the direction of the plate width. The flexible lugs in these examples are disposed on the sides (concave and convex) of the plate. However, in the embodiments with the anchor curved in the direction of the plate width (anchor with vertical orientation), flexible lugs (12), for example, can be provided on the lateral faces of the plate (for example, on the same side of rib (11) or the opposite side), or on rib (11), in each case in accordance with the discussion elsewhere in this disclosure.

Figure 9A:
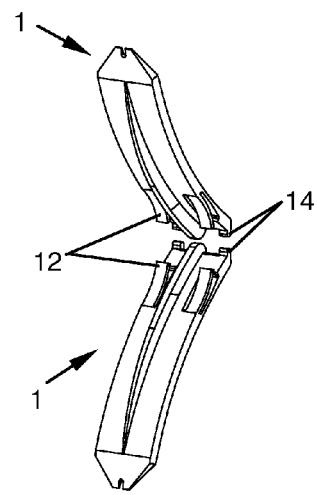
FIGS. 9A, 9B, and 9C show perspective views of pairs of anchoring devices according to 3 of various embodiments.
Figure 9B:
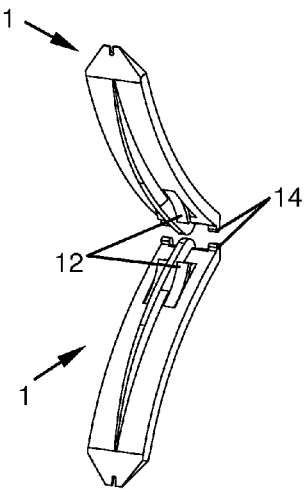
Figure 9C:
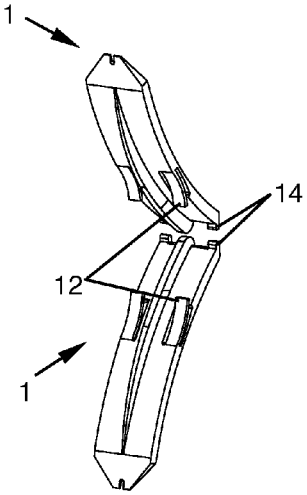
Figure 9D:
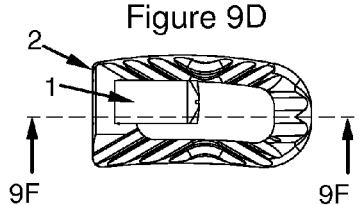
FIGS. 9D and 9E show top views of various implants designed to receive devices such as those, respectively, of FIGS. 9A and 9C, and FIGS. 9F and 9G show sectional views along planes 9F-9F and 9G-9G, respectively, of the implants and anchors of FIGS. 9D and 9E, respectively.
Figure 9E:
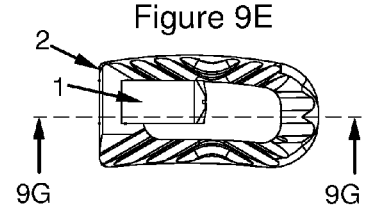

In certain embodiments of anchor (1) and implant (2), flexible lug(s) (12), instead of (or in addition to) being positioned on at least one side of the plate, can be positioned on at least one of the surfaces of the plate. FIGS. 9A, 9B, and 9C show illustrative examples of these embodiments, with flexible lugs (12) situated on the convex face of anchor (1), on either side of groove (11). Of course, these lugs can be provided on the concave surface, on both surfaces, or a single lug can be provided on one or both faces. In some configurations, especially if the size of portion 215 (e.g., FIG. 5E) of implant (2) allows it, a flexible lug (12) can be provided on the concave face, cooperating with a withdrawal stop (212) inside or on the upper surface of portion (215). In this case, a recess (240, FIGS. 15F, 18D, 18F) can also be provided on this side of the passage, to allow the flexible lug to be disengaged, as explained elsewhere in this disclosure.

Figure 9F:
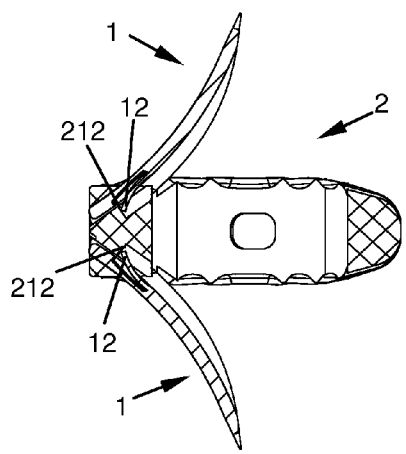
Figure 9G:
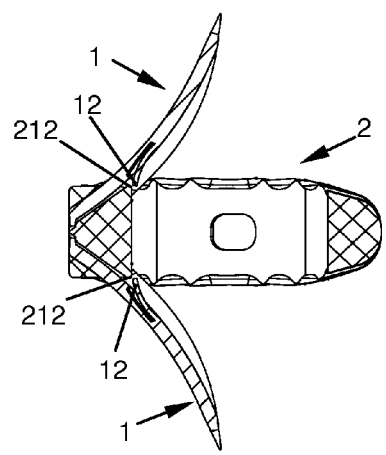

In these examples, note that the position of the lugs, on the one hand, between the anterior and posterior ends, and, on the other hand, laterally on the face, can vary. Preferably, these lugs will not be disposed so close to the posterior end that a deep recess realized (spared) from the outlet of passage (21) to form withdrawal stop surfaces (212) is required, as previously discussed. Depending on the position of flexible lugs (12), withdrawal stop (212) may be formed in various places on the implant. For example, in the case of lugs close to the posterior end like in FIGS. 9A and 9B, withdrawal stop (212) may be formed by recesses, for example as shown in FIG. 9F, created in a wall (210) of passage (21): either recesses near the lateral sides of the passage in the case of FIG. 9A, or recesses adjacent to the groove in the case of FIG. 9B. Lugs disposed further from the posterior end, like in the example of FIG. 9C, can engage a surface outside the passage, as shown in FIG. 9G.

Figure 10A:
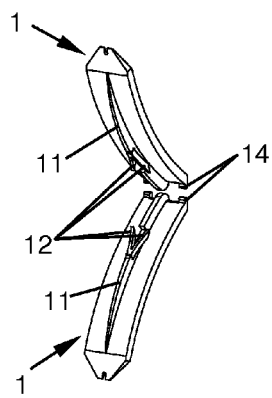
FIGS. 10A, 10B, and 10C show perspective views of pairs of anchoring devices according to 3 of various embodiments.
Figure 10B:
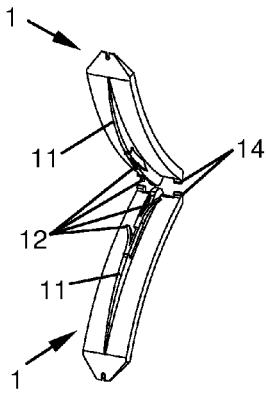
Figure 10C:
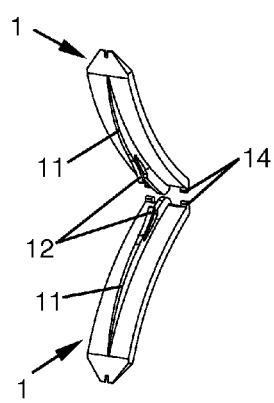
Figure 10D:
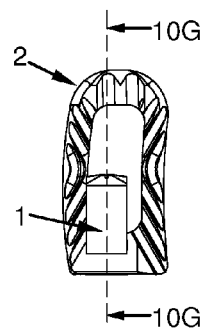
FIGS. 10D, 10E, and 10F show top views of the implants receiving devices such as those, respectively, of FIGS. 10A, 10B, and 10C, and FIGS. 10G, 10H, and 10I show sectional views along planes 10G-10G, 10H-10H, and 10I-10I respectively, of the implants of FIGS. 10D, 10E, and 10F, respectively.
Figure 10E:
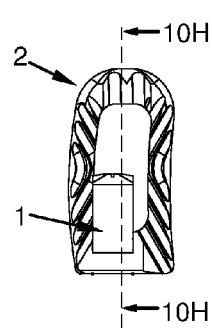
Figure 10F:
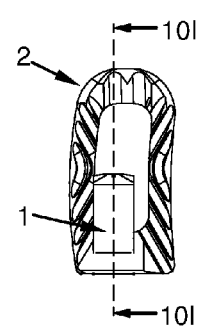

In certain embodiments, lug(s) (12), instead of (or in addition to) being positioned on at least one side or at least one face of the plate, can be positioned on the peak or on at least one side of rib (11). FIGS. 10A, 10B, and 10C show illustrative examples of these embodiments. In FIG. 10A, the rib (11) comprises two flexible lugs (12) extending beyond the sides of the rib. These two lugs preferably will be sized to be within or to approximate the width of the rib when folded. In FIG. 10B, the rib comprises a lug on each side, in this configuration offset from one another in the longitudinal axis. These lugs may also have dimensions that approximate or do not exceed the width of the rib once folded. In the example of FIG. 10B, these lugs are not as tall as rib (11) but they may be made as tall or taller. In the 2 examples of FIG. 10C, the lugs are created at the peak of the rib, at variable positions: the lug of the top anchor is situated further from the posterior end than the lug of the bottom anchor. In these examples, the lugs are preferably sized not to extend beyond the height of the rib, but they can have various dimensions or configurations.

In most of these configurations, a withdrawal stop (212) is disposed in the implant and arranged to cooperate with the flexible lugs, depending on their position on the anchor and their orientation. For example, in FIG. 10G, the anchors of FIG. 10A abut at the outside of passage (21) and withdrawal stop (212) is, in this example of an intersomatic cage having an inner cavity (26) formed by the surfaces on either side of the outlet of groove (211), inside the cavity in the cage. In FIG. 10H, the two offset lugs of anchor (1) of FIG. 10B come to be stopped in a recess along groove (211) for the one closest to the posterior end (the top one in FIG. 10H) and, for the one further from the posterior end, on a surface at the outlet of groove (211), inside the cavity in the cage. Similarly, depending on the position of the lugs along the longitudinal axis, in the example of FIG. 10I, a recess will be provided along groove (211) to form withdrawal stop (212) (see the bottom anchor in FIG. 10I), but for a lug further from the posterior end, like the top one in FIG. 10I, withdrawal stop (212) will be formed by a surface at the outlet of groove (211), inside the cavity in the cage.

Figure 10G:
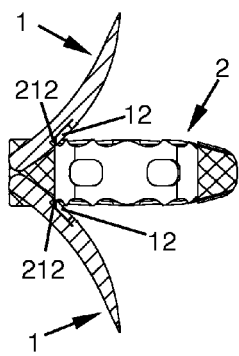
Figure 10H:
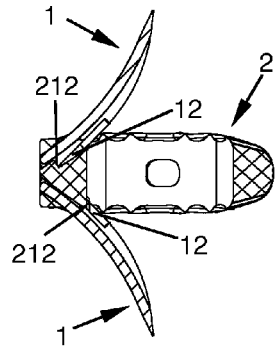
Figure 10I:
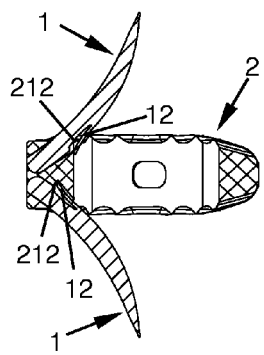

Note that in these various embodiments where the flexible lugs are positioned at a distance from the posterior end so that a recess must be made for unfolding the lugs, withdrawal stop (212) thus created can be arranged to have 2 stop surfaces, together forming an angle (preferably close to 90°), so that the free end of flexible lug (12) comes to rest on one of them and opposes withdrawal of the anchor and that the other surface inhibits deformation of the lug when anchor (1) is subject to forces tending to cause its withdrawal from the implant, as can be particularly seen in the examples of the bottom anchor of FIG. 10I or, in a less confined manner (i.e., with a larger recess), on both anchors of FIG. 9F. Note that in those embodiments where the lugs (12) are flexible on the convex or concave sides of the anchor (1) and cooperate with a recess in the implant, lugs (12) can be made flexible to be apart from the body of the anchor a distance greater than the depth of their stops in the implant, so they exert force on the implant and help stabilize the anchor (1) and limit its play in the implant (2), which can be particularly advantageous when the passage (21) has a height higher than the anchor, in particular when the passage is straight.

In certain embodiments, the free end of the lug can be beveled, as can be particularly seen in FIGS. 10G, 13F, preferably with an angle arranged as a function of the orientation of withdrawal stop surface (212) to hold the anchor in an advantageous manner. The free end also may be beveled to facilitate unfolding lug (12) despite tight adjustment (or alignment) of lug (12) and withdrawal stop (212), such as, for example, in the case of FIG. 9F, where it appears, for purposes of illustration, that the unfolding of lug (12) risks being impeded by the straight shape of the free end. Generally, for particularly advantageous configurations, the position of withdrawal stop (212), and the orientation of its stop surface(s) receiving the free end of the flexible lug, are dependent, and vice versa, on the position of flexible lug (12) on anchor (1) and the shape of the free end of flexible lug (12).

As mentioned in this disclosure, various configurations of anchor (1) may comprise a recess allowing flexible lugs to be fully folded so they do not project beyond the body of the anchor and impede the insertion of the anchor in passage (21). In the embodiments with flexible lugs (12) positioned on the lateral sides of the anchor, as shown, for example, in FIGS. 14A and 14B, this recess may be formed by a thinner width of plate (10) at lugs (12) than along the rest of the body of anchor (1). In the embodiments with flexible lugs (12) positioned on at least one of the faces (concave or convex) of curved plate (10) of the anchor, as shown, for example, in FIGS. 9A, 9B and 9C, this recess may be formed by a thinner part of plate (10) at lugs (12) than along the rest of the body of anchor (1). In the embodiment where the flexible lug is positioned on rib (11), the size (height or width) of folded flexible lug (12) will be less than the height or width, respectively, of rib (11), so as not to impede the insertion of anchor (1) into passage (21).

It is understood from the examples of flexible lugs (12) discussed herein that numerous variants are possible and that the illustrative and non-limiting examples described here in reference to the figures serve to illustrate the diversity of these possibilities. Although certain configurations may be more advantageous than others, any extreme or intermediate configuration, including those among or between those described herein, are within the scope of the invention.

In certain embodiments of anchor (1), the body may be configured with notches (16) oriented to oppose the withdrawal of device (1) once it is implanted in a vertebra. Preferably, these notches will be present only along the portion of the body of anchor (1) that is designed to emerge from the passage when the anchor is fully inserted in the implant. As can be particularly seen from the nonlimiting examples shown in FIGS. 2H, 6D, and 8F, these notches (16) can vary in number, size and shape.

Figure 6A:
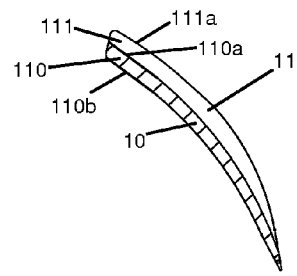
Figure 6B:
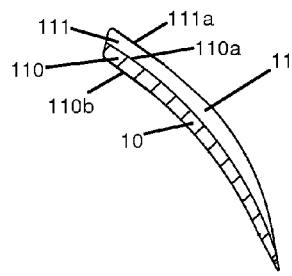
Figure 6C:
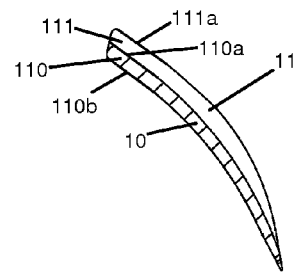
Figure 6D:
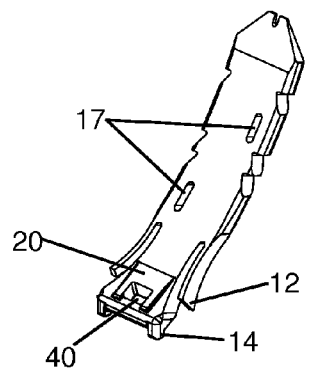

In certain embodiments of anchoring device (1), at least one opening (17) through plate (10) allows bone to grow through the opening once device (1) is implanted, as can be particularly seen in the nonlimiting examples shown in FIGS. 2H and 6D. Such openings (17), by permitting bone tissue to grow through plate (10), inhibits anchor (1) from coming out of the vertebra once the osteosynthesis is completed. In some embodiments, a rib (11) may be used advantageously to mitigate any structural weakness of plate (10) that may be caused by opening (17).

In certain embodiments, the ability to readily withdraw the anchor is preferred, and in those embodiments openings (17) and/or notches (16) would be generally undesirable. Certain embodiments described herein comprise at least one mechanism allowing removal of anchor (1), and in those embodiments the size of these openings (17) may be limited so that they can play their role of holding anchor (1) without impeding withdrawal of anchor (1) by means described herein. Likewise, the shapes and sizes of notches (16) can also be adapted so as to oppose spontaneous withdrawal of anchor (1) while permitting intentional withdrawal by means of the mechanisms described herein. These embodiments are thus not necessarily exclusive, and depend on the sizes of openings (17) and/or the shapes and sizes of notches (16).

Figure 6E:
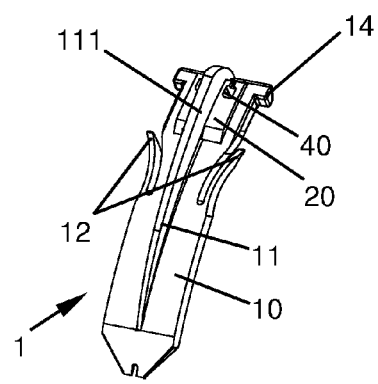
Figure 6F:
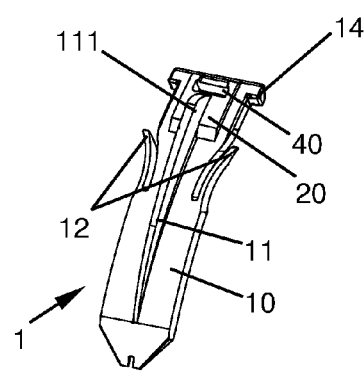
Figure 6G:
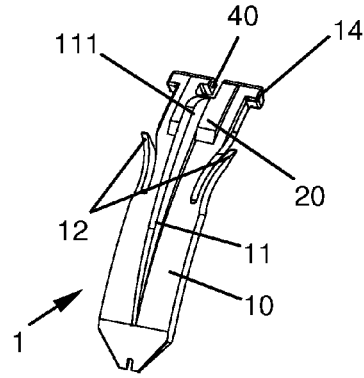
Figure 15F:
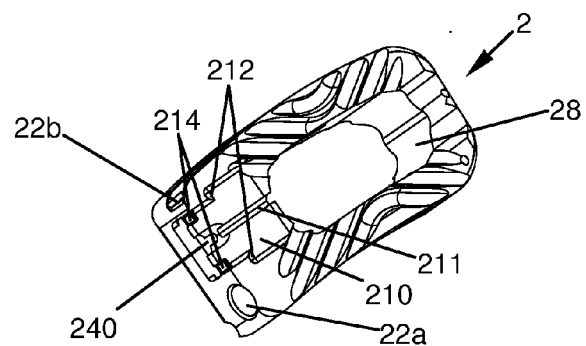
FIG. 15F shows a sectional view along plane 15F-15F of FIG. 15E of this implant, revealing the shape of a passage in the implant for an anchoring device.
Figure 18B:
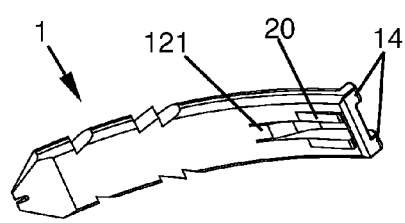
Figure 18C:
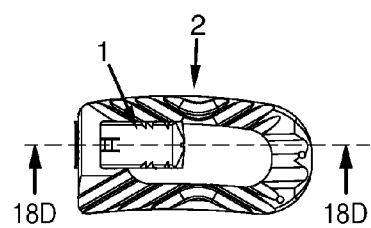
FIGS. 18E and 18F represent respectively a top view and a sectional view along the plane 18F-18F of FIG. 18E, of this implant without the anchoring devices in place.
Figure 18D:
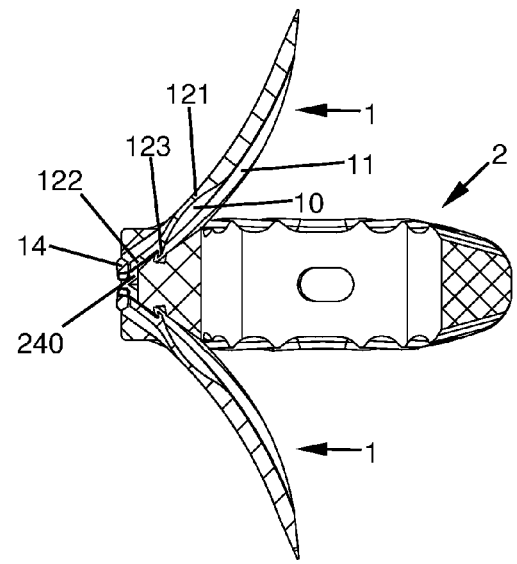
Figure 18E:
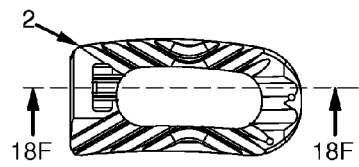
Figure 18F:
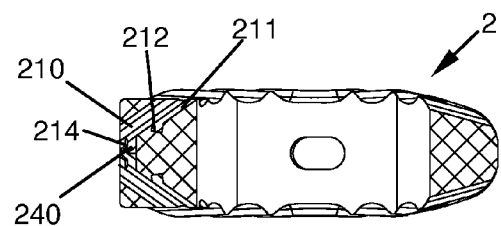

In certain embodiments, anchor (1) (and/or implant) comprise(s) a withdrawal mechanism facilitating the intentional withdrawal of the anchor from the implant and the vertebra using an anchor extraction tool, if necessary. The tool for extracting anchoring device (1) can have various forms, such as, for example, a shaft curved at its end (like a hook) so as to penetrate into a recess and allow the withdrawal of the anchor by pulling on a shaft. For example, in certain embodiments, retaining stop (14) may be configured with a catch to facilitate withdrawal of anchor (1). In some of these embodiments, such a catch can be obtained by making retaining stop (14) wider than complementary stop (214) of implant (2) on which it comes into contact. Complementary stop (214) or a nearby area of implant (2) may be configured with a space or gap that allows inserting an anchor extraction tool to pull on retaining stop (14). When anchor (1) comprises at least one withdrawal stop or latch opposing the withdrawal of anchor (1), this stop or latch can be configured to be released and allow withdrawal of the anchor (1). For example, the free end of the flexible lug (12) may be configured so that it can be disengaged from withdrawal stop (212) of implant (2), through a channel emerging at the end of implant (2). For configurations with a flexible lug (12) disposed near the posterior end, a channel may be provided, for example, through a portion of the implant from the posterior wall to withdrawal stop (212), for example beside groove (211) or beside passage (21) in a general way, depending on the position of flexible lug (12). For example, FIGS. 15F, 18D and 18F shows examples of a recess (240) emerging at the entrance of the passage (21), into which an anchor extraction tool may be inserted, for example to disengage the flexible lug (12) of an anchor like the one shown in FIG. 11B and respectively 18A (and 18B) and/or to pull on a retaining stop (14) like the one shown in FIG. 8E and/or another mechanism as explained elsewhere herein. Other embodiments described elsewhere herein allow disengagement or unlatching of flexible lug (12) with a mechanism that does not require such a recess (240) or channel in implant (2). In certain embodiments, the body of anchor (1) comprises, near the posterior end, at least one recess (40) arranged to receive a tool for extracting anchor (1) and allowing withdrawing the anchor by pulling up. FIGS. 6D, 6E, 6F, and 6G show examples of such a recess (40), created through plate (10), near the posterior end. In certain embodiments (not shown), recess (40) can be created in the rib, for example near the posterior end. Such a recess (40) in plate (10) or rib (11) of anchor (1) can, according to the configuration of the implant at the entrance of passage (21), be made accessible by means of a recess (240) such as the one shown in FIG. 15F. In FIGS. 6D, 6F, and 6G, rib (11) does not extend up to the posterior end of the anchor, so as to leave sufficient space for providing such recess (40) in the anchor (1). In the example of FIG. 6E, the rib extends to the posterior end, but a recess (40) will be created at least on one side of the rib (both sides in the example shown). In the example of FIG. 6G, recess (40) of the anchor is open on the posterior end, so that the tool can directly access this recess (40) for withdrawal of the anchor, without relying on a recess (240) in implant (2) for introduction of an extraction tool, as typically would be used for the examples of FIGS. 6D, 6E, and 6F. Although open, this recess (40) still offers a catch surface backing the posterior end for pulling on the anchor toward the posterior end to withdraw it from the vertebra. Note that in FIG. 15F, an implant (2) is shown configured to receive anchors of the types of FIG. 11B, and also some configurations of the devices shown in FIGS. 11F, 10C, and 12, since it comprises a recess (240) for insertion of the tool for unlatching flexible lug (12).

In certain embodiments, anchoring device (1) comprises a mechanism that will assist stabilizing it in passage (21) in the implant. In certain embodiments, for example, a curved anchor is provided to pass through a straight passage of the implant, without deformation of the anchor (1) in spite of its curvature. These embodiments of implants (2) with straight passage (21) are easier and less expensive to make than the embodiments of implant (2) with curved passage (21). However, for a curved anchor to pass through the straight passage, the height of passage (21) must be at least slightly greater than the thickness of plate (10) in the embodiments of anchors with horizontal orientation (curved in the direction of the plate depth), or greater than the width of plate (10) in the embodiments of anchors with vertical orientation (curved in the direction of the plate width). It is preferable, though, that the anchor has little or no play in passage (21) of implant (2), at least to prevent movements of the anchor (and/or the implant) that will tend to make the anchor come out of the vertebrae. As noted elsewhere in this disclosure, the body of the anchor in some configurations can have various radii of curvature between the two ends (anterior and posterior). In certain embodiments, the curvature of anchoring device (1) at the posterior end can be configured to engage wall (210) of passage (21) sufficiently to improve the hold of anchoring device (1) on implant (2). In certain embodiments, rib (11) may comprise on its peak (i.e., on its upper surface, the face opposite the plate) and at a portion (111) near the posterior end, a planar surface (111*a*, FIGS. 6B, 6C) limiting the play of device (1) in implant (2) with an interference fit with a planar surface of the bottom of groove (211) of passage (21) of implant (2). In certain variants of these embodiments, the body has, at a portion (110) close to the posterior end and on its face opposite the one with rib (11), a planar surface (110*b*) limiting the play of the device in passage (21) of implant (2) with an interference fit with planar surface (111*a*) of the rib, as shown in FIG. 6B. In other embodiments, curved plate (10) of the body is extended at a portion (110) near the posterior end by a straight plate whose planar surfaces (110*a*, 110*b*, FIGS. 6A, 6C) limit the play of the device in passage (21) of implant (2) by being slightly thicker than the rest of plate (10). FIG. 6C shows a combination of these planar surfaces (110*a*, 110*b*) of plate (10) with a planar surface (111*a*) of rib (11). It is understood that portions (111 and 110) close to the posterior end generally correspond at most to the entire length of passage (21), but they are preferably shorter, since the insertion of the anchor through passage (21) could be inhibited if they were too long. An instrument (e.g., 3, 4) (described elsewhere in the disclosure) for inserting anchors (1) into the vertebrae through an implant is a potential object of the invention, and therefore it is preferable for anchors (1) to be configured to pass through this instrument (3, 4). Thus, preferably a thickened portion, possibly planar, on a part of the length of the anchor, will not impede guidance of the anchor into and through the instrument. Thus, in various embodiments, the anchor may be stabilized in the passage by means of at least one thickened stabilization portion (20), typically having a width less than the width of plate (10) but a thickness greater than that of the rest of plate (10), such as, for example, as shown in FIGS. 6D, 6E, 6F, 6G, 14C, and 14E. Stabilization portion (20) should not prevent retaining stops (14) from being stopped on their complementary stop (214) in the implant, so when these retaining stops are created on one of the faces of the plate, the stabilization portion (20) preferably will thus be positioned on the face opposite the one comprising retaining stops (14), which will improve their function of stop. Also, in some embodiments depending on the configurations of various elements it is preferable for stabilization portion (20) to be on the face opposite the one comprising the rib to provide better engagement of the rib in its groove, in particular when it will be preferred to use this stabilization portion in combination with a planar surface (111*a*) of rib (11). Note that in cases where the anchor (1) combines the stabilization portion (20) and recess (40) for withdrawal, the portion (20) preferably does not extend to the posterior end of the anchor, as particularly visible in FIGS. 6D, 6E, 6F and 6G, to facilitate access to recess (40) for the withdrawal of the anchor (1). During insertion of various configurations of anchor (1), the stabilization portion may impede passage of the anchor if the increase in thickness is too abrupt. Thus, stabilization portion (20) may comprise at least one chamfer, for example where it meets the plate, substantially toward the anterior end, for example as visible in FIGS. 6D, 6E, 6F, 6G, 14C, and 14E, so as to provide a progressive increase in thickness up to the optimal thickness that presses anchor (1) in passage (21) and thus limits its play. Similarly, planar surfaces (110*a*, 110*b*, 111*a*) mentioned above can be integrated progressively. In some configurations, the height of the rib, in particular in the case of a planar surface (111*a*), whether alone or in combination with other planar surfaces or the stabilization portion, can be greater at portion (111) near the posterior end than on the rest of the rib, so that this portion (111) of rib (11) serves to stabilize the anchor (1) in implant (2). Note also that the thickness of thickened portions (20 or 110) preferably will still be slightly less than the height of passage (21), so as to limit play without completely eliminating it (and/or the height of the rib on portion (111) will be slightly less than the depth of complementary groove (211)). Nevertheless, in certain variants, this thickness (and/or height) will be equal to or even somewhat greater than the height of passage (21) (and/or depth of the groove, respectively), notably in the case of intersomatic cages whose material (such as PEEK, for example) allows a slight deformation (for example a deformation of portion (215) of the cage shown in FIG. 5E).

The present application foresees various embodiments of objects such as anchors (1) comprising no rib (11), in which anchor (1) is curved but the passage (21) is straight (and higher than the height of anchor) and in which the plate (10) comprises the stabilizing portion (20) and/or at least one of the portions having a plane surface (110*a*, 110*b*) described in the present disclosure. The implants and instruments that may be associated with such anchors then need not comprise grooves (211, 3011). These objects allow limiting the play of the curved anchor (1) within the straight passage of implant (2). These particular objects may also comprise or not, according to various embodiments, any technical feature (or combination of technical features) described for any element (or combination of elements) of any object (or combination of objects) disclosed in this application, as long as they are not incompatible, in particular because the structural adaptations that may be required by such isolation or combination of features are directly derivable from the appreciation of the present disclosure.

A single anchoring device (1) may be used to anchor an implant (2) in a vertebra, but in most applications at least two devices preferably will be used to affix an implant (2) in the 2 adjacent vertebrae between which it is implanted (at least one anchor for each vertebra). As previously mentioned, another potential object of the invention is an anchoring system for the implant comprising two anchoring devices (1), either identical to each other, or different, or complementary to each other. Thus, the combinations of any of the embodiments of anchors described herein whatsoever are within the scope of the invention.

Figure 8H:
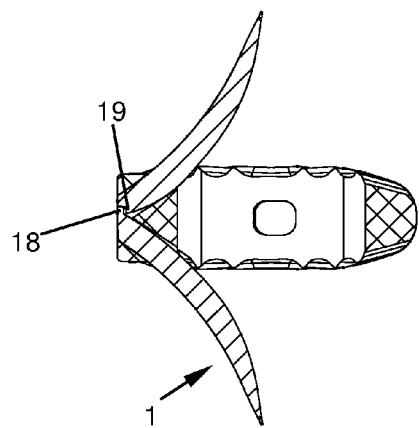
Figure 11A:
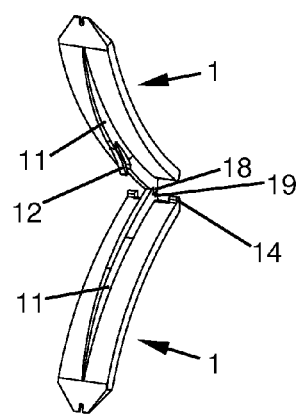
FIGS. 11A and 11B show perspective views of pairs of anchoring devices according to 2 of various embodiments.

In certain of the embodiments with complementary anchors, a first anchoring device (1) comprises a first cooperation stop (18) comprising at least one stop surface oriented substantially facing the anterior end, and a second anchoring device (1) comprises a second cooperation stop (19) comprising at least one stop surface oriented substantially facing the posterior end. These first and second cooperation stops (18, 19) are configured to cooperate with each other, so that the first device (1) holds the second device (1) once they are in place in implant (2), and/or vice versa. For example, as shown in the illustrative and non-limiting examples of FIGS. 8D, 8E, 8F, and as particularly visible in FIG. 8H, first anchor (1) can have a first stop (18) such as a lug, a shoulder, or a tab projecting in the direction of second anchor (1) which can have a second stop (19), such as a lug, a shoulder, or a tab, arranged so that the first stop (18) and the second stop (19) abut each other in a complementary manner. Note that in the examples of FIGS. 8D, 8E, and 8F, the first anchor (the bottom one comprising cooperation stop (18)) does not need retaining stop (14) since it rests on cooperation stop (19) of the second anchor (the top one) which has retaining stops (14). However, first cooperation stop (18) of the first anchor also may form a retaining stop (14), or vice versa. In the examples shown, the advance of anchors (1) in the passage is blocked by retaining stops (14) of the second anchor and by cooperation stop (18) of the first anchor. In these configurations, the second anchor retains the first by preventing it from entering too far into the passage. In return, cooperation stop (18) of the first anchor retains the second anchor and prevents it from coming out of the implant. In certain embodiments, cooperation stop (19) can be formed at least by a surface situated on the posterior face of retaining stop (14) of the second anchor. In certain embodiments, only first anchoring device (1) having cooperation stop (18) will have a withdrawal stop (12), such as a flexible lug (12) for example, configured to cooperate with a withdrawal stop (212) of the implant, as shown in FIG. 11A, and in these configurations, cooperation stop (18) of first device (1) may serve as a withdrawal stop for second device (1) by abutting the second stop (19). In these configurations, the second device (1) is retained on first device (1) by cooperation stops (18 and 19), and flexible lug (12) retains first device (1) on withdrawal stop (212) of implant (2), for example as particularly visible in FIG. 11E. As noted, in certain embodiments only the second device (1) comprising stop (19) may be configured with a retaining stop (14), since cooperation stop (18) of the first device (1) can play the role of retaining stop for the first device (1), by abutting against the stop (19) of the second device (1), which is held in this direction by a retaining stop (14).

Figure 11B:
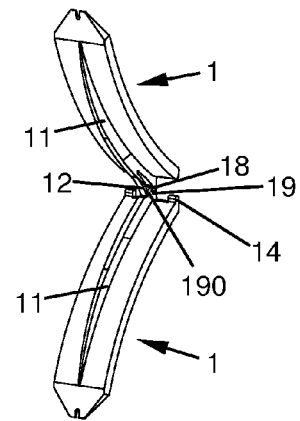
Figure 11C:
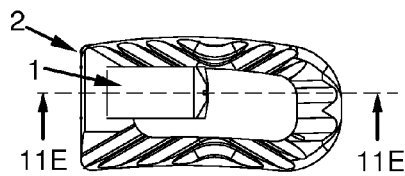
FIGS. 11C and 11D show top views.
Figure 11D:
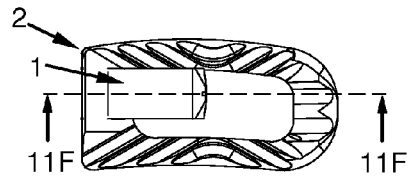
Figure 11E:
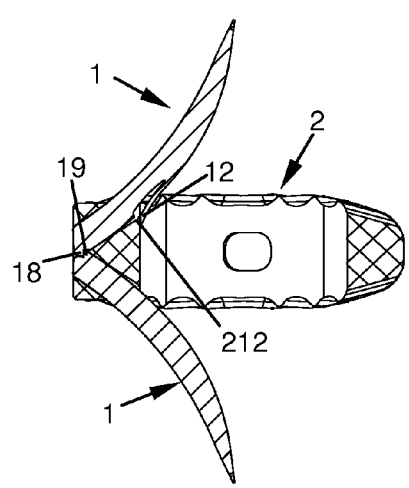
FIGS. 11E and 11F show sectional views along planes 11E-11E and 11F-11F, respectively, of implants deployed with the anchors of FIGS. 11A and 11B, respectively.
Figure 11F:
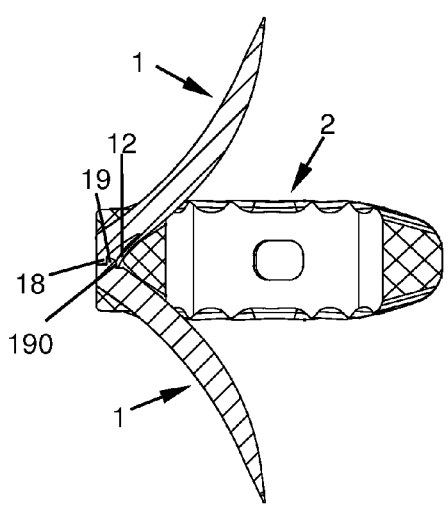
Figure 12A:
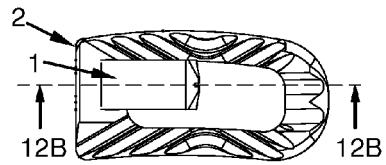
FIGS. 12A and 12B show, respectively, a top view and a sectional view along plane 12B-12B of FIG. 12A of various embodiments of an intervertebral implant provided with a pair of one of various embodiments of anchoring devices.
Figure 12B:
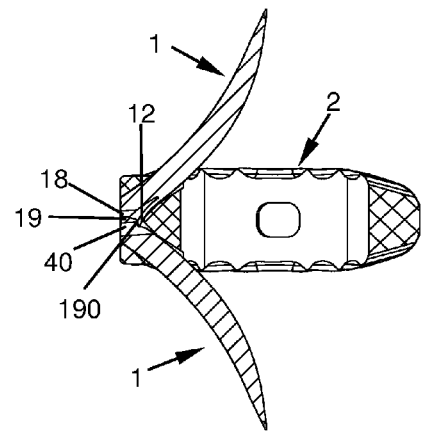
Figure 12C:
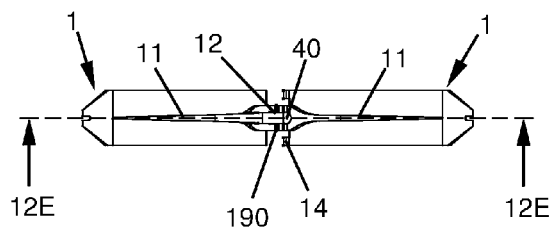
FIGS. 12C, 12D, and 12E show, respectively, a front view, a perspective view, and a sectional view along plane 12E-12E of FIG. 12C of this pair of anchoring devices in a deployed configuration.
Figure 12D:
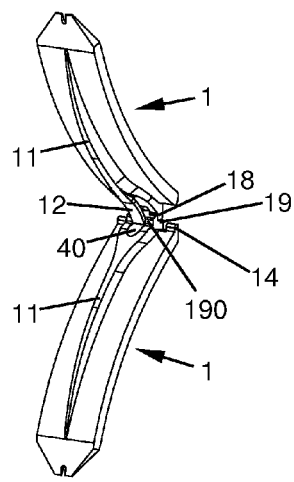
Figure 12E:
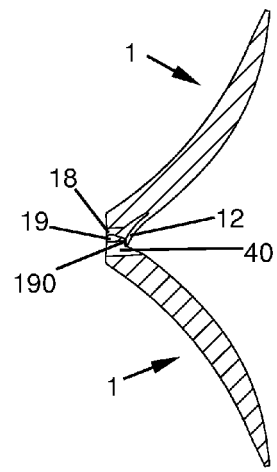

In certain embodiments of anchoring systems with complementary anchors, cooperation stops (18, 19) may further interlock to inhibit movement of both the first and the second anchoring devices (1) in both the anterior and posterior directions. An illustrative and non limitative example of one of these embodiments is shown in FIGS. 11B and 11F. For the illustrated configuration, cooperation stop (19) of the second anchoring device (1) comprises a second cooperation stop surface (190), oriented substantially facing the anterior end, and the first device (1) comprises a withdrawal stop (here in the form of flexible lug (12)) positioned so that the free end of the lug (12) (its posterior end) comes into contact with and is retained by the second surface (190) of stop (19), thus preventing withdrawal of the first device which retains the second device (1) once it is in place in implant (2). Note that in these embodiments, as mentioned elsewhere in this disclosure, a channel or recess (240) such as the one shown in FIG. 15F for example, will allow inserting an extraction tool for disengaging flexible lug (12) from second stop surface (190). In some other embodiments that do not require a recess or channel in the implant, as particularly seen in FIG. 12(A-E), cooperation stop (19) of the second device comprises a recess (40) (or conduit or channel). As can be particularly seen in FIGS. 12B and 12E, this recess emerges near second stop surface (190), which allows disengaging flexible lug (12) with a tool. Note that this recess (40) also can be used to withdraw the anchor, as described elsewhere herein. In various configurations, therefore, the end of flexible lug (12) (i.e., the free end of the lug) of the first device (1) can be disengaged from second stop surface (190) of stop (19) of the second device (1) through a recess or channel accessible from outside the implant and that this channel can be created either in the implant or in one of the anchors, and that a recess or channel in the anchor can correspond to (or also form a) recess (40) facilitating intentional withdrawal of the anchor.

Cooperation stops (18, 19) are shown in FIG. 11 (A through F) and 12 (A to E) located at the rib, but they could be disposed elsewhere on the body of the anchor (1). By providing an interlock, an anchor retains the other (and vice versa in some configurations), helping to reduce the footprint of the implant (and therefore its machining, which may avoid reducing its strength).

These various configurations of cooperation stops (18, 19) allow providing various embodiments of potential objects of the invention concerning anchoring system with anchors comprising cooperation stops (18, 19) with or without the second cooperation stop surface (190) opposing the withdrawal, and may but need not comprise rib (11). These particular objects may be configured to solve the problem of minimizing the stop structures of the anchor thanks to the technical features enabling a reciprocal engagement. These diverse objects may also concern anchors having a straight body instead of a curved body. For configurations without rib (11), the implants and instruments that may be associated with such anchors may then not comprise grooves (211, 3011). As noted elsewhere, in configurations comprising second surface (190), each anchor blocks the withdrawal of another. These particular objects (i.e., any of these embodiments with the cooperation stops (18, 19)) may or may not also comprise any technical feature (or combination of technical features) described for any element (or combination of elements) of any object (or combination of objects) disclosed in this application, as long as they are not incompatible, in particular because the structural adaptations that may be required by such isolation or combination of features are directly derivable from the appreciation of the present disclosure.

In some embodiments, as particularly visible in FIGS. 18A and 18B, the anchor has a step (123) (such as a shoulder or a notch) between the free end (122) and attachment end (121) of the lug (12). In these embodiments, this step (123) is intended to abut the withdrawal stop (212) of the implant when the anchor is seated, for example as seen in FIG. 18D. In some of these embodiments, the free end (122) does not engage a withdrawal stop of the implant, but instead extends to near the posterior end of the anchor, so as to be accessible for disengagement of step (123) by pressing the free end (122) in the direction away from stop (212). In the example shown in these figures, the free end (122) extends to nearly the posterior end of the anchor, but is still behind a rod (for example, between retaining stops 14) that may be used to pull on the anchor to withdraw it from the vertebra and implant, if desired. In this example, recess (240) in the implant provides access to the free end (122), as particularly visible in FIGS. 18D and 18F. In some configurations, however, for example where the anchor is configured with a stop (14) or recess (40) or other structure that can be used to pull on the anchor (for example, a curved or hook-shaped stop or a stop with an opening), the lug may extend to the posterior end of the anchor, so it is accessible without the need for a recess (240) in the implant or by way of a less sizeable recess. In some embodiments, the attachment end (121) of lug 12 is secured to the body in the thickness of the plate (10), which in this non-limiting example is hollowed out to accommodate the flexible lug (12), as shown in FIG. 18B. In this example, only one lug (12) provided with the step (123) is located substantially at the middle of the anchor (between its lateral edges) but various other embodiments foresee at least one lug (12) provided with step (123) located elsewhere on the anchor, such as for example close to a lateral edge of the plate, and engaging a complementary withdrawal stop (212) located on an edge of the passage (21) in the implant (with some variants comprising for example such a stop mechanism on each on the lateral edges of the anchor).

Various embodiments of the anchor (1) (and/or of the implant) comprising at least one withdrawal stop (12) on the anchor, such as a flexible lug (12), that can be disengaged from a complementary withdrawal stop (212) of the implant or from a second cooperation stop surface (190) (for example, through access to the free end of the lug via the anchor itself and/or via the implant), which are described in this application, solve the problem of withdrawing the anchor from the vertebra and implant despite the presence of a withdrawal stop or latch (and eventually despite the encumbrance of the implants and of this type of fixation). These technical features for the disengagement (liberation) of the withdrawal stop thus allow many embodiments of objects such as anchoring devices and/or systems in which anchor (1) may, but need not, comprises rib (11). The implants and instruments that may be associated with anchors without rib (11) need not comprise grooves (211, 3011). Some objects concerned may be implants comprising a recess (240) for access to the withdrawal stop (12) of anchor (1). Various objects may also concern anchors having a straight body or having a curved body. These particular objects (i.e., any of these embodiments allowing to disengage the withdrawal stop (12) of the anchor) may or may not also comprise any technical feature (or combination of technical features) described for any element (or combination of elements) of any object (or combination of objects) disclosed in this application, as long as they are not incompatible, in particular because the structural adaptations that may be required by such isolation or combination of features are directly derivable from the appreciation of the present disclosure.

Intervertebral implants (2) comprising at least one passage (21) designed to receive anchoring device (1), such as a slit crossing a portion of the implant, a conduit, or another type of channel arranged to receive anchoring device (1), are also within the scope of the invention. Preferably, such implants are configured to receive at least one anchoring device (1) comprising at least one curved and rigid plate, so as to allow the passage of this anchoring device (1) through the passage (21) without deformation despite the curvature of the device (1). In most configurations, passage (21) crosses implant (2) from a peripheral wall (28) to an upper or lower surface of implant (2), along a preferably rectilinear and oblique trajectory suited to the curvature of anchoring device (1) and the desired fixation of the implant, as discussed in detail elsewhere in this disclosure. In some configurations, passage (21) in the implant comprises at least one groove (211) of shape and size arranged for receiving a rib (or ribs) (11) of anchoring device (1), as explained elsewhere herein. The present application does not describe intervertebral discs in detail, but rather only describes various embodiments of intersomatic cages designed for an arthrodesis. The person skilled in the art will nevertheless understand after appreciating this disclosure that anchoring device (1) configured with various features and various combinations of features according to the invention may be used with a prosthesis comprising at least one peripheral wall to receive anchor (1) as described herein. For example, intervertebral prostheses are known whose vertebral contact plates have a sufficient height to offer a peripheral wall in which it is possible to create a passage such as described herein for the insertion of the anchoring device. Likewise, intervertebral prostheses are known comprising two plates and a mobile core between the plates and in which a peripheral wall of one of the plates limits the movements of the core. Therefore, the invention can be adapted to this type of prosthesis, by making at least one passage (21) in the wall, crossing said wall from a peripheral surface to a vertebral contact surface (lower or upper) of the plate without hindering the movements of the various parts of the prostheses, such as the core, for example. In various embodiments, the passage (21) in the plate need not cross the plate from a peripheral wall of the plate, but instead may cross the plate from one side to the other side (i.e., the upper surface to the lower surface, or vice versa), according an oblique axis (straight or curved) extending from a peripheral area of the prosthesis itself to a vertebral endplate, and the stops (14) and/or flexible tabs (12) of anchor (1) can be adapted to make contact with the upper or lower surfaces of the plates (directly or via stops arranged within the plate). For example, publications FR 2,879,436, WO 2006/120505 and US 2006/0136063, each of which is incorporated herein by reference (filed by the assignee of this application), show a straight anchor with a retaining stop formed by a curved portion (hook-shaped) at the posterior end of the anchor configured to engage a stem near the edges of plates, and this general approach can be adapted to the embodiments disclosed herein after fully appreciating this disclosure. The anchor (1) of the present invention may, for example, be curved and/or comprise one or more ribs (11) and/or one or more retaining stops (14) and/or one or more withdrawal stops (12), for use with such prostheses, and additional features and/or combinations of features described herein may be adapted to such use. In cases where the anchor is designed to cross through a plate of a prosthesis, the term "peripheral wall" may be used to designate a portion near the periphery of the plate and accessible from a peripheral area of the prosthesis.

Accordingly, certain embodiments of the present invention also concern an intervertebral disc prosthesis created with the means described generally for implant (2). Various types of intervertebral disc prostheses are known and no detail will be given here, except that it may for example comprises at least two plates articulated together (for example via articulation surfaces of the plates and/or an intermediate core) and at least one of which comprises at least one passage (21), for example provided with at least one groove (211) when the anchor comprises a rib (11). Intersomatic cages configured in accordance with the present invention also can have various forms, including configurations notably different from the illustrative examples represented in the figures of the present application. The description herein gives several non-limiting variants of embodiment in reference to the attached figures, but after fully appreciating this disclosure it will be understood that the cages and/or prostheses devised in accordance with the present invention may have other forms without departing from the spirit and scope of the invention. Thus, in the present application, reference is made generally to an intervertebral implant to designate both cages and prostheses, and also osteosynthesis plates. When particular embodiments of intersomatic cages require reference to specific technical features of cages, however, reference may be made to an intersomatic cage rather than to an intervertebral implant.

Various intervertebral implants (2) described herein comprise at least one peripheral wall (28), a posterior portion of which (in accordance with the conventions adopted in this description) comprises at least one passage (21) of suitable dimensions to receive at least one anchoring device (1) configured according to the invention. As explained elsewhere herein, the passage is may be straight to avoid the complex and expensive machining of a curved passage. However, with an implant separable into two parts at the passage joinable together, it is easier to create a curved passage. Moreover, it is possible to manufacture implants, such as intersomatic cages, by moulding. It is then possible to more easily produce implants having a curved passage, for example by using a mold with a curved insert. In addition, certain recent techniques allow curved machining, especially in solid materials (for example metals). Therefore it is possible, particularly in the case of intervertebral disc prostheses whose plates are made of metal, to create a curved passage designed to receive the curved anchor without much additional expense and burden over machining a straight passage. If passage (21) in the implant is curved, its height can be generally equal to (or very slightly greater than) the thickness of anchor plate (10). If passage (21) is rectilinear (straight), its height preferably will be at least slightly greater than the thickness of the curved anchor to permit it to pass without deformation of anchor (1) despite its curvature and its rigidity, as discussed elsewhere in the present application. This technical feature of a curved passage (21) within the implant allows many embodiments of objects such as implants and anchoring devices and/or systems in which the implant comprise a curved passage and in which the anchor is curved and may, but need not, comprise at least one rib (11). The implants and instruments which may be associated with anchors configured without a rib need not comprise a groove (211, 3011). These particular objects (i.e., any of these embodiments comprising or associated with a curved passage in the implant) may be configured to solve the problems of facilitating the guidance of anchor and fixation of implant (which may be linked to the problem of the stability of the anchor). In particular because the structural adaptations that may be required by such isolation or combination of features are directly derivable from the appreciation of the present disclosure, these particular objects may or may not also comprise any technical feature (or combination of technical features) described for any element (or combination of elements) of any object (or combination of objects) disclosed in this application, as long as they are not incompatible (such as for example a rigid anchor having a straight body is incompatible with such a curved passage).

In some embodiments, passage (21) in implant (2) as discussed elsewhere herein may comprise at least one groove (211) of complementary shape and size to at least one rib (11) disposed on the anchor. However, anchors (1) having no rib (11) are possible.

In some embodiments (not shown), passage (21) may have an entrance with an oblique orientation, in which the width of the passage is neither oriented parallel to the plane of the disc space, nor oriented parallel to the axis of the spine, but intermediate and forming an angle with these reference orientations (which are shown in most of the figures). In these embodiments, it is preferable to have two anchors (1) implanted in the same vertebra, and these anchors (1) preferably have a curvature in the thickness of the plate and one or more radius (or radii) of curvature shorter than generally used for anchors which may be associated with implants having an entrance of the passage oriented vertically or horizontally, so that the anchor has a curvature sufficient to provide a good hold despite its oblique orientation. This oblique orientation may be useful in various circumstances to address the problem of the stability of the anchor and the implant when faced with various constraints of the implantation. Some embodiments may provide, for example, two such anchors associated with an implant comprising at least two passages with such oblique orientation directed toward the same vertebra, but with opposite orientation one in relation to other (for example, one entrance inclined 45° to the right, and the other inclined 45° to the left). These various embodiments may not need a rib (11) on the anchor (1), nor a groove (211) in the passage (21) of the implant (2) (nor groove (3011) in the instrument). These particular objects (i.e., any of these embodiments comprising or associated with at least one passage (21) which entrance has an oblique orientation) may or may not also comprise any technical feature (or combination of technical features) described for any element (or combination of elements) of any object (or combination of objects) disclosed in this application, as long as they are not incompatible, in particular because the structural adaptations that may be required by such isolation or combination of features are directly derivable from the appreciation of the present disclosure.

The use of an anchor comprising a curved plate can be particularly advantageous with an osteosynthesis plate, in particular in the case of the disc space between vertebrae L5 and 51, because the orientation of the sacrum toward the back of the spine makes it generally difficult to access this area, even by an anterior approach. In general, even with a curved anchor (1), it is preferable to use an approach axis of the instrumentation that is oblique (not perpendicular to the vertebrae) at the level of the sacrum, because of the orientation of the latter toward the back of the spine. The contact surface with the implant at the anterior end of the instrumentation may be inclined with respect to its longitudinal axis (antero-posterior according to the convention used in the present application) for allowing an optimal contact with the osteosynthesis plate. Nevertheless, the approach axis may be substantially perpendicular to the osteosynthesis plate in some circumstances and the instrumentation will then be adapted to this approach axis. Furthermore, it is also possible to use an anchor comprising a straight plate, so as to allow this implantation in various circumstances (e.g., oblique path or path perpendicular to the vertebrae). The instrumentation will thus be adapted according to the shape of the anchor and the approach axis chosen. Implants devised with various features according to the invention may include osteosynthesis plates comprising a passage (21), with or without a groove (211) depending on whether the anchor (1) comprises a rib (11) or not. The peripheral wall (28) then corresponds to osteosynthesis plate itself, forming a wall between the exterior and interior of the disc space. The anchor is then inserted into the passage along an approach axis substantially perpendicular to the osteosynthesis plate (and the axis of the spine at the level of the disc space concerned). The passages (21) in the plate can be arranged to be placed at the disc space or vertebral body level and lead to the endplates or directly in the periphery of the vertebral bodies. The orientation of the entrances of the passages (21) may be oblique as explained above, especially if the anchor (1) does not contain a rib (11). These fixation plates can be further fixed against the vertebrae with conventional screws, in addition to at least one anchor as described herein.

It is noted that, in a general manner, passages, holes, notches, stops, recesses, lugs, and other elements of the various objects of the invention (anchors, anchor systems, implants, and instruments) may be formed by various methods, such as machining, drilling, casting, welding, etc., and the examples given herein are not to be construed restrictively.

As noted elsewhere herein, the anchor (1) may comprise at least one rib (11) on at least one part of at least one of its faces, and may comprise plural ribs (11) disposed on the same or opposite faces. Passage (21) of the implant for each anchor may therefore comprise several grooves (211), when needed to accommodate plural ribs on an anchor. An implant can be fixed by means of several anchors, and it will therefore comprise several passages (21), each comprising one or more grooves if anchors with one or more ribs (11) are to be used. Preferably, there will be two passages (21) each oriented toward a different one of the vertebrae between which the implant must be implanted. Thus, in certain embodiments, peripheral wall (28) comprises two passages (21) each oriented toward one of the upper and lower surfaces of implant (2) (vertebral contact surfaces of the implant), so as to anchor anchoring device (1) in each of the vertebrae between which implant (2) is designed to be implanted. Passage (21) of an anchor (1) is created in wall (28) of the implant so as to emerge on the vertebrae contact surface of the implant. In certain embodiments, peripheral wall (28) of implant (2) comprises two superposed passages (21) (FIGS. 2C, 2D, 3H, 4B-H, 5C, 7A, 7B, and 8A-C) or offset passages (FIGS. 3B, 3E, 3K, 4A, 5A, 5B, 13A, and 13D), each oriented toward one of the upper and lower surfaces, so as to anchor anchoring device (1) in each of the vertebrae between which implant (2) is designed to be implanted. In other embodiments, implant (2) comprises only one passage (21). Embodiments of prostheses similarly may have only one plate that comprises a passage (21), and the other plate does not.

Before anchoring device (1) is implanted to hold implant (2) in position, there is sometimes a risk that implant (2) will move in the disc space. In certain embodiments, therefore, at least one of the (upper and/or lower) vertebral contact surfaces of implant (2) may comprises notches (25) preventing movement of implant (2) between the vertebrae. In the case of an intervertebral disc prosthesis, it is also possible to provide stabilization means on the surfaces designed to be in contact with the vertebrae, such as notches or fins or any type of structure preventing it from moving between vertebrae, so as to ensure (or improve) the stability of the prostheses before its fixation by anchoring device (1). According to different embodiments, these notches (25) or other stabilization means can have different orientations. For example, notches (25) can be substantially parallel to one another and all oriented perpendicular to the implant insertion axis, or notches (25) can, on the contrary, have different orientations on different portions of implant (2), so as to prevent movement in various directions. As is particularly visible in the top views (FIGS. 2E, 5D, 7C, 8G, 9D, 10D, 10E, 10F, 11C, 11D, 12A, 13B, 13E, 15A, 17A, 17B, and 17C) of examples showing an intersomatic cage, the notches can be arranged substantially in a chevron pattern, relatively optimal for opposing movements in most directions, and, in particular, movements perpendicular to the anteroposterior axis in these examples of cages with lateral insertion (i.e., movements along an axis in a sagittal or para-sagittal plane of the spine).

It is noted that in various figures of this application, examples of cages represented include notches on almost their entire vertebral contact surfaces, but not on the peripheral wall of the cage. The posterior part of the vertebral contact surfaces of the cage has no notches in these examples. However, it is possible in various embodiments to provide notches on this and other peripheral parts, provided they do not interfere with the various stops, ribs, and/or other elements and features that may be configured on these implants and/or the anchors that may be associated with them.

For a cage (e.g., 2A, 2B), peripheral wall (28) can define a cavity (26), opened on the upper and lower surfaces of the implant (those in contact with the vertebrae) designed to receive a bone tissue graft or a substitute. Although an intersomatic cage can comprise a cavity (26) in its center defined by its wall (28), as shown in the figures of the present application, a cage may also consist of a solid piece without an inner cavity in other configurations within the scope of the invention. This type of cage can be designed to be used at least in pairs, for example, so as to define a cavity between the cages such as is known in the prior art. Moreover, in the case of cages with at least one cavity, and as particularly visible in certain examples shown in FIGS. 1, 2C, and 2, openings (24) can be created in wall (28) of the implant (the lateral walls in the examples shown), so as to also permit the growth of bone tissue transversely through the disc space (i.e., through the cage, parallel to the vertebral endplates). In certain embodiments, not shown, the intersomatic cage may comprise a reinforcement crossing its cavity (26) from side to side to reinforce wall (28) of cage (2). This reinforcement can have different shapes and orientations and can be oriented along the axis of insertion of cage (2) between the vertebrae, for example, or along another axis. In various embodiments, the reinforcement can have a lower height than the rest of the cage. This lower height of the reinforcement with respect to the rest of the cage permits the cage to take on various possible irregularities in the shapes of the vertebral endplates. The reinforcement may or may not be provided with notches (25). On the other hand, in certain embodiments, a part of passage (21) emerges into cavity (26). Generally, the wall can be dimensioned as a function of passage (21), and passage (21) will be dimensioned and oriented as a function of anchoring device (1) in order to orientate and hold this device in the direction of the vertebra into which the anchoring device must be affixed. Moreover, the orientation can be chosen as a function of the desired fixation, as mentioned elsewhere herein (for example, by means of the curves selected for the anchors). Note, however, that the implant dimensions vary as a function of the vertebrae between which they are designed to be implanted and that the dimensions of the anchoring device can also be adapted to those of the implant as a function of those vertebrae.

The form of the implant, even at the level of passage (21), is not limiting, as long as it allows at least one anchor (1) to be introduced. For example, cage (2) represented in the figures of the present application and particularly visible in the top views (FIGS. 2E, 5D, 7C, 8G, 9D, 10D, 10E, 10F, 11C, 11D, 12A, 13B, 13E, 15A, 17A, 17B, and 17C) has a substantially oblong periphery, except at passage (21) where the wall is substantially planar and near which it will be held by an instrument (3, 4). Even in these examples, however, it is not necessary that the wall be generally planar in this area, although it is generally preferred. Note that in various illustrated intersomatic cages, the substantially oblong shape has a slight curve (especially visible in the top views), but again, this shape is not restrictive with respect to the scope of the invention. Various top view figures, in particular FIGS. 19A to 19H, show that various forms of intersomatic cages may have a peripheral wall (28) including a slightly concave (283) side face (or surface), a slightly convex (284) side face (or surface), a substantially flat (281) posterior face (or surface), and a curved front (282) face (or surface), but again, this shape is not restrictive with respect to the scope of the invention. This "bean" shape, and especially the lateral (284) slightly convex side, substantially corresponding to the anterior portion of various vertebrae (for cages with a lateral approach axis), can support the edges of the endplates having a denser bone tissue. It is preferable that the shape of the implant be selected according to the shape of vertebrae between which it will be implanted and to the axis of the anatomical pathway foreseen for its implantation. For some illustrated configurations, this curved shape is preferred because the cage is arranged for being inserted laterally (or by a trans-psoatic approach or by a retro-psoatic approach) and allows the cage to have a form offering the best stability once implanted in a coronal orientation (i.e., with its longitudinal axis in the coronal plane, also called front plane). As noted, the cage could have other shapes, preferably chosen for the expected use and insertion approach. For example, the cage may not be curved, notably in the case of implantation by an anterior approach, or may be even more curved, notably in the case of an implantation by the transforaminal route.

Generally, the shape of implant (2) can vary and the shape of the end of instrument (3, 4) that will be in contact with implant (2) can consequently vary in various embodiments. Implant (2) can in fact have different shapes, as long as it has at least one passage (21) suitable for insertion of anchoring device (1) and preferably fastener (or attachment resources) (22) designed to cooperate with one end of an implantation instrument. Fastener (22) can, depending on the various particular embodiments, be associated with a particular shape of the implant near this fastener (22) to provide good cooperation with the instrument, or even have a particular shape cooperating with a complementary shape of the instrument. For example, the instrument can comprise a contact surface following the shape of the implant.

As previously mentioned, intersomatic cage (2) may or may not comprise a cavity (26) in its center, particularly if several intersomatic cages (2) are to be implanted in a same intervertebral space. Cages thus implanted are generally used to enclose bone tissue (graft) that will grow inside the intervertebral space and allow fusion (arthrodesis) of the two vertebrae between which it is implanted. Using a substitute instead of a bone graft is also known. In all cases, the purpose of cage (2) is to restore or maintain a space between the vertebrae. Before the growth of the graft and fusion of the vertebrae, cage (2) must remain properly in place in the disc space, and various embodiments of the present invention facilitate its immobilization. Similarly, a prosthesis typically must be immobile in all cases.

In certain embodiments, at least one portion situated around the center of the implant along the anteroposterior axis (which may correspond to longitudinal axis L) is thicker than the rest of the implant, so as to take on the shape of the vertebrae. As seen for example in FIGS. 3A, 3D, 3G, and 3J, the center of the implant may be thicker than its ends. Preferably, only the upper surface is convex since only the lower surfaces of the vertebrae generally have a concavity.

Figure 19A:
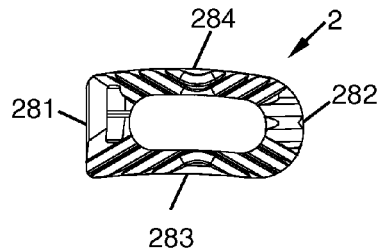
FIG. 19A is a top view of one of various embodiments of an implant, FIGS. 19B and 19C, respectively, showing a side view and front view of one of various embodiments of a scoliosing and lordosing implant, FIG. 19D showing a rear view of an embodiment of a lordosing implant, FIGS. 19E and 19G each showing a rear view of two of various embodiments of non-lordosing implants, and FIGS. 19F and 19H each showing a view of two of various embodiments of scoliosing implants.
Figure 19B:
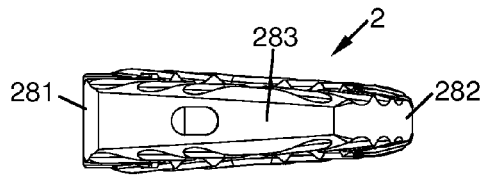
Figure 19C:
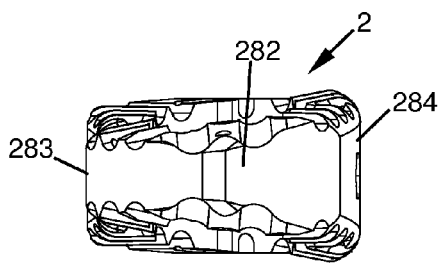
Figure 19D:
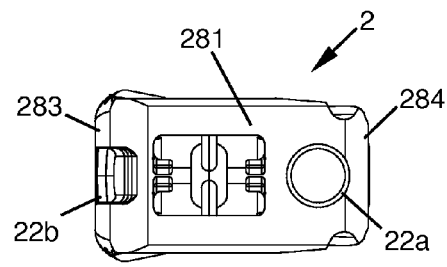
Figure 19E:
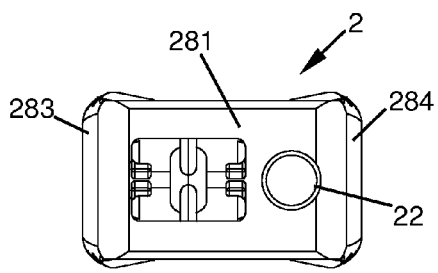
Figure 19F:
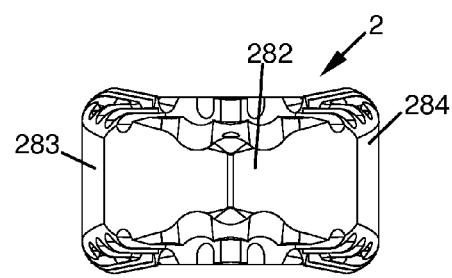
Figure 19G:
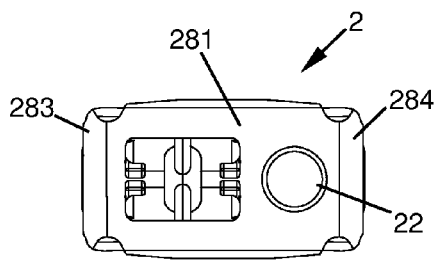
Figure 19H:
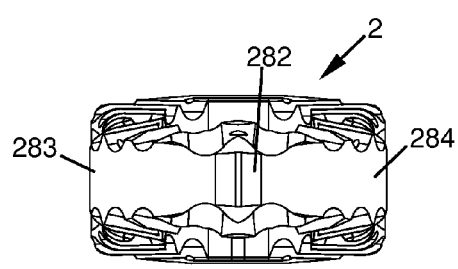

In certain situations, notably depending on the vertebrae between which implant (2) must be implanted, it is desirable for implant (2) to impose, accommodate, or correct lordosis, kyphosis, or even scoliosis, in addition to maintaining the space between the vertebrae. Certain embodiments therefore provide that the mean planes passing through the upper and lower surfaces of implant (2) (of the cage or at least one of the plates of the prosthesis) form an angle in at least one direction imposing, accommodating, or correcting lordosis, kyphosis, or scoliosis with respect to the vertebrae between which implant (2) is implanted. This general approach is described, for example, in applications FR 2,869,528 (and WO 2005/104996 and US 2005/0246024) and FR 2,879,436 (and WO 2006/120505 and US 2006/0136063), each of which is incorporated herein by reference, in particular concerning the technical features allowing such inclination of the mean planes of the implants (i.e., thanks to an angle between the mean planes of at least one plate or between the contact vertebral surfaces of a cage, and/or thanks to an asymmetric nucleus and/or to an offset position of the nucleus). Reference to the mean plane reflects herein that the (upper and lower) vertebral contact surfaces are not necessarily planar, since they can be provided with notches or can be convex or even concave; therefore a mean plane is intended to reflect the general orientation that a vertebra resting on the surface will take. For example, several of the intersomatic cages (2) shown in the figures of the present application are lordosis-inducing cages—they are designed to be inserted laterally and their portion intended to be positioned on the anterior side of the vertebrae is thicker than the opposite portion. In fact, as is particularly visible in FIGS. 3B, 3E, 3H, and 3K, it is seen that the cage is thicker on the left than on the right. Note also that in these FIG. 2, notches (25) are visible only on one of the lateral sides (the left side) of the cages, since the cages are lordosis-inducing. Notches situated on the side where the cage is thinner (the right) are present, but do not appear to project in the figure since only their upper end is visible. Although certain embodiments have the mean planes passing through the upper and lower surfaces of implant (2) forming an angle, straight cages can be provided, which typically would thus be symmetrical and have the medial planes passing through the upper and lower surfaces of implant (2) configured substantially parallel to one another. Depending on the desired implantation route for the implant, an angle may be imposed in various directions. For kyphosis and lordosis, this direction is anteroposterior with regard to the spine, with either a thinning of the implant toward the front of the spine to impose kyphosis, or a thinning of the implant toward the rear of the spine to impose lordosis. To impose scoliosis, the mean planes passing through the upper and lower surfaces must form an angle along the other direction of the plane of the disc space (along a frontal or coronal direction, i.e., along an axis oriented mediolaterally with respect to the spine) with a thinning of the implant toward the right or the left, depending on the desired effect. For example, FIGS. 19B and 19C represent a cage for imposing lordosis and scoliosis: the front face (282) of the wall (28) of implant (2) is thinner than its back face (281), as particularly visible in FIG. 19B, and the concave side face (283) is thinner than the convex face (284), as particularly visible in FIG. 19C. In this example, the sides may not be curved, as mentioned elsewhere herein, and it should be noted that the various features of this cage (e.g., the location of passages 21) are configured with respect to the specific insertion approach intended for this cage, which may change if a different approach is intended. As explained elsewhere herein, symmetrical implants may also be used, for example such as the cages of FIGS. 19E and 19G which side faces (283, 284) generally have the same thickness (side to side). The symmetry of implants may concern the back to front orientation and/or the side to side orientation. FIG. 19F shows a no-lordosis and no-kyphosis cage, in which the two sides (283, 284) have the same thickness, but this cage does impose scoliosis because its front surface (282) is thinner than its back surface (281). Again, note that for the cage of FIG. 19F to address scoliosis, it would be inserted through a lateral approach. The same applies to the example of the cage of FIG. 19H. It will be noted that the side faces (283, 284) of the cage of FIG. 19H are both concave, while the side faces (283, 284) of the cage illustrated in FIG. 19F are both convex. These illustrative and not limiting examples show the variety of shapes and configurations of implants, within the scope of the invention, that may be used depending on the application foreseen. For an inclination (e.g., scoliosis, lordosis, kyphosis) of adjacent vertebrae, it generally may be preferable for the width of the anchor to be oriented substantially perpendicular (or oblique, but not parallel) to the direction of inclination to provide good resistance to movements and to the forces exerted by the inclination. For example, for a cage for a scoliosis application (imposing a sideways inclination of the vertebrae), configured to be inserted by a lateral approach, an anchor (1) with a curvature of its plate (1) oriented in the depth of the plate will be preferred (e.g., FIGS. 2G, 2H). Conversely, for a cage for a lordosis/kyphosis application (imposing a back to front inclination of the vertebrae), configured to be inserted by a lateral approach, an anchor (1) with a curvature of its plate (1) oriented in the width of the plate will be preferred (e.g., FIG. 13G).

In certain embodiments, the peripheral wall (28) comprises, at the level of an anterior part (using the direction conventions noted elsewhere herein), at least one beveled portion (27), for example, at least one chamfer on at least one peripheral portion of at least one of its upper and lower surfaces, so as to facilitate the insertion of implant (2) between the vertebrae. As is particularly visible in the example of the intersomatic cage of FIG. 1, the anterior end of the cage has substantially the shape of the point of a shell (bull-nose, mortar), to optimize the penetration of the cage between the vertebrae, especially when the space between said vertebrae is insufficient. Chamfer or bevel (27) may be present on both the lower and upper surfaces of implant (2). This chamfer (27) or beveled profile facilitates implanting implant (2) by conferring to it a somewhat lower height on its attack side (the one designed to be inserted first) than on the rest of the cage.

As explained in this disclosure, the various configurations or embodiments of implants (2) preferably will be adapted to the configurations or embodiments of anchors (1), in particular for the retaining stops (14) and/or the withdrawal stops (12). Thus, in certain embodiments, passage (21) comprises at least one stop (214) having at least one stop surface generally facing the outside of implant (2), arranged for cooperating with at least one retaining stop (14) of anchoring device (1) to hold the implant (2) once anchoring device (1) is fully anchored in a vertebra through passage (21). As mentioned elsewhere herein, for various configurations of the anchor, stop (214) may be situated either above and/or below the passage, to receive lugs projecting above and/or below the anchor, or on the lateral sides of passage (21) so as to receive two projecting lugs on the sides of the body of anchoring device (1), or any combination of these possibilities. Preferably, there will be 2 stops in each case. Preferably, stop (214) is a recess, the bottom of which forms the stop surface, with depth sufficient to receive retaining stop (14) without it protruding from peripheral wall (28). In certain embodiments, the implant comprises at least one withdrawal stop (212) having at least one stop surface generally facing the anterior end of the anchoring device inserted in passage (21), this withdrawal stop (212) cooperating with at least one withdrawal stop (12) of anchor (1), such as a flexible lug (12), in order to oppose the withdrawal of anchoring device (1) from implant (2).

In certain embodiments, an instrumentation (3, 4) may be used to insert implant (2) between the vertebrae and to guide anchoring devices (1) into the implant (2) and drive the anchoring devices (1) into the vertebrae. In these embodiments, peripheral wall (28) of implants (2) preferably comprises at least one fastener (or attachment resources) (22) arranged for cooperating with a gripping end of an implantation instrument (3, 4). Thus, various embodiments of potential objects of the present invention concern implantation instruments (3, 4) for the implantation of intervertebral implants (2) and of anchoring device (1) to affix implant (2) against at least one vertebra. In various embodiments, the instrument is adapted to anchoring device (1) in order to affix this device in the vertebrae and also to intervertebral implants (2) configured according to the invention, comprising at least one fastener (22) (or attachment resources) for an implantation instrument (3) so as to enable the implants (2) be gripped or held by the instrument (3). In some configurations, the fastener of implant (2) may comprise at least one recess (22) as shown, for example, in FIGS. 3B, 3E, 3H, 3K, 4(A to H), 5(A-B), 13A and 13D, designed to receive at least one gripping resource (321) of the instrument. For example, an opening (22) can receive the end of a shaft (321) of an instrument. Opening (22) can be threaded to cooperate with a threading on the end of shaft (321), as particularly visible in the examples of FIGS. 16A and 16B, also showing other additional fasteners or attachment resources. However, the fastening means can also comprise a portion projecting outside the implant designed to be inserted into a recess of a gripping means (not shown). In certain embodiments, fasteners or attachment resources (22, 22a, 22b, 22c) can also comprise arrangements formed at least in part by the different surfaces of the implant, with gripping resources of the instrument having a shape complementary to these surfaces to allow gripping the cage or prosthesis. For example, the first fastener may comprise an opening (22a) in posterior wall (28) of the implant, receiving a shaft (321) of instrument (3), and may be complemented by a recess (22b) in one of the walls (lateral wall, for example, in these figures) of implant (2), as particularly visible in FIGS. 2C, 2D, 5C, 8A-C, and 15F. As particularly visible in FIGS. 16B, 16C and 17A, also showing another additional fastener, this recess (22b) is designed to receive a lug (3210) of a complementary shape of instrument (3). This double grip permits better holding implant (2) during implantation between the vertebrae and in particular, exerting torsion on the implant, for example, by offering a lever arm between gripping resources (22a-321 and 22b-3210). This double grip can also be improved by a third resources or arrangement (22c), formed in the second resources or arrangement (22b), as is particularly visible in FIGS. 1, 7A, 7B, 16B, 16C, and 17A. For example, the recess (or reinforcement) (22b) in a wall of the implant can also comprise another recess (a hole, a notch, etc.) designed to receive a complementary stud (3210b) created on lug (3210) of the instrument (or a pin, lug, tab or any other projecting structure). In this example, as particularly visible in FIGS. 16B, 16C, and 17A, implant (2) is engaged by instrument (3) by inserting stud (3210b) and lug (3210) into their respective recess (22c and 22b, respectively), then implant (2) is "locked" on instrument (3) by means of shaft (321) which is mounted so as to slide on instrument (3) and can be tightened, if necessary. Thus, although implant may comprise at least one complementary fastener (22) of at least one gripping resources (321) of instrument (3), the grip may be improved with one or more additional fastener (e.g., 22a, 22b, 22c) complementary to each of gripping resources (321, 3210, and 3210b, respectively) of the instrument. Note that the term "grip" should not be interpreted in a limiting manner as referring only to a structure that generally comprises two elements forming a gripping component, but rather its use in the present disclosure refers simply to the fact that that the indicated structure serves to hold the implant. Preferably, fastener (22) will be located near passage (21) to allow gripping implant (2) by the instrument near the place where the anchoring devices will be inserted, so as to reduce the size of the assembly and to improve the retention of the implant by the instrument, in particular when the anchors are implanted in the vertebrae, which generally requires tapping on the anchors (by means of impactor (4) described below). Furthermore, as particularly visible in the figures showing various embodiments mentioned herein, the position of the fastener can vary as a function of the size of the posterior wall of the implant, the configuration of the anchors, and the size of the implant. Preferably, the configurations of the anchors, implants, and instruments are interdependent and complementary.

Generally, an instrumentation (3, 4) for implanting intervertebral implant (2) between vertebrae and implanting at least one anchoring device (1) in at least one of these vertebrae, configured in accordance with the invention, preferably will comprise at least one impactor (4) comprising a head (44) of suitable shape and size to press anchoring device (1) and at least one guide (3) elongated along a longitudinal axis extending between a gripping end for implant (2) and a pressing end. In various configurations, guide (3) comprises a head (30) of suitable shape and size to receive head (44) of the impactor at least partially and at least one guide surface (31). Preferably, because curved anchors are preferred, the guide surface (31) will have at least one radius of curvature substantially identical to at least one radius of curvature of an anchoring device (1), so as to guide this anchoring device (1) through passage (21) of implant (2), to impact anchoring device (1) into a vertebra (preferably into the vertebral endplate). In certain embodiments, head (30) comprises at least one groove (3011) created for the passage of at least one rib (11) of anchoring device (1). Depending on the face or faces on which rib or ribs (11) are found, groove or grooves (3011) will be configured in guide (3) appropriately for the passage of the rib (or ribs). In certain embodiments, groove (3011) created for passage of rib (11) of anchoring device (1) is created on at least a part of the upper wall and/or the lower wall of cavity (300) of head (30) of guide (3).

Generally, in various configurations head (30) of guide (3) comprises a cavity (300) of suitable shape and size to receive anchoring device (1) and at least partially receive head (44) of impactor (4), with guide surface comprising at least two curved grooves (31, FIG. 17D) situated oppositely on the sides of cavity (300) to receive and guide the lateral sides of anchoring device (1) on both sides of body (10), with head (44) of impactor (4) penetrating into cavity (300) from one end to the other of these grooves (31).

In some configurations, the rib (11) of the anchor will help guide the implant through head (30). A head (30) of the guide (3) comprising a groove (3011) for the passage of the rib (11) serves to guide the anchor (1) and generally will be preferred. The impactor is arranged to pass into the head (30) of the guide, and in some configurations the walls of the cavity (300) may be configured to guide the impactor.

Figure 17A:
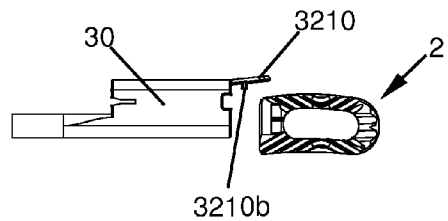
FIGS. 17A, 17B, 17C, 17D, and 17E show partial views of the gripping end of one of various combinations of embodiments, showing respectively a top view of a guide approaching an implant, a top view of a guide holding an implant, a top view of a guide holding an implant provided with a pair of anchoring devices, a sectional view along plane 17D-17D of FIG. 17C of the guide holding the implant provided with a pair of anchoring devices (one shown in place and the other shown inside the guide, about to be implanted), and a perspective of the guide holding an implant provided with a pair of anchoring devices.
Figure 17B:
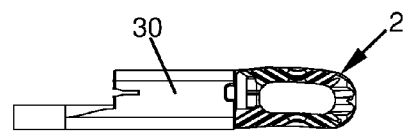
Figure 17C:
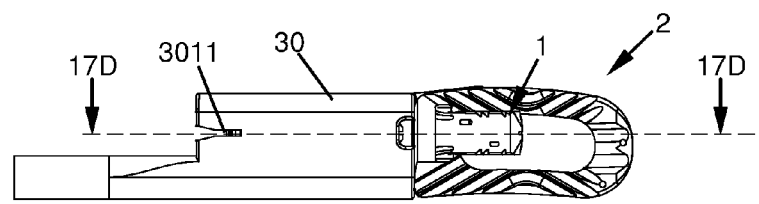
Figure 17D:
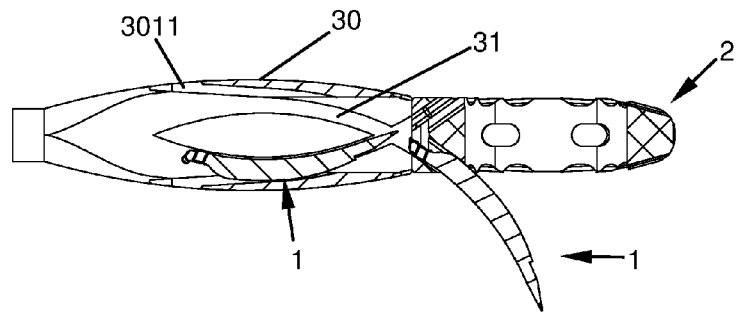
Figure 17E:
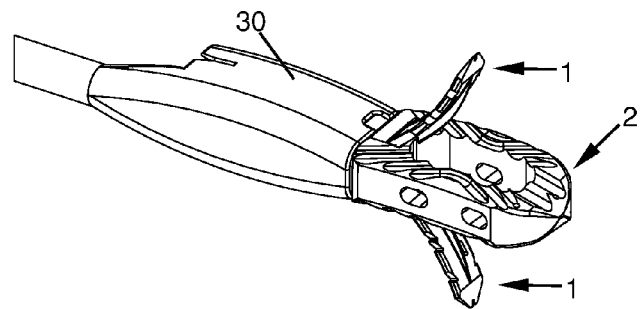

Various configurations of the instrument allow a surgeon to load anchors for implantation even with the implant already mounted on the guide, and even with the implant already implanted in an intervertebral space (wholly or partially). For example, the guide (3) can be configured for allowing the loading of anchor through the back of the head (30). In addition, the ability to load anchors through the back of the head (30) helps reduce crowding in the surgical opening. To reduce the size of the surgical opening required, in various configurations of the instrument preferably the height of the head (30) is reduced as much as possible, while still providing an appropriate path for the insertion of the anchors into the implant. Preferably, the head will have a maximum height approximating the height of the implant. If grooves (3011) are present in the head, a bit of additional height may be necessary, for example as shown in FIG. 17D. Then, grooves (3011) extending to the exterior of the head (as shown in FIG. 17D, for example) may be particular useful in such cases. In some embodiments, however, the cavity (300) is high enough to allow passage of the anchor (with or with a rib) without needing grooves (3011). Nevertheless, the use of grooves (3011) may be beneficial anyway, to provide enhanced guidance and stability of the anchor while it is being inserted into the implant and the vertebra.

In configurations having the head (30) of the guide approximately the same height as the implant or shorter, at least one stop may be provided near the anterior end of the guide. Such stop may, for example, be adjustable and/or fixed on the head or elsewhere on the body (tube, handle, head, etc.) of the guide (3), and prevent the guide from penetrating too far into the disc space, especially during the impaction of the implant and/or the anchor (1).

In various configurations, the instrument comprises at least one gripping resource (321) designed to cooperate with at least one fastener (22) of implant (2). The presser end may, in some embodiments, comprise a handle (320) used for pressing the guide holding implant (2) to insert the implant (2) into the intervertebral space. As is particularly visible in FIG. 16B, this handle can comprise a passage for shaft (321), which in this configuration is connected to a wheel (33) for screwing into the implant (comprising a threaded hole as an attachment resource). The surgeon can tap on handle (320) and/or wheel (33), for example using a hammer or by means of another tool of known type, to drive implant (2) between the vertebrae and into the intervertebral space. Upon fully appreciating this disclosure, a person skilled in the art will understand that some of various elements and technical features of instrumentation (3, 4) can be present on or absent from the instrumentation which may still be used with various embodiments of implants (2) or anchoring devices (1).

Guide (3) comprises an elongated body (32) allowing delivery of the cage to the intervertebral space without needing too much space. This guide body (32) guides and/or houses shaft (321) that grips implant (2). Impactor (4) also comprises an elongated body (42), that can slide with respect to body (32) of guide (3). This elongated body of impactor (4) can be formed by a shaft (42) sliding with respect to guide (3) when it is activated by handle (41). As is particularly visible in FIG. 16, this impactor body (42) can be guided in its slide along the guide by means of a groove (324) created at the bottom of an opening (322) of handle (320) of guide (3). In certain embodiments, such as particularly visible in FIG. 16B, wheel (33) of the guide is notched to allow passage of the impactor body. In these embodiments, the wheel can be indexed, for example by means of a ball (325) inserted into a recess and held compressed against wheel (33) by elastic resources (326) (such as a spring, for example), so that it can only be stopped in the positions where the notches of the wheel face groove (324) for guiding body (42) of impactor (4).

In certain embodiments, impactor (4) comprises a handle (41) that allows sliding impactor body (42) with respect to guide (3). This handle can also be tapped on by the surgeon, for example with a hammer or by means of another tool of a known type, to drive anchoring device (1) into a vertebra through the implant. Moreover, in certain embodiments, impactor (4) comprises at least one stop (43) limiting the penetration of head (44) of impactor (4) inside head (30) of guide (3). In certain variants, this stop can be adjustable along body (42) of impactor (4) so as to allow adjusting the penetration of the impactor to the size of head (30) of guide (3) and the size of the anchoring device (1) used. In fact, for example, as mentioned previously, the anchoring device (1) used can have a variable length depending on the clinical circumstances and guide head (30), and in particular curved guidance surface (31) will also have a size adapted to this length of anchoring device (1). Gripping resources (or arrangement) (321) holds implant (2) securely in place against guide head (30), with the anterior end of guide surface (31) aligned with and opening into passage (21) of implant (2) and the posterior end of guide surface (31) remaining accessible for insertion of anchoring device (1) for passage into the implant and then the vertebra. In certain embodiments, shaft (321) comprises a threaded end cooperating with a complementary threading of recess (22, 22a) to affix implant (2) when the shaft is activated by the guide handle or wheel (33). In certain embodiments, fastener (22) comprises a recess (22, 22a) and gripping resources (321) comprises an end of a shaft sliding in a body (32) of guide (3) when it is activated by a handle or wheel (33) to enter and leave recess (22, 22a) of implant (2). As already mentioned, in certain embodiments, fastener (22) may comprise recess (22a) and a groove (22b) on a lateral side of peripheral wall (28), with gripping resources (321) comprising one end of a shaft sliding in a body (32) of guide (3) when it is activated by a handle or dial (33) in order to enter and leave recess (22, 22a) of implant (2), and a lug (3210) arranged to be engaged in groove (22b) and serving as a lever arm for positioning implant (2) between the vertebrae. Moreover, in certain variants, groove (22b) comprises a recess (22c) designed to receive a stud (3210b) of lug (3210) so as to improve the grip of implant (2) by the instrument.

In certain embodiments, cavity (300) of head (30) comprises two guide elements (particularly visible in FIG. 17D), each comprising guiding grooves (31) and each situated on a side of cavity (300). In this example, the guide elements are joined with head (30) by inserting them inside cavity (300), which can comprise fastening resources for immobilizing these guide elements (310), such as pins, screws, clips and/or other fastening items. In other examples, head (30) may be made with integrally with guide grooves (31) directly inside cavity (300). In this case, the head may be made of two parts joined together, to facilitate machining curved grooves (31). However, machining curved guide surfaces (31) directly in the head is possible.

Figure 20A:
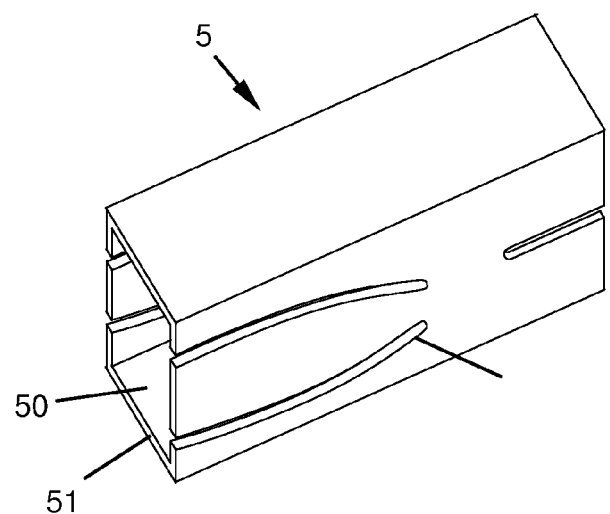
FIG. 20A shows a perspective view of one of various embodiments of an adapter and FIG. 20B shows a side view of one of various embodiments of an impactor penetrating in an adapter holding an anchor.
Figure 20B:
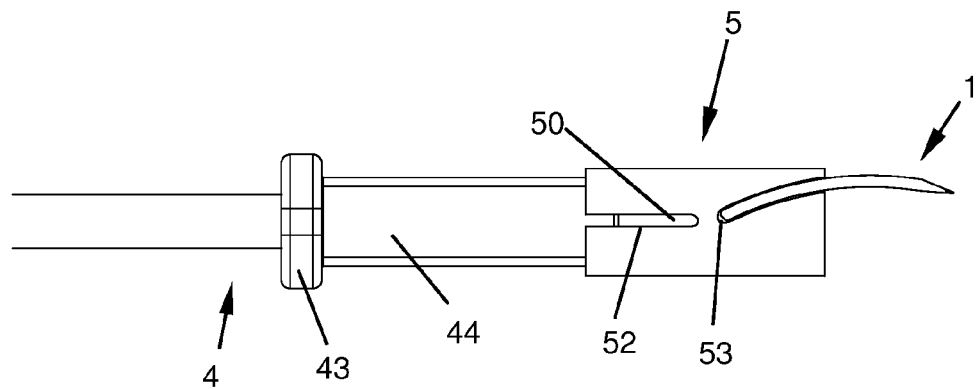

Other potential objects of the present invention concern an adapter (5, FIG. 20A-B) arranged for loading at least one anchor (1) in the head (30) of the guide (3). This adapter (5) is preferably arranged for holding at least one anchor (1) in an appropriate manner for the insertion of this anchor (1) in the head (30) of the guide (3). In various embodiments, this adapter (5) is hollow and open at its anterior and posterior ends (again according to the convention used in the present application), thus delimiting a cavity (50) open from end to end, forming a sort of conduit or channel (for example with a body substantially of a shape of a hollow rectangular parallelepiped open at its ends). In various embodiments, this cavity (50) is of shape and dimensions substantially identical (or at least close or similar) to those of the cavity (300) of the guide. Thus, the adapter (5) may be mounted on the impactor (4) which can pass through the cavity (50) therein. In some embodiments, for example, so that the adapter (5) holds on the impactor (4), the adapter (5) may be arranged so that the passing of the impactor (4) cause a slight deformation of the adapter (5) by configuring the initial dimensions of the inside of the cavity (50) of the adapter (5) to be slightly smaller than the size of the impactor (4) (and eventually also to those of the cavity of the guide), at least at the level of its posterior end (according to the convention used in the present application). The external dimensions of the adapter (5) will preferably be slightly larger than those of the cavity (300) of the guide (3), at least at the level of its posterior end (according to the convention used in the present application), so that it doesn't penetrate within this cavity (300) of the guide (3). For example, the wall (51) of the adapter (5) may be configured with at least one slit (52) facilitating its deformation. Furthermore, the material of the adapter may be arranged for allowing such deformation. In various embodiments, for example, the posterior end will be configured within the cavity (50) of the adapter (5), with at least one thickened (raised) portion (as a boss or a protruding part) for facilitating the holding of the adapter (5) on the impactor (4) and thus obtain dimensions of the entrance of the cavity (50) of the adapter that are slightly smaller than those of the impactor (4). Such a thickened portion may be combined with a slit and/or a deformable material of the adapter (5) for facilitating the passage of the impactor. The adapter (5) holding at least one anchor (1) may thus be mounted on the impactor (4) which is used to bring the anchor at the entrance of the cavity (300) of the guide's head, thanks to the arrangement of the impactor (4) and the guide (3) (the impactor being disengageable from the guide, for example via the opening (322) of the handle (320) of the guide), and then for pushing the anchor (1) within the head of the guide, while leaving the adapter (5) at the entrance of the cavity (300) of the guide (3). Furthermore, in various embodiments, the lateral sides of the cavity (50) of the adapter (5) comprise at least one groove (preferably at least one groove on each side, extending through at least one wall of the adapter or not, and straight or curved, according to the anchor used) arranged for holding and/or guiding at least one anchor (1), in a manner similar to the grooves (3011) of the guide (3), but preferably only on a (anterior) portion of the adapter. These grooves (53) of the adapter (5) are preferably arranged so that, when the impactor (4), cooperating with the body of the guide, brings at least one anchor (1) held by the adapter (5) to the head (30) of the guide (3), the anterior end of the anchor (1) is substantially facing the entrance of the grooves (3011) in the head (30) of the guide (3), such that the anchor (1) can penetrate in an adequate manner inside the guide (3). The grooves (53) of the adapter (5) are thus preferably a prolongation of grooves (3011) (i.e., either a prolongation of at least one arch described by these grooves (3011) of the guide (3), or a prolongation of the straight path of these grooves (3011) of the guide (3), according to the type of anchor used). It is noted that this type of adapter (5) may be particularly advantageous in certain embodiments in which two anchors (1) can't be inserted at the same time in the instrument, such as for example in the cases where the anchors (1) are curved along the depth of the plate (10) (anchors with horizontal orientation) and where the head (40) of the impactor (4) has dimensions such that it substantially fills the cavity (300) of the guide (3) and thus would push both anchors (1) at the same time, these two anchors (1) thus interfering each other inside the head (30) of the guide (3). Thus, in these cases, it is possible to introduce a first anchor (1) in the guide (3) holding the implant (2), to implant this implant (2) using the guide (3), and then to impact this anchor (1) in a vertebra using the impactor (4), and then to withdraw the impactor (4) for providing it with the adapter (5) holding a second anchor (1) and to insert the anchor (1) in the guide (3) and then to impact this anchor (1) in a vertebra using the impactor (4). It is noted that, conversely, in other embodiments, notably when the anchors (1) are curved along the width of the plate (anchors with vertical orientation), two anchors (1) don't interfere with each other in the head (30) of the guide (3) because their path don't cross each other. In these embodiments, such an adapter (5) may not be need, but may nevertheless be used. In these cases of anchors (1) with vertical orientation, the grooves (53) of the adapter (5) will be on the inferior and superior sides of the cavity (50) of the adapter (5) instead of the lateral sides. This type of adapter (5) allows the surgeon to introduce the anchor(s) later, if he wishes, rather than inserting the anchor(s) in the guide (3) when implanting the implant (2). Furthermore, in certain embodiments of the impactor (4), particularly corresponding to the cases where the anchors (1) are curved along the width of the plate (anchors with vertical orientation), the width of the impactor (4) may be configured to be only substantially half the width of the cavity (300) of the guide (3), so that the impactor (4) allows impacting only one anchor (1) at a time, instead of pushing both anchors (1) at the same time as when the width of the impactor (4) is substantially the same as the width of the cavity (300) of the guide (3). Thus, such an impactor (4) may be used for impacting a first anchor (1), and then for being turned so as to impact a second anchor (1). These various embodiments of adapters (5), anchors (1) and impactors (4) thus allow the implementation of various steps of methods for preparing the implantation and of method for implantation, according to the sequences described above for example.

Other potential objects of the present invention relate to various embodiments of methods of preparing for an implantation of, and/or methods for implanting, intervertebral implant (2) into an intervertebral space and for preparing the fixation of, and/or for fixing, the implant to at least one vertebra. These methods may comprise a step of assembling the implant (2) onto a guide (3), a step of placing the impactor (4) relative to the guide, a step of placing at least one anchor (1) in the guide (3). These various steps can be implemented in different orders, thanks to the arrangement of various objects of the invention, as described in various embodiments discussed in the present application.

In various embodiments, these methods for preparing the implantation may comprise:
 providing an anchoring device (1) in accordance with an embodiment discussed in this present application;
 providing an spinal implant (2) in accordance with an embodiment discussed in this present application;
 providing an implantation instrument (3, 4) in accordance with an embodiment discussed in this present application;
 gripping the spinal implant (2) with the implantation instrument (3, 4);

In various embodiments, these methods for preparing the implantation may further comprise a step of introducing at least one anchoring device (1) within the instrument (3, 4).

In various embodiments, these methods for implanting a spinal implant (i.e., for inserting the implant within a disc space or onto vertebrae) may comprise the steps of the methods for preparing the implantation and may further comprise:
 inserting the spinal implant (2) in an intervertebral space between adjacent vertebrae of a spinal column (or onto adjacent vertebrae of a spinal column in the case of an osteosynthesis plate);
 presenting the anchoring device (1) along an approach axis that is substantially perpendicular to the axis of the spine (at the level of the adjacent vertebrae);
 using the impactor (4) of the implantation instrument (3, 4), inserting the anchoring device (1) through the guide head (30) of the implantation instrument (3, 4) and through the passage (21) in the implant (2), with the anchoring device (1) traversing at least a portion of the implant (2); and
 using the impactor (4) of the implantation instrument (3, 4), implanting at least part of the anchoring device (1) in one of the adjacent vertebrae and fully inserting the anchoring device (1) in the implant (2).

In various embodiments of these methods for implanting a spinal implant, the step of fully inserting the anchoring device (1) in the implant (2) comprises abutting the retaining stop (14) of the anchoring device (1) against its complementary stop (214) within the implant (2).

Some embodiments of the methods for implantation of the present invention provide insertion of an implant along a lateral approach (i.e., along a trans-psoatic path, or along a retro-psoatic path). The trans-psoatic approach uses a path through the psoas, a muscle lateral to the spine. The retropsoatic path uses a path behind the psoas, by pushing the psoas to the front of the patient. In various embodiments of these methods for implanting a spinal implant, the step(s) of inserting the implant may thus comprise at least one step of cutting the psoas and a step of passing through the psoas. In various embodiments of these methods for implanting a spinal implant, the step(s) of inserting the implant may thus comprise at least one step of pushing the psoas and a step of passing behind the psoas. It will be noted that, depending on the case, the surgeon may also pass in front of the psoas.

Most technical problems solved by various technical features described in the present application may be related to the problem of stability mentioned in the preamble of this present disclosure. After appreciating this disclosure, a person of skill in the art may design various embodiments combining the following technical features, which are discussed below, in a non limitative manner, in relation to at least one of the problems mentioned in this application.

Each of these technical features or of these elements, described in at least one embodiment or configuration and discussed below, may be isolated from other technical features of the object concerned by (or the objects concerned by and/or associated with) said embodiment or configuration (and thus concerning the same or another element) and/or may be combined with any other technical feature described herein, in various embodiments or configurations, unless explicitly stated otherwise, or unless these features are incompatible and/or their combination is not functional, in particular because the structural adaptations that may be required by such isolation or combination of features are directly derivable from the appreciation of the present disclosure.

Stability of the anchor in the vertebrae and/or in the implant (and thus possibly the stability of the implant between the vertebrae):

Technical Features and Elements:

Rib (11): may be configured to stabilize the anchor in the vertebrae, but also may be configured to stabilize the anchor in the implant (including the groove (211) of the implant), which may further stabilize the implant.

thickened portions and/or plane surfaces (20, 110: 110*a* and/or 110*b*, 111) in the case of a curved anchor in a straight passage: may provide a snug fit of the anchor in the implant to help stabilize the anchor in the implant and may therefore stabilize the anchor in the vertebra, and therefore may further stabilize the implant.

Anchors "vertically oriented", i.e., curved in the direction of the width of the plate (10): may be configured to stabilize anchor in the vertebrae and thus may further stabilize the implant.

Locking anchor in the implant: also improves the stability of anchor in the implant and/or stability of the implant between the vertebrae (and/or stability of the anchor in the vertebra)

Technical Features and Elements:

Retaining stop (14): may retain the implant pressed against the vertebra thanks to the anchor planted in a vertebra. This stabilizes the implant on the vertebra but also may further stabilize the anchor in the implant and/or the vertebra.

Withdrawal stop (12): may retain/hold the anchor in the implant. This stabilizes the anchor in the implant and/or the vertebra and may further stabilize the implant between the vertebrae.

Cooperation Stops (18, 19): allow interlocking of 2 anchors in the implant. This stabilizes the anchor in the implant and/or the vertebra and may further stabilize the implant between the vertebrae. These Cooperation Stops (18, 19) further allow minimizing the necessary locking structures (and their size).

Removal of the anchor allows the intentional withdrawal of the anchor (and possibly the implant). This problem may be related to the stability of the implant (e.g., if it is not good). For example, the surgeon may reposition the implant for better stability:

Technical Features and Elements:

Retaining stop (14) accessible for intentional withdrawal:
  Complementary Stop (214) in the implant may be arranged to help pull on the retaining stop (14) of the anchor
  Housing (240) in the implant may be arranged for providing access to the retaining stop (14)

Cooperation Stops (18, 19) accessible for intentional withdrawal:
  Housing (40) in the anchor may be configured to provide access to at least one of the cooperation stops (18, 19),
  Housing (240) in the implant may be configured to provide access to at least one of the cooperation stops (18, 19), Withdrawal stop (12) accessible for intentional withdrawal:
  Housing (40) in the anchor may be configured to provide access to withdrawal stop (12),
  Housing (240) in the implant may be configured to provide for access to the withdrawal stop (12),
  Housing (40) in the anchor may be configured to provide access to at least one of the cooperation stops (18, 19) and/or withdrawal stop (12)
  Housing (240) in the implant may be configured to provide for access to at least one of the cooperation stops (18, 19) and/or withdrawal stop (12)

Guiding the anchor and fixing the implant facilitates the implantation of the implant and anchor and facilitates obtaining a good stability of the anchor in the vertebrae and/or implant (and thus possibly the stability of the implant between the vertebrae):

Technical Features and Elements:

A curved passage for a curved, rigid anchor helps guide the anchor through the passage and may be configured for minimal clearance of the anchor, which may provide a snug fit of the anchor in the implant to help ensure good stability.

A straight passage for a straight, rigid anchor can be configured to help guide the anchor through the passage, and have minimal clearance of the anchor, which may provide a snug fit of the anchor in the implant to help ensure good stability.

A straight passage for a curved, rigid anchor helps guide the anchor through the passage and may be configured for minimal clearance of the anchor, which may provide a snug fit of the anchor in the implant to help ensure good stability.

A curved passage curve for a straight, rigid anchor or an anchor with plural straight portions forming an angle between each other: helps guide the anchor through the passage and may be configured for minimal clearance of the anchor, which may provide a snug fit of the anchor in the implant to help ensure good stability.

Fixation of implant such as an osteosynthesis plate: The fixation of an osteosynthesis plate may be performed with a curved or straight anchor, along an approach axis preferably substantially perpendicular to the plate for the curved anchors or preferably substantially oblique with respect to this plate for the straight anchors, which improves the stability of the osteosynthesis plate itself (implant fixed). Furthermore, when used in combination with an intersomatic cage, an osteosynthesis plate improves the immobility of the spine and thus facilitates the stability of the cage. The plate-type implant improves the stability of a cage-type implant.

After fully appreciating this disclosure, a person skilled in the art will understand that numerous embodiments and/or configurations in various other specific forms are possible and within the scope of the invention. Consequently, the present embodiments and/or configurations should be considered as non-limiting illustrative examples that may be modified and still be within the scope of the attached claims, and the invention should not be limited to the details provided above.

The invention claimed is:

1. A system for treatment of a spine comprising:
   an anchor comprising
      a body comprising a rigid, elongated, curved plate having opposing edges extending between a first curved surface of the plate and a second curved surface of the plate, and
      a rib disposed along the plate between the opposing edges of the plate and extending between a first end of the plate and a second end of the plate; and
   an intervertebral implant comprising
      a vertebral contact surface,
      an exterior opening in a side of the implant adjacent to the vertebral contact surface, and
      a passage extending toward the vertebral contact surface and being configured to receive the anchor through the exterior opening of the implant, the passage comprising a groove configured to accommodate the rib when the anchor is received through the exterior opening of the implant,
   with the anchor having a deployed position in which the first end of the plate extends outside the passage and away from the vertebral contact surface, and the second end of the plate is disposed in the passage.

2. The device of claim 1 in which the passage is straight.

3. The device of claim 1 in which the passage is curved.

4. The device of claim 1 in which the body comprises a thickened portion configured for contact with an inner wall of the passage to stabilize the anchor in the implant.

5. The device of claim 1 in which the anchor has a latch configured to inhibit withdrawal of the anchor from the implant after full insertion of the anchor in the implant, and the implant has an access configured to permit releasing the latch after full insertion of the anchor in the implant.

6. The device of claim 1 in which the anchor has a latch configured to inhibit withdrawal of the anchor from the implant after full insertion of the anchor in the implant, and the latch comprises a resilient tab disposed along an edge of the rib.

7. The device of claim 1 in which the anchor comprises a connection disposed at an end of the anchor and configure to attach to an anchor-extraction tool.

8. A device for treatment of a spine comprising:
   an anchor comprising
      a curved, rigid plate that is elongated along a longitudinal axis extending between a first end of the plate and an opposite second end of the plate, the plate comprising:
         a first plate surface having a first plate width extending in a direction transverse to the longitudinal axis, the first plate surface being concave in a direction along the longitudinal axis,
         a second plate surface having a second plate width extending in a direction transverse to the longitudinal axis, the second plate surface being convex in a direction along the longitudinal axis,
         a first edge disposed between the first plate surface and the second plate surface and having a first edge height between the first plate surface and the second plate surface that is less than the first plate width and the second plate width,
         a second edge disposed between the first plate surface and the second plate surface and having a second edge height between the first plate surface and the second plate surface that is less than the first plate width and the second plate width, and
         a rib elongated along a direction substantially parallel to the longitudinal axis, the rib disposed between the first edge and the second edge and projecting from the first plate surface or the second plate surface, the rib having
            a rib length extending in a direction substantially parallel to the longitudinal axis, and
            a rib width extending in a direction transverse to the longitudinal axis, the rib width being less than the first plate width, the second plate width, and the rib length; and
   an intervertebral implant comprising
      at least one peripheral wall extending between a first vertebral contact surface and a second vertebral contact surface, and
      a passage in the peripheral wall configured to receive the anchor through an exterior opening of the passage disposed along the peripheral wall and project the anchor away from the first vertebral contact surface or the second vertebral contact surface without deformation of the plate.

9. The device of claim 8 in which first plate width and second plate width are substantially equal.

10. The device of claim 8 in which first edge height and second edge height are substantially equal.

11. The device of claim 8 in which the first edge of the curved plate comprise notches.

12. The device of claim 8 in which the rib has an edge defining a height of the rib from the first plate surface, and the height of the rib from the first plate surface varies along the rib length.

13. The device of claim 8 in which the rib has an edge defining a height of the rib from the first plate surface, and the rib comprises a segment in which the height of the rib from the first plate surface is constant along the rib length.

14. The device of claim 8 in which the passage comprises a slot configured to receive the rib when the passage receives the anchor.

15. The device of claim 8 in which the first plate width varies along the longitudinal axis.

16. The device of claim 8 in which the rib width varies along the rib length.

17. A spinal implant comprising
   a plate-like anchor elongated along a longitudinal axis extending from a vertebral penetration end of the anchor to a driving end of the anchor, the anchor comprising
      a body disposed between the vertebral penetration end of the anchor and the driving end of the anchor, a first edge oriented generally in a direction of the longitudinal axis and disposed along the body of the anchor, a second edge oriented generally in a direction of the longitudinal axis and disposed along the body of the anchor, a first surface extending between the first edge and the second edge and being concave along a direction of the longitudinal axis, a second surface extending between the first edge and the second edge and being convex along a direction of the longitudinal axis and disposed on an a side of the body opposite the first surface, and a rib protruding from the body between the first edge and the second edge and extending generally in a direction of the longitudinal axis; and an implant comprising first and second vertebral contact surfaces, a passage having an opening along an edge of the implant between the first and second vertebral contact surfaces and being sized and configured to accept the body of the anchor and project the vertebral penetration end of the anchor outside the implant adjacent to the first vertebral contact surface.

18. The spinal implant of claim 17 further comprising a connection disposed proximal to the driving end of the anchor and configured to connect with an anchor-extraction tool.

19. The spinal implant of claim 18 in which the connection comprises a recess.

20. The spinal implant of claim 17 in which the passage is angled from the opening toward the first vertebral contact surface.

* * * * *